US012124020B2

(12) United States Patent
Sandkuijl et al.

(10) Patent No.: US 12,124,020 B2
(45) Date of Patent: Oct. 22, 2024

(54) AUTOFOCUS SAMPLE IMAGING APPARATUS AND METHOD

(71) Applicant: Fluidigm Canada Inc., Markham (CA)

(72) Inventors: Daaf Sandkuijl, Markham (CA); Alexander V. Loboda, Thornhill (CA); Adam Carew, Toronto (CA); Khashayar Askarpour, Markham (CA)

(73) Assignee: STANDARD BIOTOOLS CANADA INC., Markham (CA)

( * ) Notice: Subject to any disclaimer, the term of this patent is extended or adjusted under 35 U.S.C. 154(b) by 814 days.

(21) Appl. No.: 17/274,295

(22) PCT Filed: Sep. 10, 2019

(86) PCT No.: PCT/US2019/050330
§ 371 (c)(1),
(2) Date: Mar. 8, 2021

(87) PCT Pub. No.: WO2020/055810
PCT Pub. Date: Mar. 19, 2020

(65) Prior Publication Data
US 2021/0373313 A1 Dec. 2, 2021

Related U.S. Application Data

(60) Provisional application No. 62/729,239, filed on Sep. 10, 2018.

(51) Int. Cl.
*G02B 21/24* (2006.01)
*G01N 1/04* (2006.01)
(Continued)

(52) U.S. Cl.
CPC ............. *G02B 21/245* (2013.01); *G01N 1/04* (2013.01); *G01N 33/543* (2013.01);
(Continued)

(58) Field of Classification Search
CPC .. G02B 21/245; G02B 21/0032; G02B 21/26; G02B 21/006; G01N 1/04; G01N 33/543;
(Continued)

(56) References Cited

U.S. PATENT DOCUMENTS

| 4,844,617 A * | 7/1989 | Kelderman | ............... G01J 3/02 250/201.3 |
| 5,604,344 A | 2/1997 | Finarov | |

(Continued)

FOREIGN PATENT DOCUMENTS

| CN | 102648389 A | 8/2012 |
| CN | 104677864 A | 6/2015 |

(Continued)

OTHER PUBLICATIONS

First Office Action for Japan Application No. 2021-513300 mailed Sep. 29, 2023, all pages.

(Continued)

*Primary Examiner* — Georgia Y Epps
*Assistant Examiner* — Don J Williams
(74) *Attorney, Agent, or Firm* — Kilpatrick Townsend & Stockton LLP

(57) ABSTRACT

We describe in this application systems and methods for autofocusing in imaging mass spectrometry. The present application describes improvements over current IMS and IMC apparatus and methods through an autofocus component including a plurality of apertures in the autofocus system, such as a plurality of apertures arranged in 2 dimensions. As a plurality of apertures is used, the autofocus system provides redundancy in the event that measurement of focus on the sample from the illuminating radiation passed through one or more of the apertures fails so as to reduce the number of unsuccessful autofocus attempts.

23 Claims, 13 Drawing Sheets

(51) Int. Cl.
G01N 33/543 (2006.01)
G02B 21/00 (2006.01)
G02B 21/26 (2006.01)
H01J 49/00 (2006.01)
H01J 49/10 (2006.01)

(52) U.S. Cl.
CPC ....... *G02B 21/0032* (2013.01); *G02B 21/006* (2013.01); *G02B 21/26* (2013.01); *H01J 49/0004* (2013.01); *H01J 49/0031* (2013.01); *H01J 49/105* (2013.01); *G01N 2001/045* (2013.01); *G01N 2458/15* (2013.01)

(58) Field of Classification Search
CPC .......... G01N 2001/045; G01N 2458/15; H01J 49/0004; H01J 49/0031
See application file for complete search history.

(56) References Cited

U.S. PATENT DOCUMENTS

| | | | |
|---|---|---|---|
| 6,677,565 | B1 | 1/2004 | Wahl et al. |
| 7,557,917 | B1 | 7/2009 | Beesley |
| 2003/0184730 | A1 | 10/2003 | Price |
| 2008/0198355 | A1 | 8/2008 | Domenicali et al. |
| 2010/0277580 | A1* | 11/2010 | Stallinga ............ G02B 27/0087 359/385 |
| 2012/0206722 | A1 | 8/2012 | Grigoropoulos et al. |
| 2012/0314206 | A1 | 12/2012 | Spizig et al. |
| 2013/0070076 | A1 | 3/2013 | Kuster |
| 2016/0260598 | A1 | 9/2016 | Loboda et al. |
| 2021/0181186 | A1* | 6/2021 | Ornatsky ............ C12Q 1/6816 |

FOREIGN PATENT DOCUMENTS

| | | |
|---|---|---|
| CN | 104698068 A | 6/2015 |
| CN | 102405431 A | 9/2015 |
| CN | 104677885 A | 9/2017 |
| JP | H08-211282 A | 8/1996 |
| JP | H09-133617 A | 5/1997 |
| JP | 1090589 A | 4/1998 |
| JP | 2004-528605 A | 9/2004 |
| JP | 2013-65015 A | 4/2013 |
| JP | 2014010216 A | 1/2014 |
| JP | 2015194544 A | 11/2015 |
| JP | 2016522887 A | 8/2016 |
| WO | 2014/127034 A1 | 8/2014 |
| WO | 2014/146724 A1 | 9/2014 |
| WO | 2014/147260 A1 | 9/2014 |
| WO | 2014/169394 A1 | 10/2014 |
| WO | 2016/109825 A1 | 7/2016 |
| WO | 2017/223206 A1 | 12/2017 |
| WO | 2018011869 A1 | 1/2018 |
| WO | 2018/026898 A1 | 2/2018 |

OTHER PUBLICATIONS

Office Action for Canada Application No. 3,112,257 mailed Oct. 13, 2023, all pages.
First Office Action for China Application No. 20198007298912 mailed Nov. 8, 2023, all pages.
Abdelrahman, et al., "Lanthanide-Containing Polymer Microspheres by Multiple-Stage Dispersion Polymerization for Highly Multiplexed Bioassays", J. Am. Chem. Soc., Articles, vol. 131, pp. 1526-15283, Oct. 2009.
Ali, et al., "Automatic segmentation of adherent biological cell boundaries and nuclei from brightfield microscopy images", Machine Vision and Applications, vol. 23, pp. 607-621, May 2012.
Arce, et al., "Fast and accurate automated cell boundary determination for fluorescence microscopy", Scientific Reports, 6 pages, Jul. 2013.
Bandura, et al., "Mass Cytometry: Technique for Real Time Single Cell Multitarget Immunoassay Based on Inductively Coupled Plasma Time-of-Flight Mass Spectrometry", Analytical Chemistry, vol. 81, No. 16, pp. 6813-6822, Aug. 2009.
Bendall, et al., "Single-Cell Mass Cytometry of Differential Immune and Drug Responses Across a Human Hematopoietic Continuum", Science, Volumen 332, pp. 687-695, May 2011.
Bodenmiller, et al., "Multiplexed mass cytometry profiling of cellular states perturbed by small-molecule regulators", Nature Biotechnology. vol. 30, No. 9, pp. 858-869, Sep. 2012.
Brückner, et al., DNA Quantification via ICP-MS Using Lanthanide-Labeled Probes and Ligation-Mediated Amplification, Analytical Chemistry, vol. 86, pp. 285-291, Nov. 2013.
Doraiswamy, et al., "Excimer laser forward transfer of mammalian cells using a noveltriazene absorbing layer" Applied Surface Science, vol. 253, pp. 4743-4747, Apr. 2006.
Fernández-Pradas et al., "Laser-induced forward transfer of biomolecules", This Solid Films, vol. 453-43, pp. 27-30, Apr. 2004.
Gao, et al., "Direct labeling microRNA with an electrocatalytic moiety and its application in ultrasensitive microRNA assays" Biosensors and Bioelectronics, vol. 22, pp. 933-940, Jun. 2006.
Giesen, et al., "Highly multiplexed imaging of tumor tissues with subcellular resolution by mass cytometry", Nature Methods, vol. 11, No. 4, 417-425, Apr. 2014.
Giesen, et al., "Multiplexed Immunohistochemical Detection of Tumor Markers in Breast Cancer Tissue Using Laser Ablation Inductively Coupled Plasma Mass Spectrometry", Analytical Chemistry, vol. 83, pp. 8177-8183, Sep. 2011.
Gurevich, et al., "A simple laser ICP-MS ablation cell with wash-out time less than 100 msw z", Journal of Analytical Atomic Spectrometry, vol. 22, pp. 1043-1050, Jul. 2007.
Hodneland, et al., "CellSegm—a MATLAB toolbox for high-throughput 3D cell segmentation", Source Code for Bilogy and Medicine, vol. 8, No. 16, 44 pages, Aug. 2013.
Jiang, et al., "Rapid and robust whole slide imaging based on LED-array illumination and color-multiplexed single-shot autofocusing", Quantitative Imaging in Medicine and Surgery, 9(5), pp. 823-831, May 4, 2019.
Kindness, et al., "Two-Dimensional Mapping of Copper and Zinc in Liver Sections by Laser Ablation—Inductively Coupled Plasma Mass Spectrometry", Clinical Chemistry, vol. 49:11, pp. 1916-1923, Aug. 2003.
Laiko, et al., "Atmospheric Pressure Matrix-Assisted Laser Desorption/Ionization Mass Spectrometry", Analytical Chemistry, vol. 72, pp. 652-657, Feb. 2000.
Pogam, et al., "Spatial mapping of lichen specialized metabolites using LDI-MSI: chemical ecology issues for Ophioparma ventosa", Scientific Reports, 9 pages, Nov. 2016.
Pound, et la., "CellSeT: Novel Software to Extract and Analyze Structured Networks of Plant Cells from Confocal Images", The Plant Cell, vol. 24, pp. 1353-1361, Apr. 2012.
Qiu, et al., "Extracting a cellular hierarchy fromhigh-dimensional cytometry data with Spade", Nature Biotechnology, vol. 29, No. 10, pp. 886-893, Oct. 2011.
Wang, et al., "Fast Chemical Imaging at High Spatial Resolution by Laser Ablation Inductively Coupled Plasma Mass Spectrometry", Analytical Chemistry, vol. 85, pp. 10107-10116, Aug. 2013.
International Application No., PCT/US2019/050330 received an International Search Report and Written Opinion, mailed Jan. 9, 2020, 13 pages.
European Search Report for EP 19859992 completed May 13, 2022, all pages.
Application No. CN201980072891.2 , Notice of Decision to Grant, Mailed On Apr. 21, 2024, 2 pages.
PCT/US2019/050330 , "Invitation to Pay Additional Fees and, Where Applicable, Protest Fee", Oct. 22, 2019, 2 pages.
Canadian Application No. CA3,112,257, Office Action, Mailed On Aug. 12, 2024, 3 pages.
Japanese Application No. JP2021-513300, Office Action, Mailed On Jul. 5, 2024, 11 pages.

* cited by examiner

AUTOFOCUS SAMPLE IMAGING APPARATUS AND METHOD

CROSS REFERENCE TO RELATED APPLICATION

This PCT application claims priority to U.S. Provisional Patent Application No. 62/729,239, filed Sep. 10, 2018, the entire contents of which are incorporated by reference for all purposes.

FIELD OF THE INVENTION

The present invention relates to the imaging of samples using imaging mass spectrometry (IMS) following laser ablation and the imaging of biological samples by imaging mass cytometry (IMC™).

BACKGROUND

Focus is an important parameter in many measurement technologies. Systems which can automatically focus radiation (autofocus systems) have been used for imaging of biological substances and to enable laser radiation to ablate different locations of a sample.

One group of existing autofocus systems utilise an aperture, through which radiation is directed into one or more lenses, then onto the sample and reflected towards a sensor. Several different relative positions of aperture and sample are tested and the position with greatest intensity is selected as most focused. This kind of autofocus system can fail with biological samples. This is a particular issue for systems reliant on removal of sample material from a sample e.g. by laser ablation, because if the laser is confocal with the autofocus system, failure to autofocus jeopardizes both data quality and sample integrity.

It is an object of the invention to provide further and improved apparatus and techniques for imaging of samples.

SUMMARY OF THE INVENTION

In general terms, the analyser apparatus disclosed herein comprises three broadly characterised systems for performing imaging elemental mass analysis.

The apparatus may include an autofocus system. The autofocus system may include an illumination source and an autofocus sensor. The apparatus may further include one or more of a sampling system, optical microscope, and movable sample stage. The sampling system and autofocus system (and optionally further the optical microscope) may be confocal. The apparatus may include additional systems, as described herein.

The first is an autofocus system, which places the sample at the correct point in the sample chamber for optimum sampling by the laser of the sampling and ionisation system.

The second is a sampling and ionisation system. This system contains a sample chamber, which is the component in which the sample is placed when it is subjected to analysis. The sample chamber comprises a stage, which holds the sample (typically the sample is on a sample carrier, such as a microscope slide, e.g. a tissue section, a monolayer of cells or individual cells, such as where a cell suspension has been dropped onto the microscope slide, and the slide is placed on the stage). A laser in the sampling and ionisation system acts to remove material from the sample in the sample chamber (the removed material being called sample material herein) which is converted into ions, either as part of the process that causes the removal of the material from the sample or via a separate ionisation system downstream of the sampling system. To generate elemental ions, hard ionisation techniques are used. The ionised material is then analysed by the third system which is the detector system. The detector system can take different forms depending upon the particular characteristic of the ionised sample material being determined, for example a mass detector in mass spectrometry-based analyser apparatus.

The present invention provides improvements over current IMS and IMC apparatus and methods through an autofocus component including plurality of apertures in the autofocus system, such as a plurality of apertures arranged in 2 dimensions. The illumination source of the autofocus system directs radiation onto the sample to be ablated through the plurality of apertures. As a plurality of apertures is used (i.e. more than one aperture is available for focus analysis) the autofocus system provides redundancy in the event that measurement of focus on the sample from the illuminating radiation passed through one or more of the apertures fails (e.g. because tissues with varying composition, uneven topology, or voids, can at certain positions fail to reflect the illuminating radiation such that it can be well detected through a single aperture for autofocusing) so reducing the number of unsuccessful autofocus attempts.

Thus, in operation, the sample is taken into the apparatus, and how in focus the sample is measured (e.g. by assigning a focus score) for a given relative position of the focal point of illumination radiation and the sample. The relative position of the focal point of illumination radiation and the sample is then changed, and a measurement of the focus for the one or more changed positions taken. The positions can then be compared, and a direction or position of increasing focus established. The relative position can then be changed again, and optionally a further measurement taken. The process can be repeated to improve the focus score further. Once a desired focus score is achieved, the sample can be sampled (e.g., by laser ablation) to generate ionised material using a laser source (sampling may generate vaporous/particular material, which is subsequently ionised by the ionisation system), and the ions of the sample material are passed into the detector system. Although the detector system can detect many ions, most of these will be ions of the atoms that naturally make up the sample. In some applications, for example analysis of minerals, such as in geological or archaeological applications, this may be sufficient.

In some cases, for example when analysing biological samples, the native element composition of the sample may not be suitably informative. This is because, typically, all proteins and nucleic acids are comprised of the same main constituent atoms, and so while it is possible to tell regions which contain protein/nucleic acid from those that do not contain such proteinaceous or nucleic acid material, it is not possible to differentiate a particular protein from all other proteins. However, by labelling the sample with atoms not present in the material being analysed under normal conditions, or at least not present in significant amounts (for example certain transition metal atoms, such as rare earth metals; see section on labelling below for further detail), specific characteristics of the sample can be determined. In common with IHC and FISH, the detectable labels can be attached to specific targets on or in the sample (such as fixed cells or a tissue sample on a slide), inter alia through the use of SBPs such as antibodies, nucleic acids or lectins etc. targeting molecules on or in the sample. In order to detect the ionised label, the detector system is used, as it would be to detect ions from atoms naturally present in the sample. By linking the detected signals to the known positions of the sampling of the sample which gave rise to those signals it is possible to generate an image of the atoms present at each position, both the native elemental composition and any labelling atoms. In aspects where native elemental composition of the sample is depleted prior to detection, the image may only be of labelling atoms. The technique allows the analysis of many labels in parallel (also termed multiplexing), which is a great advantage in the analysis of biological samples.

The invention provides an autofocus component, the autofocus component comprising a plurality of apertures.

The invention also provides an autofocus system for focusing on a sample comprising:
- an illumination source to emit radiation to illuminate the sample;
- an autofocus component of the invention, which permits radiation from the illumination source to pass through the plurality of apertures;
- an objective lens disposed in the optical path of the radiation to focus the radiation towards the sample; and
- an autofocus sensor arranged to receive radiation reflected from the sample, and arranged to be confocal with the autofocus component.

The invention also provides an apparatus for analysing a biological sample, comprising:
- an autofocus system, and
- a sampling and ionisation system to remove material from the sample and to ionise said material to form elemental ions, wherein the sampling and ionisation system comprises a laser source for sampling the sample;
wherein the focal point of the laser source of the sampling and ionisation system is confocal with the autofocus component and autofocus sensor of the autofocus apparatus.

In some embodiments, the sampling and ionisation system comprises a sampling system and an ionisation system, wherein the sampling system comprises the laser source and the sample stage and wherein the ionisation system is adapted to receive material removed from the sample by the sampling system and to ionise said material to form elemental ions.

Aspects of the invention also provides an autofocusing method comprising:
- determining the focus score of a first position of a sample,
- moving the sample to a second position,
- determining the focus score of the second position, and
- comparing the focus scores to each other,
- wherein determining the focus score comprises illuminating a sample with radiation from an illumination source, the illumination radiation being passed through an autofocus component comprising multiple apertures, and detecting illumination radiation reflected from the sample, and wherein moving the sample is movement parallel to the axis in which the illumination radiation is directed onto the sample (i.e. movement is in the z-axis).

Aspects of the invention also provides an autofocusing method comprising:
- determining the direction of focus at a position n of a sample,
- moving the sample in the direction of focus to position (n+1),
- wherein determining the direction of focus comprises illuminating a sample with radiation from an illumination source, the illumination radiation being passed through an autofocus component comprising multiple apertures, wherein at least two of the apertures of the autofocus component are offset in the axis at which the illumination radiation passes through the autofocus component, and detecting illumination radiation reflected from the sample with an autofocus sensor, and wherein moving the sample is movement parallel to the axis in which the illumination radiation is directed onto the sample (i.e. movement is in the z-axis).

Aspects of the invention also provide a method of mapping the topology of a surface comprising, performing a method of autofocusing (for instance a method comprising the autofocus method), moving the sample in the plane of the sample (i.e. in the X and/or Y axis) to a second position in the plane of the sample, and performing a method comprising the autofocus method of the invention, respectively, again to record the optimum focal position at the second position in the plane of the sample.

The invention also provides a method of analysing a sample comprising:
- performing the method of the invention to place the sample at the focus point of a laser for laser ablation;
- performing laser ablation of the sample on a sample stage at multiple locations; and
- subjecting the plumes to ionisation and mass spectrometry, whereby detection of atoms in the plumes permits construction of an image of the sample, optionally wherein the multiple locations are multiple known locations.

DETAILED DESCRIPTION OF THE INVENTION

Figure 1:
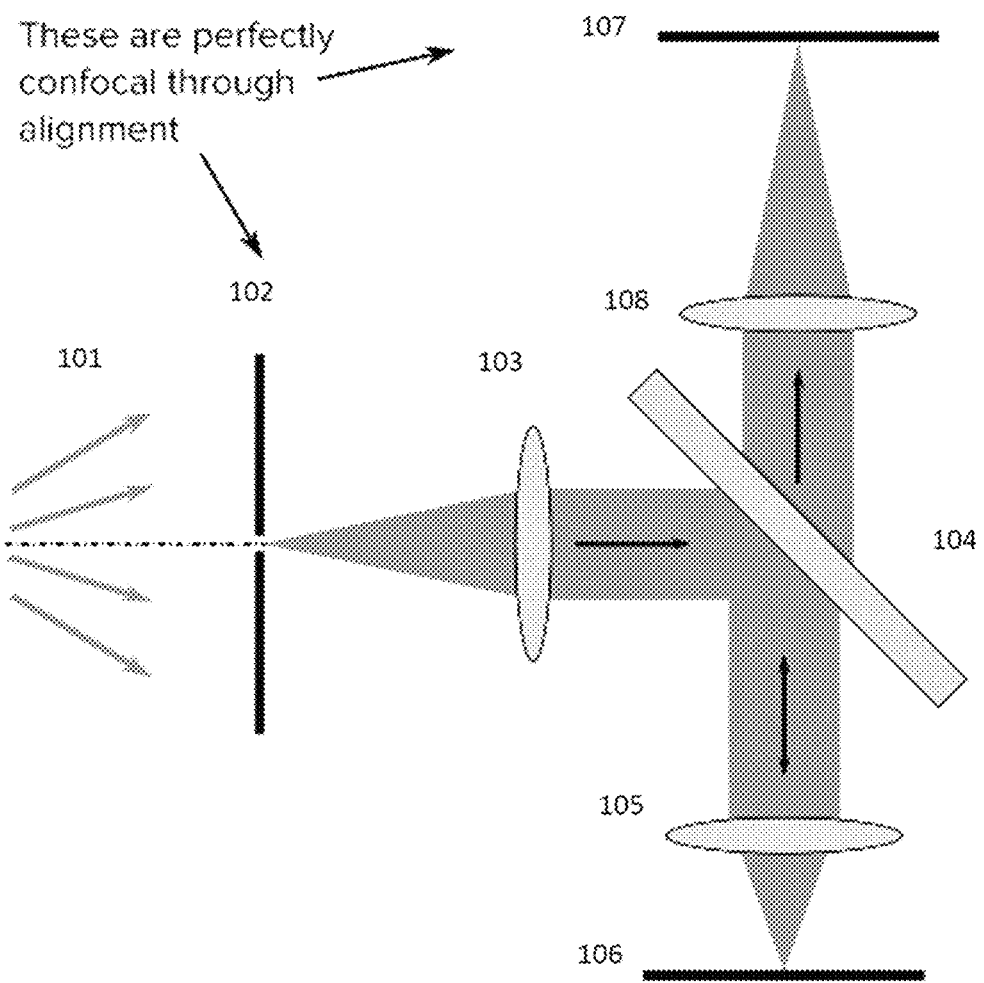
FIG. 1—A schematic of the illumination radiation path in a prior art autofocus system comprising a single aperture autofocus component in which the sample is in perfect focus.

In operation, radiation is emitted from an illumination source, passes through the apertures of an autofocus component comprising a plurality of apertures, and is directed towards the sample on a stage. The illumination radiation is reflected by the sample. The reflected radiation is directed to an autofocus sensor which is confocal with the autofocus component. A laser of a laser based sampling and ionisation system, if present, is also confocal with the autofocus component and the autofocus sensor. Reflected radiation from can be detected at a number of positions on the autofocus sensor, each position correlated to the aperture in the autofocus component through which the radiation passed. The reflected radiation detected at the sensor is analysed (e.g. to calculate a focus score, such as by assessing the intensity of radiation at each position correlated to an aperture—the summed total of intensity from the positions corresponding to all apertures), The relative position of the focal point of illumination radiation and the sample is then changed, and further measurement of the focus by the autofocus sensor of the radiation reflected from the sample is taken. The process may then be repeated, adjusting the relative position of the focal point of illumination radiation and the sample a third time, and measuring a third focus, and so on. The cycle can be repeated iteratively until a maximum focus is reached. The sample can then be sampled and ionised by the sampling and ionisation system comprising the laser, if present, with greatest efficacy due to the positioning of the sample at the focal point of the laser (confocal with the autofocus sensor and the apertures of the autofocus component). Thus various types of autofocus apparatus comprising an autofocus component of the invention comprising a plurality of apertures can be used in practising the disclosure, a number of which are discussed in detail below.

Analyser Apparatus Based on Mass-Detection

Autofocus systems and methods of the subject application may provide one or more benefits, such as no need for pre-processing, rapid autofocusing, a low cost solution to autofocusing, feature creation, generating a focal map, and/or improved accuracy. In certain aspects, the autofocusing systems and methods may provide autofocusing for laser ablation based mass spectrometry. Autofocusing systems and methods may also provide focusing of an optical microscope (e.g., inspection system) used to guide laser ablation based mass spectrometry. The sample may be a biological tissue that varies in surface topology. In certain aspects, the sample may be stained with mass-tagged SBPs. Unlike traditional fluorescent microscopy, imaging mass cytometry does not acquire an image across a large field of view simultaneously. Rather, individual spots (e.g., pixels) are removed from the sample by radiation (such as laser ablation), and delivered to a mass spectrometer. To obtain images with single-cell resolution or better, individual spots are small (e.g., within an order of magnitude of a micron). As such, focusing radiation on the sample with precision is important. Variations in the tilt of a sample (or supporting slide), variations in the control of a sample stage, system drift, and/or variations in topology of the sample may lead to variation in the relation of the focal point to the sample surface, adversely affecting sampling and consistency of sampling.

An apparatus of the subject application may include an autofocus system according to any of the embodiments described herein. The autofocus system may include an illumination source and an autofocus sensor. As discussed further herein, the apparatus may include additional components.

In certain aspect, the apparatus further includes a sampling system, such as a laser ablation system. The sampling system and autofocus system may be confocal. The apparatus may further include an optical microscope for inspection of a sample, such as to identify a region of interest. The apparatus may further include a movable sample stage.

The illumination source of the autofocus system may be a laser diode with appropriate beam shaping optics, or a bright LED with a particular lens system and aperture or set of apertures, for example. The detector could be the same camera as used for inspection (distinguishing between the autofocus light and illumination light can be achieved in real time by LED pulsing, optical filtering, or non real time by performing autofocus at the beginning or end of each line), a line sensor oriented along the expected translation direction, or a position-sensitive photodiode, for example. In certain aspects, the illumination source of the autofocus system may be shared with an optical microscope. Alternatively, the illumination source of the autofocus system may be separate from the illumination source of an optical microscope.

The autofocusing system may provide an illumination scheme where a strip or other pattern of light is incident on the slide at some angle, and then detect the XY position of the pattern of light on the slide surface using some detector (a camera or other position-sensitive device). Due to the angle between the incident light and the slide normal, the displacement of the returned light as compared to some calibrated best-focus position would be linearly dependent on the amount of defocus, and hence the best focus position can be found directly (no full scan needed).

Autofocus System

The autofocus system typically comprises a series of components, such as an autofocus component comprising a plurality of apertures, an illumination source and an autofocus sensor. Various optical components can be included, as appropriate, based on the arrangement of these components.

The autofocus system described herein can be used in methods of the invention described herein that employ an autofocusing step. Thus the invention provides the use of an autofocus system of the invention for autofocusing an apparatus (e.g. imaging mass cytometer of imaging mass spectrometer).

The apparatus may be configured to provide autofocusing (e.g., autofocusing correction) by moving the sample stage and/or adjusting optical elements. In certain aspects, the apparatus may be configured to provide autofocusing by moving the sample stage in response to a readout from the autofocus component. In certain aspects, the apparatus is not configured for autofocusing by adjusting optics, such as when only the z-position of a sample stage is moved. As such, optics may not be movable to provide focusing.

The apparatus may provide sample-independent autofocusing, e.g., which is not dependent on features or contrast provided by the sample. The autofocusing system may provide autofocusing during a sample run, for example, when the sample stage has positioned the sample at different X,Y coordinates.

In certain aspects, the autofocus system provides rapid autofocusing (e.g., rapid autofocus corrections). For example, the autofocus system may provide autofocusing feedback at 100 Hz or faster, 200 Hz or faster, 500 Hz or faster, 1 kHz or faster, 2 kHz or faster, 5 kHz or faster, or 10 kHz or faster.

In certain aspects, the autofocusing may be performed as a closed loop, such as a PID loop in which autofocusing provides immediate adjustment to actuators. In certain aspects, a PID controller continuously calculates an error value as the difference between a desired setpoint and a measured process variable, and applies a correction based on proportional, integral, and derivative terms.

In certain aspects, autofocusing may be performed at the hardware level, without processing autofocusing data at a software level. Hardware-based autofocusing may drastically reduce the cycle time for autofocusing.

Autofocusing correction may be performed by adjusting the optics (e.g., distance between optical elements), via positioners that adjust focus in the Z-direction, and/or adjustment of the sample stage in the Z-direction. In certain aspects, autofocusing correction may be performed by adjusting the z-position of the sample stage.

In certain aspects, the autofocus system may project a focal map across X, Y, or X-Y coordinates (e.g., may create a focal map that guides autofocus correction across a range of coordinates). The focal map may provide, or be used to provide, an adjustment to the focal point of the laser ablation optics across a plurality of coordinates, without the need to perfume autofocusing at each coordinate. In certain cases, the coordinates may be sample coordinates (e.g., coordinates across a tissue sample). The sample stage may be moved to position the sample at a new coordinate. Alternatively or in addition, the laser may be continuously scanned across coordinates by one or more positioners. A positioner may be a mirror-based positioner (such as a galvanometer mirror, a polygon scanner, a MEMS mirror, piezoelectric device mirror) or a solid state positioner (such as an AOD or an EOD). The focal map may provide a point of best focus (e.g., in the z-direction) across (e.g., at) a plurality of coordinates, or may provide an adjustment to the optics to get to best focus from an initial position. As such, the focal map may be based on a relative (e.g., starting) or objective frame of reference. In certain aspects, a sample stage may be moved in the z-direction while a laser is scanned along a focal line in the X,Y plane.

In certain aspects, autofocusing may allow for selective sampling or removal of surface material that is at a higher z-position compared to surrounding material, such that an even sample surface is obtained for subsequent interrogation.

The apparatus may be further configured to provide an optical image during a sample run. For example, the apparatus may include an image sensor, such as a CCD or CMOS, that provides an optical image of the sample. The apparatus may include an optical microscope (of which the image sensor is a part), such as a brightfield/widefield microscope or a fluorescent microscope. The optical microscope may be used to inspect the sample, such as to identify a region of interest to sample from by laser ablation.

The autofocus system may comprise at least one aperture. An illumination source (such as from an LED) that impinges on an aperture may provide a feature reflected from the sample (or sample support) onto the autofocus sensor. In certain aspects, the autofocus system comprises a plurality of apertures, such as three or more apertures arranged in two dimensions.

The autofocus system may provide multiple features (i.e., spots of any shape) that impinge on the autofocus sensor. An autofocus system may provide multiple through the use of multiple apertures, alternating illumination sources (such as 2 or more LEDs or laser diodes), and/or a diffractive beamsplitter.

Autofocus Component Comprising a Plurality of Apertures

The invention provides an autofocus component, the autofocus component comprising a plurality of apertures. The apertures permit radiation to pass through them. Typically the material of the autofocus component otherwise does not permit radiation to pass through it.

Prior approaches to autofocusing are characterised by a reliance on a single aperture, which results in unproductive autofocusing attempts when illumination radiation passing through the single aperture is obscured or otherwise impeded (so that illumination radiation from the aperture does not properly reach the sensor). A false intensity (or absence of intensity) is therefore detected. For instance, the point on the sample to which illumination radiation is directed through a single aperture may not be reflective, e.g. because there is no biological material there (as may happen when voids have been introduced into tissue sections as a result of preparation procedures, or as a result of the random distribution of cells onto a slide in a cell smear).

By providing a plurality of apertures, the autofocus component introduces redundancy into the autofocus system, such that the failure of illumination radiation to reflect from the sample can be compensated for by the reflected illumination radiation detected from the remaining apertures. The autofocus system is therefore made more robust, reducing the time spent on failed autofocus attempts and improving efficiency. An increased number of apertures results in improved robustness of autofocusing by making available additional apertures in the event other apertures fail. Accordingly, in some instances, the autofocus component comprises at least two apertures, for example at least three, at least four, at least 5, at least six, at least seven, at least 8, at least 9, at least 16 or at least 25 apertures.

In some instances, the apertures of the autofocus component are arranged in a regular shape. A regular shape enables efficient coverage of an area of a sample. Accordingly, in some instances, the apertures of the autofocus component are arranged at the vertices of a regular polygon, for example, the 3 vertices of a triangle, the 4 vertices of a square or rectangle, the 5 vertices of a pentagon, the 6 vertices of a hexagon, the 7 vertices of a heptagon, the 8 vertices of an octagon, the 9 vertices of a nonagon, or the 10 vertices of a decagon.

In some instances in which the apertures of the autofocus component are arranged in a regular shape, the vertices of the regular shape can be arranged at a constant distance from the centroid of the polygon. Polygons with shorter such distances produce greater redundancy over a small area of the sample. Conversely, polygons with larger distances enable topology analysis, as discussed below in more detail, over a wider area of the sample and/or more quickly. In some instances, the distance from the centroid of the polygon to each vertex is less than 10 μm, 15 μm, 20 μm, 25 μm, 50 μm, 75 μm, 100 μm, 150 μm, 200 μm, 250 μm, 500 μm, 750 μm, or 1 mm. In some instances, the distance from the centroid of the polygon to each vertex is more than 10 μm, 15 μm, 20 μm, 25 μm, 50 μm, 75 μm, 100 μm, 150 μm, 200 μm, 250 μm, 500 μm, 750 μm, or 1 mm.

In preferred instances in which the apertures of the autofocus component are arranged in a regular shape, the component may comprise further apertures in addition to the vertex apertures described above. In one such instance, a further aperture is present at the centroid of the polygon. This centroid aperture typically is arranged to transmit illumination radiation to the point on a sample at which ablation of the sample will occur, e.g. by the laser ablation sampling system as discussed herein. Thus, where the plurality of apertures (less the centroid aperture) allow measurement of focus around the location of sampling, a centroid aperture contributes to the focus calculation with a reading from the precise point of ablation. In another such instance, the component comprises further apertures at the midpoint of the sides of the polygon defined by the vertex apertures. These peripheral apertures enhance the efficient coverage of the sample area by providing further positions which can be used in calculating focus.

In other instances, the apertures are arranged in a regular grid. A regular grid afford the same efficient coverage of a sample area, but may be preferable for certain shapes and/or topologies of sample. In some instances, the apertures are in a regularly spaced grid, such as a 2×2 grid, a 3×3 grid, a 4×4 grid, a 5×5 grid, a 6×6 grid, a 7×7 grid, an 8×8 grid, a 9×9 grid, a 10×10 grid or a more than 10×10 grid.

In instances in which the apertures of the autofocus component are arranged in a regular grid, neighbouring grid apertures can be spread a certain inter-aperture distance from the centerpoint of the apertures. Grids with shorter such distances produce greater redundancy over a small area of the sample. Conversely, grids with larger distances enable topology analysis, as discussed below in more detail, over a wider area of the sample and/or more quickly. In some instances, the inter-aperture distance between neighbouring grid apertures is 10 μm, 15 μm, 20 μm, 25 μm, 50 μm, 75 μm, 100 μm, 150 μm, 200 μm, 250 μm 500 μm, 750 μm, or 1 mm measured from the centerpoint of the apertures. In some instances the apertures are polygonal, such as triangular or square.

In some instances, the shape of the apertures is chosen to maximise the robustness of focus score measurement. In some instances, the apertures are circular and of diameter at or less than 1 μm, 2.5 μm 5 μm, 7.5 μm, 10 μm, 15 μm, 20 μm, 25 μm 50 μm, 75 μm, or 100 μm. In some instances, the apertures are circular and of diameter at or greater than 1 μm, 2.5 μm 5 μm, 7.5 μm, 10 μm, 15 μm, 20 μm, 25 μm 50 μm, 75 μm, or 100 μm.

For application in some methods described herein, which relate to calculation of optimum focal position on the basis of collection of illumination radiation focused through multiple apertures in a single focal plane, an autofocus component with this arrangement of apertures is required. Accordingly, in some embodiments the autofocus component is planar (such that all apertures are in the same focal plane).

In some embodiments, the autofocus component comprises apertures that are offset relative to one another in the axis of illumination radiation. That is to say that the autofocus component comprises one or more steps, or in yet further terms, comprises two or more aperture planes. See e.g. feature 502 in FIG. 5. In some embodiments, the autofocus component comprises two aperture planes. In some embodiments, the autofocus component comprises three aperture planes. In some embodiments, the autofocus component comprises four or more aperture planes. In some embodiments, each aperture plane comprises more than one aperture, for example, three apertures per aperture plane. In some instances comprising two aperture planes, the planes will be offset equally either side of the plane which is confocal with the detector. In use, therefore, this autofocus component would indicate perfect focus when both planes of apertures are equally defocused. When the aperture(s) at one level is/are more defocused than the one(s) at the other level, the direction of the focus plane from the sample is indicated. In embodiments with three aperture planes, one aperture plane may be confocal with the autofocus detector and the two further planes will be offset equally either side of the aperture plane which is confocal with the detector. In use, therefore, this autofocus component would indicate perfect focus when the first aperture plane was in focus, and both of the two further planes of apertures were equally defocused.

In some embodiments, the autofocus component acts as a hybrid mask of the illumination source. Such hybrid autofocus components comprise an opaque region which blocks illumination radiation, in which the multiple apertures are positioned, but otherwise comprises regions which permit transmission of the illumination radiation onto the sample (either through the use of radiation transparent materials or by simply leaving comparatively large voids in the autofocus component). The regions are different in size from the apertures in the autofocus component. Accordingly, by using such an autofocus component, autofocusing can occur in line with the description herein, but at the same time the illumination radiation is allowed onto the sample so that the sample can be visibly inspected by the autofocus sensor (when it is a camera or device with comparable function). In some embodiments, the apertures of the hybrid autofocus component are offset relative to one another in the axis of illumination radiation. Accordingly, in some embodiments, the hybrid autofocus component comprises offset apertures, such as offset planes of apertures, as described in any embodiment in the preceding paragraph. Use of such a hybrid autofocus component permits 'live' autofocusing— i.e. maintaining best focus when the sample is moved in directions perpendicular to the optical axis (i.e., during ablation of the sample, for 'live' autofocusing). This autofocus component and method would allow for ablation, sample viewing, and focus tracking to be performed simultaneously.

The invention provides the use of an autofocus component, such as that described above, in the method described herein (e.g. in the sections "Methods for autofocusing" on page 25 and Sample topology mapping methods on page 29, including each and every of the specific embodiments discussed in those sections).

Illumination Source

An autofocus system as described herein includes an illumination source. The illumination source may include at least one LED or laser diode, but may include two or more LEDs, two or more laser diodes, or a combination of LEDs and laser diodes. In certain aspects, two or more LEDs or laser diodes provide different features that impinge on an autofocus sensor. When LEDs are used, an aperture positioned between an LED and the sample may provide a feature. In certain aspects, the apparatus may not need to switch between autofocus and inspection apertures.

In certain aspects, two LEDs or laser diodes may provide alternating illumination. The autofocus system may be configured such that features produced by the alternating illumination overlap when the system (e.g., laser ablation system) is in focus. Alternating laser diodes radiation may be faster than alternating LED radiation. Further, laser diodes may provide brighter and/or smaller features than LED radiation through an aperture. However, the cost of laser diodes may be higher than LEDs.

In certain aspects, the illumination source may be a color multiplexed illumination source. The illumination source may include a programmable LED array. For example, the transitional shift of images produced by two colors of LED illumination may be used for dynamic focus correction. Color-multiplexed autofocusing is discussed in the context of whole slide imaging by Jiang, Shaowei, et al. "Rapid and robust whole slide imaging based on LED-array illumination and color-multiplexed single-shot autofocusing." arXiv: 1905.03371 (2019).

In certain aspects, one or more of the illumination sources provides illumination at a non-zero angle to the sample normal. Illumination provided the non-zero angle may be from one or more laser diodes and/or LEDs directed through an aperture. A feature provided by the illumination may reflect from the sample and/or sample support and impinge on the autofocus sensor.

In certain aspects, the autofocus system may include a plurality of apertures, and may optionally include only one light source such as an LED. The system may be configured such that the illumination that travels through the plurality of apertures provides a plurality of features incident on the autofocus sensor (e.g., after reflecting from the sample or sample support).

The illumination sources emits radiation that is directed through the plurality of apertures of the autofocus component, and then onwards towards a sample.

In some instances, the illumination source is a light-emitting diode (LED). Such illumination sources are commercially available from e.g. Olympus (Japan), Euromex (Holland).

In some instances, the illumination source is a thermal radiator or incandescent lamp, for example an incandescent tungsten-halogen bulb. The lamp can comprise an enclosed glass bulb filled with an inert gas and containing a tungsten wire filament that is energized by a DC electric current may be provided with a housing comprising one or more layers of heat sinks to help dissipate excess heat. Such illumination sources are commercially available from e.g. Cairn Research (UK).

In some instances, the illumination source is an arc lamp. Examples include metal halide, mercury vapor, xenon, and zirconium arc lamps. Such illumination sources are commercially available from e.g. World Precision Instruments (UK).

In some instances, a laser light source is used as the illumination source, for example an argon-ion laser or krypton laser. Such illumination sources are commercially available from e.g. Laser 2000 (UK).

Autofocus Sensor

Wherein the autofocus sensor comprises at least one of an image sensor (such as a CCD or CMOS), line sensor, position sensitive photodiode, adjacent photodiodes, and a split photodiode (such as a quadrature photodiode). In certain aspects, the autofocus sensor is an image sensor, and may be shared with an inspection system (e.g., such as an optical microscope).

In certain aspects the autofocus sensor is a line sensor. When the system includes an optical microscope, the optical microscope have a separate sensor from the autofocus sensor. An autofocus system that includes a line sensor may further include a cylindrical lens.

When alternating between two or more light sources providing a feature, autofocusing may include correction (e.g., by adjusting the z-position of the sample stage) until features overlap on the detector. As such, a CCD, CMOS, or line scan detector may be used to check coincidence of features. Generally, the form of detection may be agnostic to the X,Y coordinate at best focus, and may not include a detector such as a quadrature photodiode.

In certain aspects, the illumination source may be a color multiplexed illumination source. The illumination source may include a programmable LED array. For example, the transitional shift of images produced by two colors of LED illumination may be used for dynamic focus correction. Color-multiplexed autofocusing is discussed in the context of whole slide imaging by Jiang, Shaowei, et al. "Rapid and robust whole slide imaging based on LED-array illumination and color-multiplexed single-shot autofocusing." arXiv: 1905.03371 (2019).

In certain aspects, one or more of the illumination sources provides illumination at a non-zero angle to the sample normal. Illumination provided the non-zero angle may be from one or more laser diodes and/or LEDs directed through an aperture. A feature provided by the illumination may reflect from the sample and/or sample support and impinge on the autofocus sensor. The system may be pre-calibrated such that the feature impinging a particular coordinate on the autofocus sensor indicates the system is in focus. Autofocusing may then include adjusting focus (e.g., by moving optical components and/or adjusting a movable stage), checking the incidence of the feature on the autofocus sensor, and repeating until the feature is within tolerance of the pre-determined coordinate. In such cases, the autofocus sensor may be a CCD, CMOS, line array, or split photodiode.

In certain aspects, the autofocus system may include a plurality of apertures, and may optionally include only one light source such as an LED. In such cases, the autofocus sensor may be an image sensor, such as a CCD or CMOS. The system may be configured such that the illumination that travels through the plurality of apertures provides a plurality of features incident on the autofocus sensor (e.g., after reflecting from the sample or sample support). The presence of the features may be used to determine whether the system is in focus, and/or determine a correction to make to put the system in focus. The presence of the features may refer to the ability to detect the features, the focus of the features (e.g., area across which the feature is detected and/or distribution of intensity across that area), intensity of the features, and/or consistency of the intensity of the features. Autofocus corrections based on such a system may be iterative.

Data provided by the autofocus sensor may be processed by an ASIC, FPGA, or at the software level, and used to perform autofocus correction (e.g., by positioning optical elements and/or moving a sample stage).

The autofocus sensor detects radiation reflected from the sample, which is used to measure a focus score. The autofocus sensor may be a camera, e.g. charged coupled device image sensor (CCD)-based camera, an active pixel sensor (APS)-based camera, or any other radiation detecting means in an autofocus system.

In some embodiments, the sensor is (or is based on) a CCD. A CCD is a means for detecting light and converting it into digital information that can be used to generate an image. A CCD comprises a silicon chip containing an array of light-sensitive pixels. During exposure to light, each pixel generates an electric charge in proportion to the intensity of light incident on the pixel. After the exposure, a control circuit causes a sequence of transfers of electric charge to produce a sequence of voltages. These voltages can then be analysed to produce an image. Suitable CCDs are available from, for example, Cell Biosciences. In some embodiments, the sensor is an active-pixel sensor (APS). An APS is an image sensor consisting of an integrated circuit containing an array of pixel sensors, each pixel containing a photodetector and an active amplifier, e.g. a CMOS sensor. Suitable APSs are available from, for example, ON Semiconductor.

In some embodiments, the sensor is a photodetector. Photodetectors may be used to image the sample and/or identify a feature/region of interest prior to imaging by elemental mass spectrometry. Photomultipliers are available from, for example, ThorLabs.

In some embodiments, the sensor is a photomultiplier. Photomultipliers comprise a vacuum chamber comprising a photocathode, several dynodes, and an anode. A photon incident on the photocathode causes the photocathode to emit an electron as a consequence of the photoelectric effect. The electron is multiplied by the dynodes due to the process of secondary emission to produce a multiplied electron current, and then the multiplied electron current is detected by the anode to provide a measure of detection of electromagnetic radiation incident on the photocathode. Photomultipliers are available from, for example, ThorLabs.

Use of a camera provides the advantage that the autofocus sensor can be used to record an image the sample, and so can function as the camera discussed below in relation to various sampling and ionisation system components of the apparatus of the invention.

Further Components

The autofocus system may also comprise an objective lens. The objective lens focuses (e.g. 25× demagnification) the illumination radiation onto the sample. In apparatus of the invention comprising a laser based sampling system, radiation from the laser of the sampling system can be focused onto the sample by the same objective lens.

The autofocus system may also comprise tube lenses. In some embodiments, a tube lens can be positioned in the path of illumination radiation between the autofocus component and the sample, such as between the autofocus component and the one or more beam splitter component. A lens so positioned can function to collimate the illumination radiation following its passage through the apertures of the autofocus component. In some embodiments, a tube lens can be positioned in the path of illumination radiation between the sample and the autofocus sensor, such as between the one or more beam splitter components and the autofocus sensor. A lens so positioned can focus the illumination radiation reflected from the sample onto the autofocus sensor.

The autofocus system may comprise one or more beam splitters, which split incident radiation at a designated ratio into two separate beams, arranged to direct radiation from the illumination source onto the sample and to direct illumination radiation reflected from the sample to the autofocus sensor. Beam splitters typically take one of two forms: plate splitters (thin, flat glass plates that have been coated on the first surface of the substrate) and cube splitters (constructed using two typically right angle prisms). Beam splitters are widely commercially available, e.g. from rp-photonics, Thorlabs, Edmund optics.

The autofocus system may include a sample stage, which in operation of the system supports the sample (typically, the sample is on a sample carrier). The sample stage may be movable. In some embodiments the stage can move in the x, y and z axes. When the apparatus in which the autofocus system is located also comprises a sampling and ionization system, the sample stage of the autofocus system is also the sample stage of the sampling and ionization system, as discussed below (e.g. where the sample stage is within a sample chamber).

The autofocus system may also comprise a controller module. The controller module controls and co-ordinates the moments of the components of the autofocus system. In some embodiments. The controller module receives inputs from the autofocus sensor and controls the position of the sample stage during the autofocusing process on the basis of the received inputs. The controller module may comprise a programmable store programmed with instructions for performing an autofocus method of the invention as described herein, including each and every of the specific embodiments discussed in those sections. For instance, in some embodiments, the controller module comprises instructions for performing provides an autofocusing method comprising:

determining the focus score of a first position of a sample,
moving the sample to a second position,
determining the focus score of the second position, and comparing the focus scores to each other,
wherein the step of determining the focus score comprises illuminating a sample with radiation from an illumination source, the illumination radiation being passed through an autofocus component comprising multiple apertures, and detecting illumination radiation reflected from the sample with an autofocus sensor (such as wherein detecting illumination radiation reflected from the sample comprises detecting radiation at known positions (also called regions of interest) on the autofocus sensor), and
wherein moving the sample is movement parallel to the axis in which the illumination radiation is directed onto the sample (i.e. movement is in the z-axis).

In some embodiments, the controller module comprises instructions for performing provides an autofocusing method comprising:

determining the direction of focus at a position n of a sample,
moving the sample in the direction of focus to position (n+1),
wherein determining the direction of focus comprises illuminating a sample with radiation from an illumination source, the illumination radiation being passed through an autofocus component comprising multiple apertures, wherein at least two of the apertures of the autofocus component are offset in the axis at which the illumination radiation passes through the autofocus component, and detecting illumination radiation reflected from the sample with an autofocus sensor (such as wherein detecting illumination radiation reflected from the sample comprises detecting radiation at known positions (also called regions of interest) on the autofocus sensor), and wherein moving the sample is movement parallel to the axis in which the illumination radiation is directed onto the sample (i.e. movement is in the z-axis).

In some embodiments, the controller module comprises instructions for performing provides a method of mapping the topology of a sample surface comprising, performing an autofocusing method, moving the sample in the plane of the sample (i.e. in the X and/or Y axis) to a second position in the plane of the sample, and performing the autofocusing method of the invention, again to record the optimum focal position at the second position in the plane of the sample, such as wherein the autofocusing method is an autofocusing method as described in the preceding paragraphs, programmed in the controller module.

In some embodiments, the programmable store is a hard drive, optical disk, CD-ROM, DVD-ROM, ROM, RAM, EPROM, EEPROM, magnetic or optical card, solid-state memory device, or other types of media/computer-readable medium suitable for storing electronic instructions.

In some embodiments, an autofocusing apparatus for LA-ICP-MS may include wherein the apparatus does not need to switch between autofocus and inspection apertures, and may further include one or more of a movable sample stage, an optical microscope for inspection of a sample, a laser ablation sampling system, a gas conduit coupling the laser ablation sampling system to an ICP ionisation system, and/or a mass spectrometer (e.g., a time-of-flight or magnetic sector mass spectrometer). The mass spectrometer may be configured to simultaneously detect mass tags (such as lanthanides of mass tags). The autofocus system may provide multiple spots that impinge on the autofocus sensor. The sampling system and the autofocus system may be confocal. The system may be configured to provide autofocusing during a sample run by adjusting the position of the sample stage based on the multiple points of illumination.

Arrangement of the Components

With reference to FIG. 1 (which is a prior art system comprising only one aperture in the autofocus component (102)), the illumination source (101) emits illumination radiation which is transmitted through the aperture in the autofocus component (102). This illumination radiation is then collimated by a tube lens (103) and directed onto the sample by a beam splitter (104). The illumination radiation is focused onto the sample (106) by an objective lens (105), typically 25× demagnification. Illumination radiation reflected from the in focus sample (106) back along the optical path then passes back through the objective lens (105), and passes through the beam splitter (104) towards the autofocus sensor (107). Before impinging upon the autofocus sensor, the reflected illumination radiation passes through a tube lens (108). In this arrangement, the autofocus component and autofocus detector are confocal, such that when the sample is also in the focal plane, the illumination radiation reflected from the sample appears as a bright well-defined spot at the detector.

Figure 2:
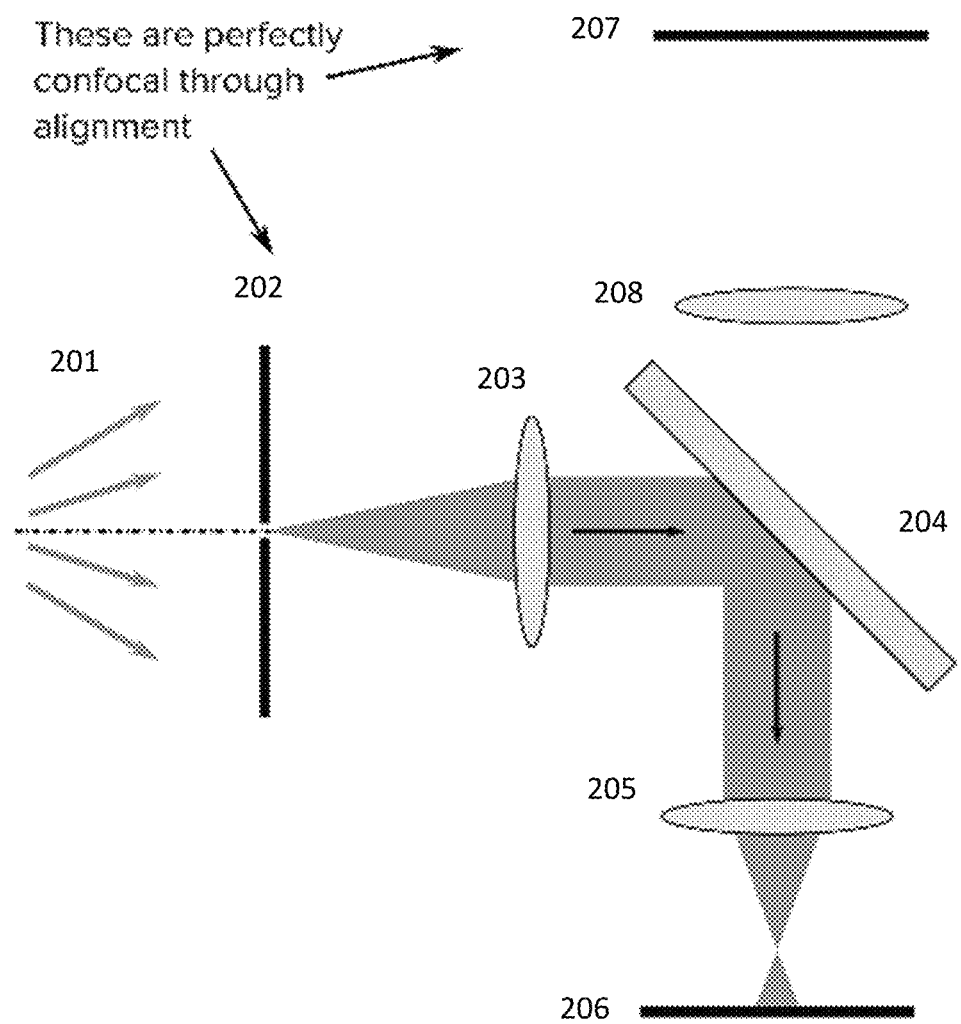
FIG. 2—A schematic of the illumination radiation path of light from the illumination source to an out of focus sample in a prior art autofocus system comprising a single aperture autofocus component.
Figure 3:
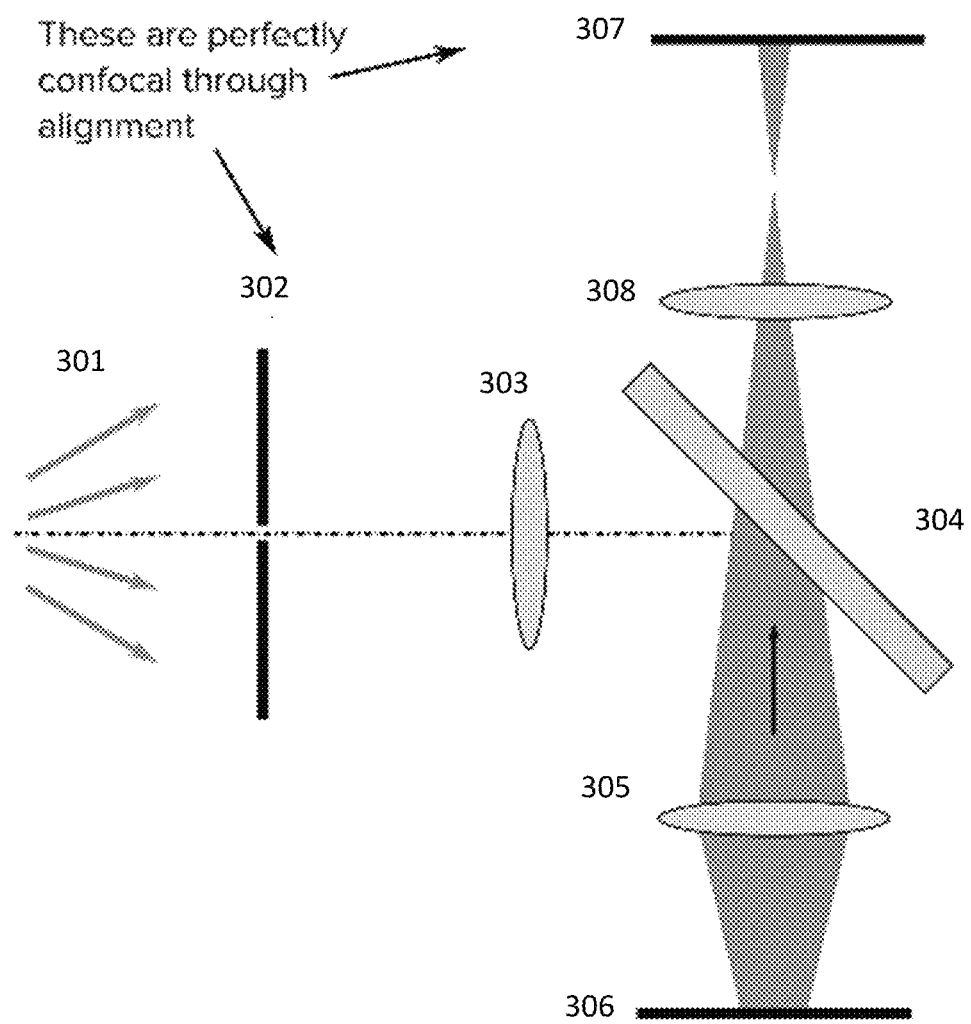
FIG. 3—A schematic of the illumination radiation path of light from the out of focus sample to the autofocus sensor in a prior art autofocus system comprising a single aperture autofocus component.

When the same is not in focus, a bright well defined spot is not detected. With reference to FIG. 2, the illumination source (201) emits illumination radiation which is transmitted through the aperture in the autofocus component (202). This illumination radiation is then collimated by a tube lens (203) and directed onto the sample by a beam splitter (204). The illumination radiation is focused by an objective lens (205) toward the sample (206). Because the sample is not at the focal plane of the Illumination radiation, the illumination radiation is defocused on the sample (206). Turning now to FIG. 3, the defocused illumination radiation is reflected from the out of focus sample (306) back along the optical path then passes back through the objective lens (305), and passes through the beam splitter (304) towards the autofocus sensor (307), where it is further defocused. Thus when the sample is out of focus with the autofocus sensor (207/307), the autofocus component (202/302) will be as well, and so the illumination radiation from the aperture of the autofocus component (202/302) will be defocused on the sample (206/306) and further defocused on the autofocus sensor (207/307). The sample can be moved to place the sample in focus by movement of the sample stage. However if the particular region onto which the illumination radiation is being directed is not reflective, then no focusing can be achieved by the prior art apparatus and method, as noted above.

Figure 4:
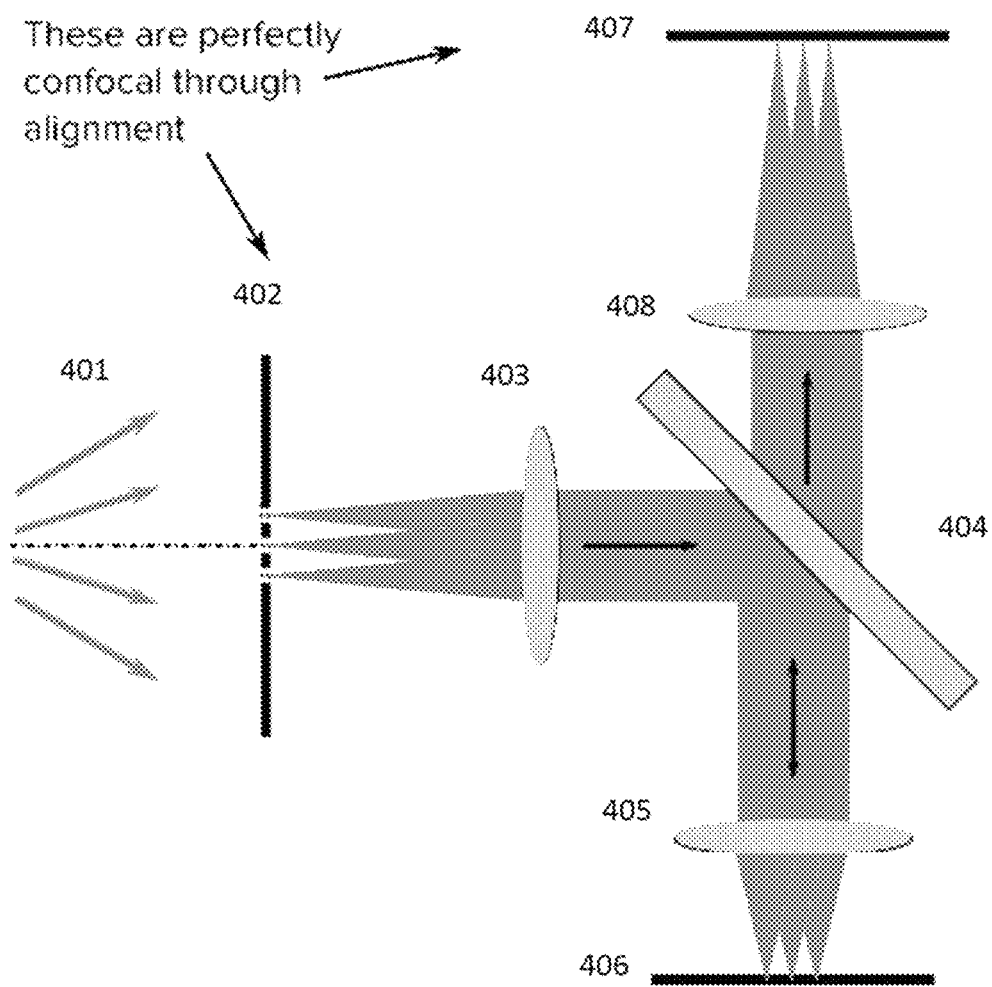
FIG. 4—A schematic of the illumination radiation path in a prior art autofocus system comprising a multiple aperture autofocus component of the invention in which the sample is in perfect focus.

With reference to FIG. 4, the apparatus of the invention operates on the basis of a similar principle. However, the expected number of spots detected on the autofocus sensor (407) corresponds to the number of apertures in the autofocus component (402); three apertures are illustrated in FIG. 4. Because multiple apertures are used, beams of illumination radiation are focused to separate points on the sample (406), and so reflect to separate points on the sample detected (407), with these points being known (and also called regions of interest herein). Accordingly, reflected illumination radiation can be detected in expected areas (see e.g. FIG. 8, which uses a 9-aperture autofocus component with the apertures being arranged in a grid). With the autofocus component of the invention, even if some of the points on the sample to which illumination radiation is directed do not reflect the illumination radiation back to the autofocus sensor, other apertures will (see FIG. 9, which illustrates the utility of a 9-aperture autofocus component, as 7 of the signals from the peripheral apertures are focused to a point, but yet the middle aperture has returned no reflected illumination radiation). In this instance, a one aperture autofocus component would fail to focus, but the autofocus component of the invention allows the autofocus system to succeed.

Figure 5:
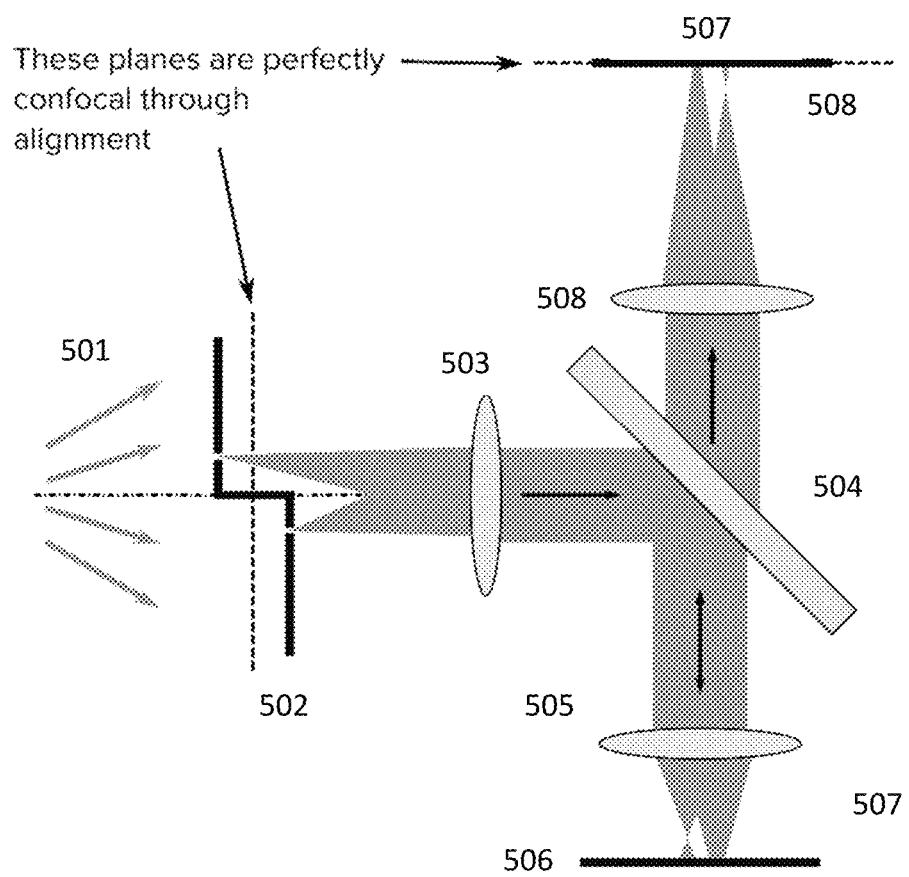
FIG. 5—A schematic of the illumination radiation path in a prior art autofocus system comprising a multiple aperture autofocus component of the invention with offset apertures in which the sample is in perfect focus.

As illustrated in FIG. 5, in a further development, the inventors have determined that the autofocus component can comprise multiple planes of apertures (502). In line with the preceding descriptions, the illumination source (501) emits illumination radiation which is transmitted through the aperture in the autofocus component (502) m which comprises two planes of apertures, distanced equally either side of a plane that is confocal with the autofocus sensor (507). As the apertures are on different planes, illumination radiation passing through them has different focal planes at the sample, and so, at the autofocus sensor, does illumination radiation reflected from the sample. The illumination radiation is then collimated by a tube lens (503) and directed onto the sample by a beam splitter (504). The illumination radiation is focused toward the sample by an objective lens (505). Because the sample is not at the focal plane of the Illumination radiation, the illumination radiation is defocused on the sample (506), with illumination radiation from the apertures at different focal planes being equally defocused (509). The defocused illumination is equally defocused from the apertures at each plane of the autofocus component (502) at the sample (506), however, meaning that the sample is in focus. The defocused illumination radiation (509) is reflected from the sample (506) back along the optical path then passes back through the objective lens (505), and passes through the beam splitter (504) towards the autofocus sensor (507), where it is also defocused, but the detected reflected illumination radiation from each plane of apertures is equally defocused, indicating that the sample (506) is in focus. When the sample (506) is out of focus, the autofocus sensor (507), will detect the reflected illumination radiation from each plane of apertures of the autofocus component (502) having a different degree of focus. The manner in which the focus differs between reflected illumination radiation from different planes of apertures of the autofocus component (502) can be used to calculate the direction in which the sample should be moved to bring the reflected illumination radiation from different planes of apertures of the autofocus component (502) into equal degrees of defocusing.

Figure 6:
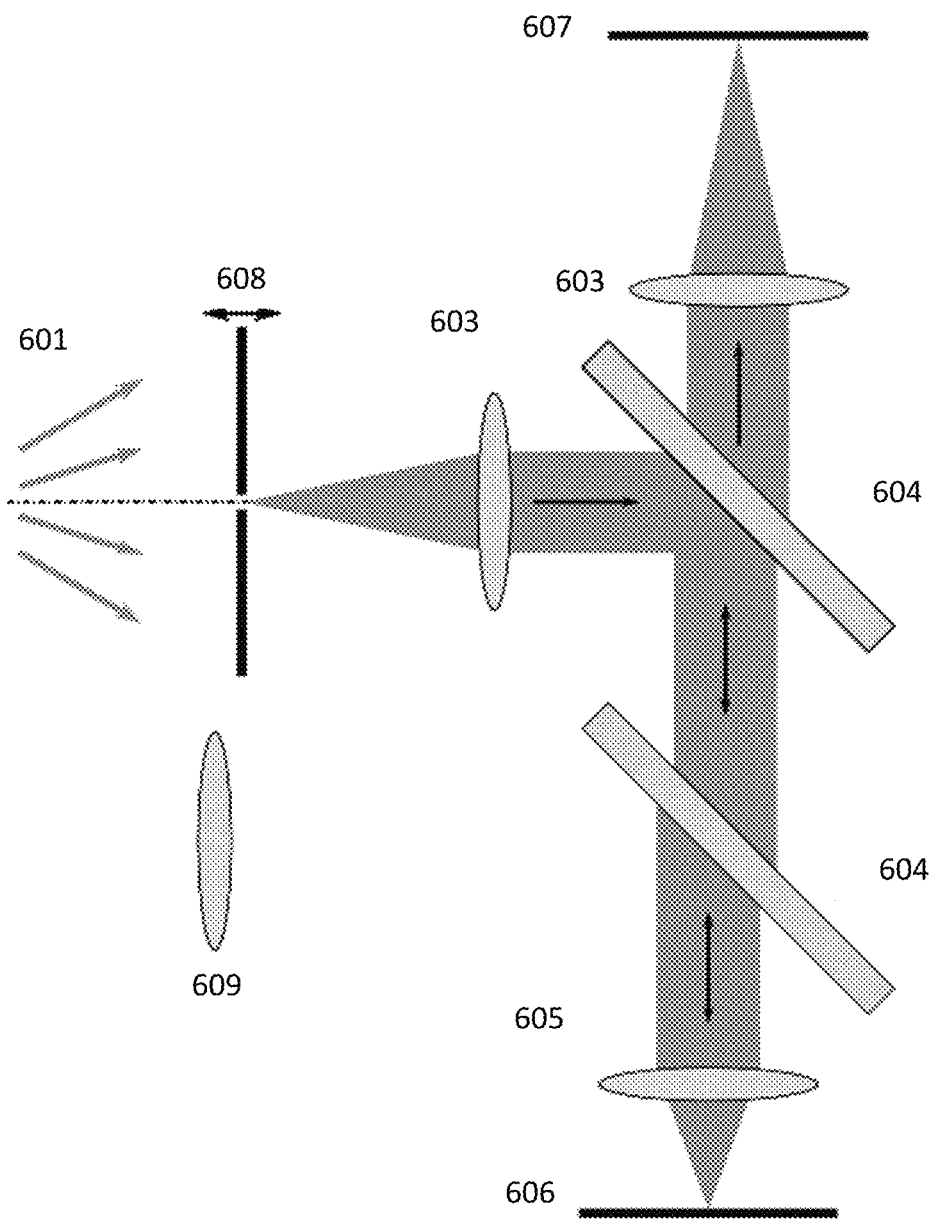
FIG. 6—A schematic of the process of bringing the autofocus component into a confocal position with the autofocus sensor during the production of an autofocus system according to embodiments of the present invention.
Figure 7:
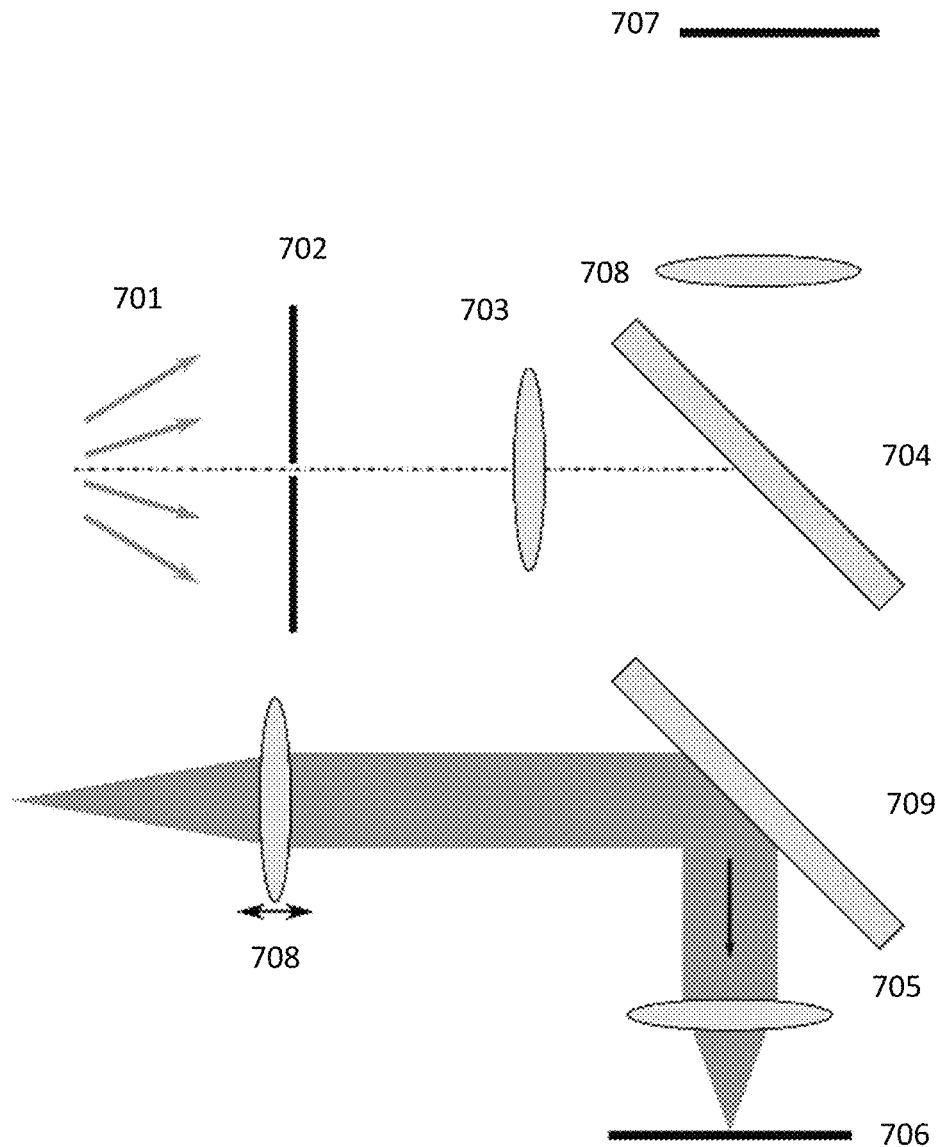
FIG. 7—A schematic of the process of bringing the focus of laser radiation into a confocal position with the autofocus component and autofocus sensor during the production of an apparatus of the invention comprising an autofocus system and a laser based sampling and ionisation system according to embodiments of the present invention.

Thus key to the functioning of the autofocus system is ensuring that the autofocus component and the autofocus sensor are confocal. This process is typically performed when the system is manufactured, for example by translation of the autofocus component in the axis of the illumination radiation, as illustrated in FIG. 6 (components of FIG. 6 correspond to those of preceding figures, simply with the first digit of the component number changed to match the figure number; here the translatable autofocus component is 602). The system also comprises a laser collimating lens (609) and a further beam splitter (610) for directing laser radiation onto the sample. As shown in FIG. 7, when the apparatus comprising the autofocus system also comprises a sampling and ionisation system comprising a laser that impinges upon the sample, the ablation laser is also focused to the same focal plane as the autofocus component and the autofocus sensor by axial translation of the collimating lens (709) The laser will be understood to be of sharp focus in the focal plane of the autofocus system based on observation of the ablation spot size and shape observed. The objective lens used to focus the illumination radiation onto the sample is also used to focus the laser radiation for laser ablation onto the sample.

Figure 12:
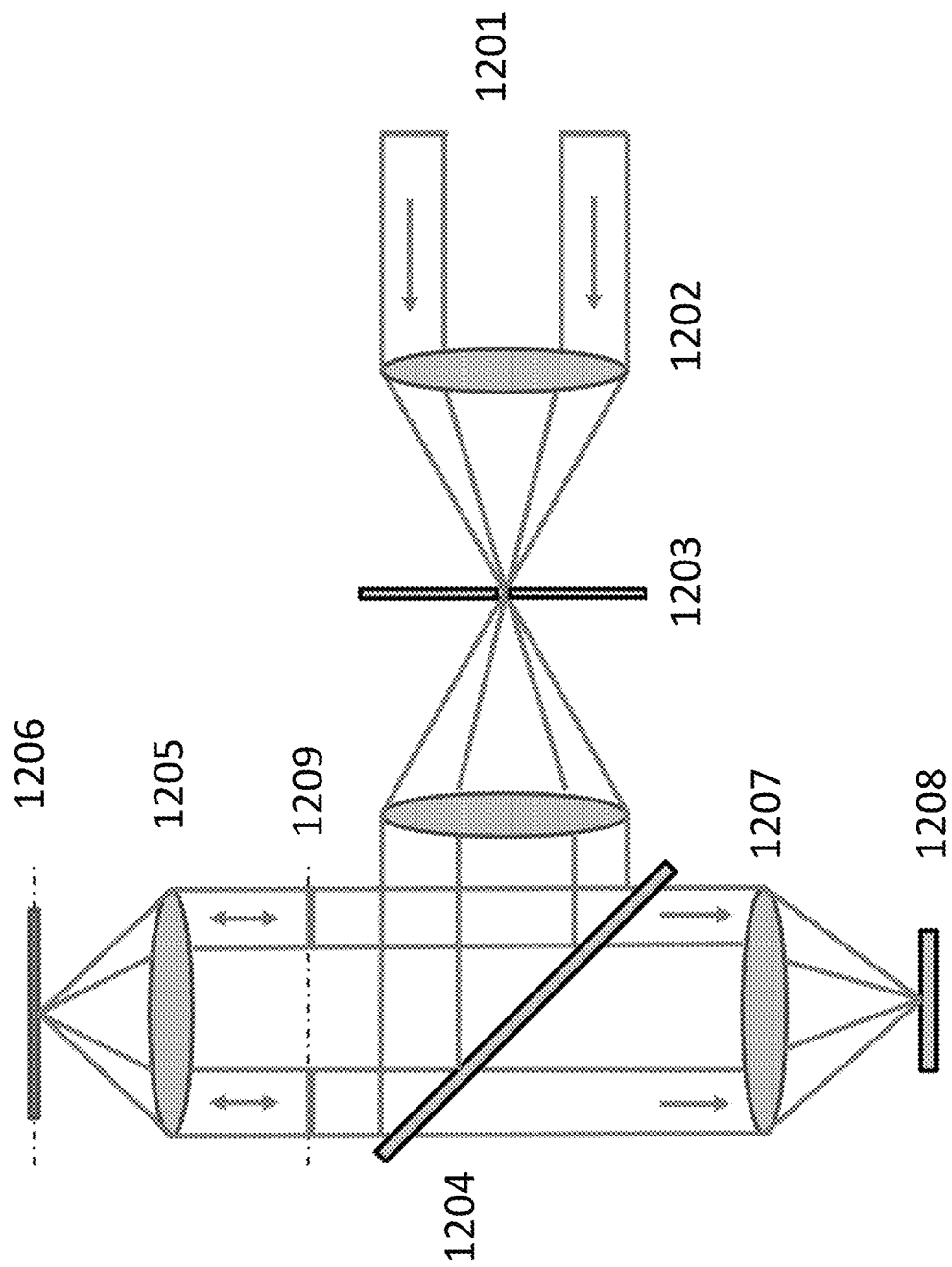
FIG. 12—Schematic of the autofocus setup according to embodiments of the present invention. Two light sources are used, and their light is guided through a small aperture in focus with the objective focal plane. If the sample is defocused the camera will observe the image from each LED to become blurry as well as offset in accordance with each LED's illumination angle at the sample.

Aspects include autofocus systems and methods may combine benefits of multiple autofocus methods (often used for whole slide imaging) to achieve fast, reliable, and accurate autofocusing over a broad range of initial sample positions for imaging mass cytometry. For example, an autofocus method and/or system may combine two separate techniques such as projection of an aperture onto the sample plane, where the aperture is aligned a priori to be in perfect focus when the sample is likewise in perfect focus, and illumination of this aperture with two separately controllable light sources with a relatively small solid angle. An example is shown in FIG. 12, which provides a schematic of the autofocus setup. Two light sources are used, and their light is guided through a small aperture in focus with the objective focal plane. If the sample is defocused the camera will observe the image from each LED to become blurry as well as offset in accordance with each LED's illumination angle at the sample.

As shown in FIG. 12, a sample 1206 may be positioned near an objective focal plane. Two light sources (e.g., LEDs 1201) may be focused by a condenser lens through an aperture and onto an be directed (e.g., by one or more mirrors 1204 and/or objectives 1205 onto the sample. Light reflected from the sample may impinge on an image sensor 1208, e.g., after passing through a tube lens 1207. Element 1209 marks the objective back focal plane with image of light sources.

Each of the two light sources is turned on in sequence and an image is acquired with the camera for each LED. If the sample is not in perfect focus, the two images will appear similarly blurred, but offset from each other in the direction of the illumination angle (see FIG. 13). The correlation between these two frames can be calculated rapidly using FFTs, and this function will be maximal at some pixel offset. This pixel offset is directly proportional to the distance the sample is from focus, and the proportionality can be calibrated straightforwardly using encoders on the translation stage along the focus direction, which are already present. Therefore, the autofocus mechanism, in principle, requires only the acquisition of two camera frames to determine the optimal focus position of the sample, which is orders of magnitude faster than our current implementation.

Figure 13:
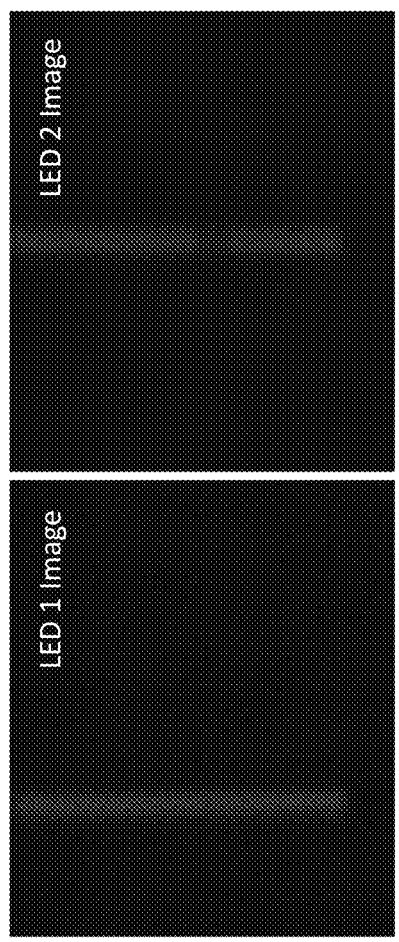
FIG. 13—Top: Acquired LED images at a defocus distance of +60 µm according to embodiments of the present invention. The two images are similarly blurred and offset along the directions of illumination for each LED. Bottom: calculated correlation function between the two images. Parabolic peak fitting gives a peak position of −512.08 pixels, which corresponds to a focus offset of +60 µm.
Figure 13:
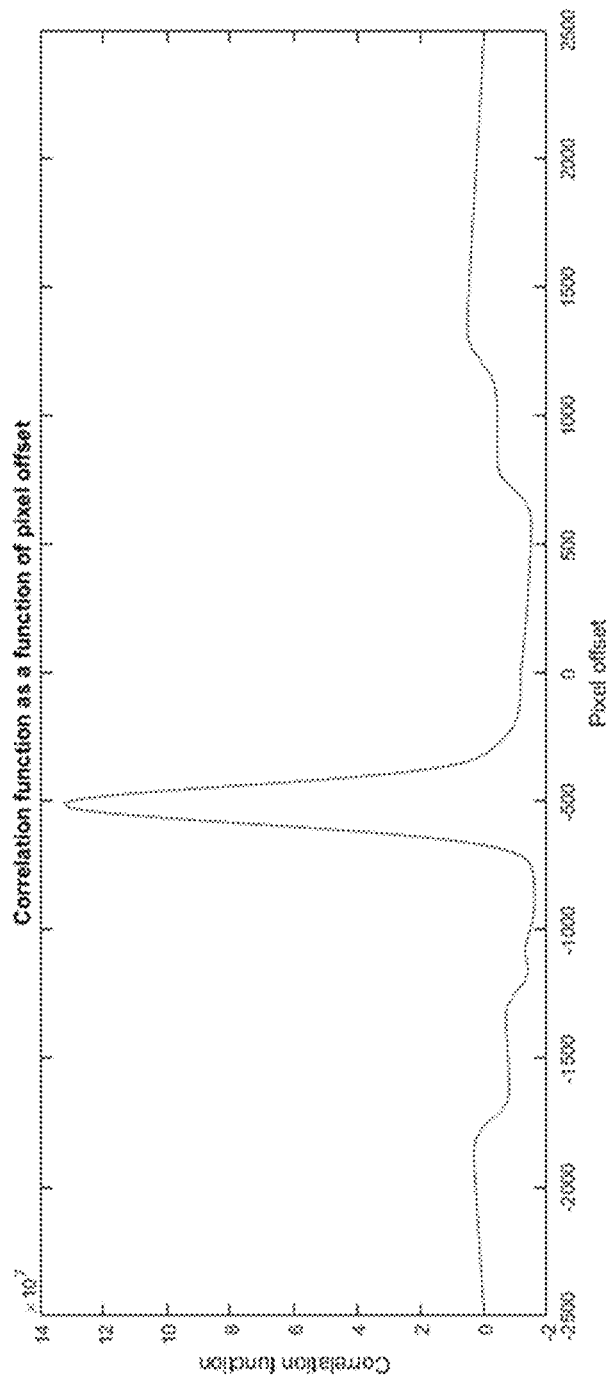

We envision that there may be many aperture shapes and sizes that could be used. One straightforward and robust shape is expected to be a narrow slit, oriented with its small opening along the translation direction, as shown in FIG. 13. Of note, a small round or rectangular aperture could also be used. Multiple apertures (slits, circles, or otherwise) could be used. An 'inverted aperture' could be used, meaning a small obscuration that would lead to a darkening of the image in some region, which means the sample structure would be retained in the focus image, such that it can be used for defocus determination as well. Furthermore, the aperture may be defocused with respect to perfect sample focus in order to create a non-zero target offset between the two LED images. Finally, the two LEDs do not need to have the same colour. Using two differently coloured LEDs allows for single-frame acquisition of the focus data by using a single colour camera, or perhaps by using appropriate filters to project the two colours onto different areas of one monochrome camera. Of note, laser diodes may be used in place of LEDs (or LEDs combined with apertures).

FIG. 13 Top: Acquired LED images at a defocus distance of +60 μm. The two images are similarly blurred and offset along the directions of illumination for each LED. Bottom: calculated correlation function between the two images. Parabolic peak fitting gives a peak position of −512.08 pixels, which corresponds to a focus offset of +60 μm.

In practice, the algorithm could sacrifice some of its speed to improve robustness by taking iterative steps toward best focus. For example, a step of 95% of the extracted defocus value could be taken, and the autofocus method repeated. Subsequent repetitions should converge very rapidly to the correct focus position.

Essential to the high-speed operation of this autofocus method is to trigger the acquisition of frames on the camera using an electronic trigger, as opposed to using the camera in a free-running mode. This can be accomplished using standard industrial vision cameras, which often have asynchronous triggering as part of their feature set.

A side benefit of using hardware triggering of the camera is that it benefits several other IMC functionalities as well, most notably panorama acquisition. The current implementation of panorama acquisition (using a free-running camera) is referred to as 'stop-and-stare', where the stage is moved to each successive target position and waits for the next frame from the camera to arrive before moving on. Using hardware camera triggering, either based on target stage positions or together with high-speed registration of the stage position, as well as intense LED illumination (allowing for short integration time on the camera), the stage can be kept in continuous motion while the camera frames are acquired at specific positions along the motion profile. This leads to a significant speed-up in the acquisition of panoramas in IMC.

When the laser, autofocus component and autofocus sensor are all confocal, then during use of the apparatus the laser can be brought into focus by moving the sample into focus, by moving it to the point at which the reflected illumination radiation at the autofocus sensor is in focus. Thus the autofocus system can focus both optical imaging components/systems and the ionisation and sampling system.

Methods for Autofocusing

A variety of autofocusing methods are described herein, including any method of using an autofocus system described herein.

In certain aspects, autofocusing is based on the position of one or more spots or lines impinging an autofocus sensor. The autofocus system may not require a pre-calibrated coordinate (e.g., of best focus) at one or more spots or lines impinging the autofocus sensor. Alternatively, the autofocus system may be pre-calibrated such that a feature is coincident upon a known coordinate on the autofocus sensor at best focus.

Autofocusing may be based on alignment of features (spots or lines) detected by the autofocus sensor. For example, autofocusing (e.g., autofocus correction) may be based on an offset between spots or lines impinging the autofocus sensor. Autofocusing is based on coincidence of features on the autofocus sensor, such that autofocusing correction is repeated until the features are coincident. Alternating LEDs and/or laser diodes that provide separate features may allow for improved accuracy compared to constant radiation from such LEDs and/or laser diodes (for example, slight shifts in position between the features may only be apparent when they are detected separately).

In certain embodiments, a plurality of apertures may provide multiple features from a single LED. Autofocusing may then be based on the number of spots detected by the autofocus sensor and/or the uniformity of spots detected by the autofocus sensor.

Autofocusing can be achieved by a number of types of method. For instance, on one hand, it can be achieved retroactive determination. In broad terms, this type of method works by scanning the sample through a range of positions, in a relatively coarse manner with large distances between the positions, and picking the position which is closest to the focal plane of the autofocusing system (i.e. which has the highest focus score). Once the position which is closest has been determined, further refinement about that position can be performed, by again moving the sample through a series of positions, wherein the positions are much closer together in the refinement step in comparison to the prior coarser step. From these positions the closest to the focal plane is picked (again the position with the highest focus score). Thus this first kind of method relies on scanning through a range of sample positions, and retroactively picking the best position.

Thus the invention provides an autofocusing method comprising
    determining the focus score of a first position of a sample,
    moving the sample to a second position,
    determining the focus score of the second position, and
    comparing the focus scores to each other,
    wherein the step of determining the focus score comprises illuminating a sample with radiation from an illumination source, the illumination radiation being passed through an autofocus component comprising multiple apertures, and detecting illumination radiation reflected from the sample with an autofocus sensor (such as wherein detecting illumination radiation reflected from the sample comprises detecting radiation at known positions (also called regions of interest) on the autofocus sensor), and
    wherein moving the sample is movement parallel to the axis in which the illumination radiation is directed onto the sample (i.e. movement is in the z-axis).

As noted above, in some embodiments of the method of the invention, the sample is moved to a number of positions. Accordingly, sometimes the method further comprises, before the step of comparing the focus score of the first position to the focus score of the second position, moving the sample to at least a third position and determining a focus score at least the third position. Here, therefore, the step of comparing the focus score of the first position to the focus score of the second position also encompasses a comparison of the third focus score to the first and second focus scores. In some instances, the method comprises, prior to the step of comparing the focus score of the first position to the focus score of the second position, moving the sample to, and determining a focus score at, at least a 4th, 5th, 6th, 7th, 8th, 9th, 10th, 15th, 20th, 25th, 50th, 100th, 250th, 500th or 1000th position. Here, therefore, the step of comparing the focus score of the first position to the focus score of the second position also encompasses a comparison of the 4th, 5th, 6th, 7th, 8th, 9th, 10th, 15th, 20th, 25th, 50th, 100th, 250th, 500th or 1000th position to the other determined focus scores.

Thus the method autofocusses by retroactively searching for the highest focus score. The focus score is a parameter that can be determined in a number of ways. For instance the intensity of reflected illumination radiation detected from the plurality of apertures can be summed to produce the focus score. Alternatively, the focus score can be calculated by measuring how defocused the reflected illumination radiation is (e.g. total number of pixels on the sensor which are detecting reflected illumination radiation at and around the areas at which reflected illumination radiation would be expected to impinge upon the autofocus sensor when the sample is in focus, i.e. around the expected regions of interest).

In some embodiments, following the step of comparing the focus scores to each other, the sample stage is moved to a first round optimum focal position, which is the position with the highest focus score. If saturation of any pixels on the autofocus sensor is detected, the illumination source intensity is decreased, and the method repeated.

As noted above, in some instances, the method comprises a first coarse estimate of the focal position followed by one or more further rounds which refine the position of the sample to bring it closer to the focal plane. Accordingly, in some embodiments, the method further comprises repeating the method at a second set of positions centred around the first round optimal position determined in the first round. As it is a refinement, the distance between the positions in the second set is shorter than the distance between positions used to calculate the first round optimum focal position. Sometimes, the distance between the positions is, or is shorter than, the distance between positions used to calculate the first round optimum focal position divided by the number of positions in the second set of positions. The focus scores are then compared to generate a second round optimum focal position. In some embodiments, the second round optimum focal position is simply the second round position with the highest focus score, and the sample moved to this position (i.e. as done in the movement following the first round). However, in some embodiments, the step of comparing the second round focus scores to each other comprises the step of fitting a parabola to the focus scores at each position and calculating the position where the derivative of the curve is zero as the second round optimal focus position. The sample stage can then be moved to the second round optimum focal position determined by parabola fitting.

In some embodiments, the step of comparing focus scores to each other comprises the step of fitting a parabola to the focus scores at each position and calculating the position where the derivative of the curve is zero as the first round optimal focus position. The sample stage can then be moved to the first round optimum focal position. This method can then be repeated at a second set of positions centred around the position determined in to be the first round optimum focal position, wherein the distance between the positions in the second set is shorter than the distance between positions used to calculate the first optimum focal position. Sometimes, the distance between the positions is, or is shorter than, the distance between positions used to calculate the first round optimum focal position divided by the number of positions in the second set of positions, to generate a second round optimum focal position. Accordingly, in some embodiments, generating a second round optimum focal position, comprises the step of comparing the second round focus scores to each other comprises the step of fitting a parabola to the focus scores at each position and calculating the position where the derivative of the curve is zero as the second round optimal focus position. The sample stage can then be moved to the second round optimum focal position determined by parabola fitting.

The invention also provides methods of autofocusing, comprising iteratively repeating the methods described above.

Alternatively, the sample can be brought into focus using a converging algorithm in an iterative procedure, whereby the reflected illumination radiation detected at any position is informative as to the relative positions of the sample and the focal plane. Accordingly, this kind of method operates by determining the reading of a position, calculating the direction in which the sample should be moved in order to move the sample toward the focal plane, and in some instances an estimate of the distance. The sample is then moved and a further reading determined. The process is then iteratively repeated to home in on the focal plane.

The invention also provides an autofocusing method comprising
  determining the direction of focus at a position n of a sample,
  moving the sample in the direction of focus to position (n+1),
  wherein determining the direction of focus comprises illuminating a sample with radiation from an illumination source, the illumination radiation being passed through an autofocus component comprising multiple apertures, wherein at least two of the apertures of the autofocus component are offset in the axis at which the illumination radiation passes through the autofocus component, and detecting illumination radiation reflected from the sample with an autofocus sensor (such as wherein detecting illumination radiation reflected from the sample comprises detecting radiation at known positions (also called regions of interest) on the autofocus sensor), and
  wherein moving the sample is movement parallel to the axis in which the illumination radiation is directed onto the sample (i.e. movement is in the z-axis).

In some embodiments, the method comprises repeating the method of the previous paragraph, at least 1 further time, such as at least 2, at least 3, at least 4, at least 5, at least 6, at least 7, at least 8, at least 9, at least 10, at least 20, or at least 50 times.

In some embodiments, the step of determining the direction of focus at position n comprises comparing how defocused the reflected illumination radiation from the at least two offset apertures is when it impinges on the autofocus sensor.

Sample Topology Mapping Methods

Figure 11:
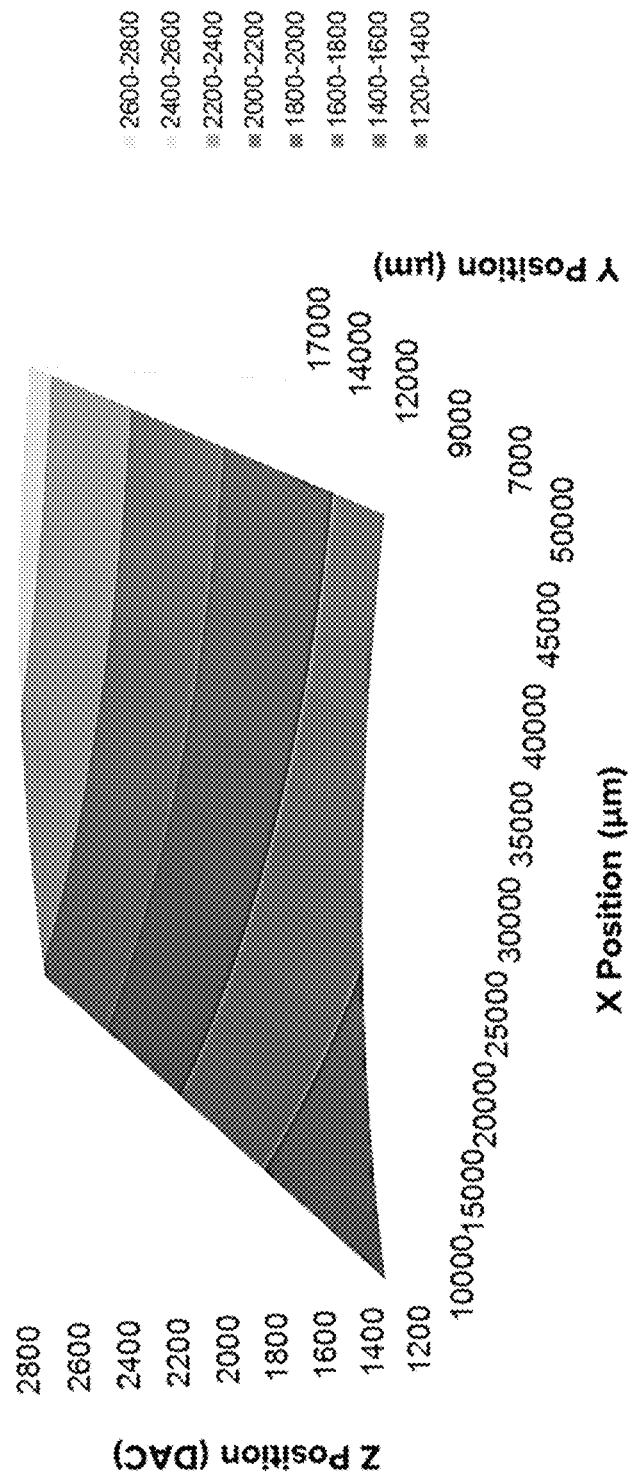
FIG. 11—Plot of Z-profile of a sample generated using the sample topology mapping method of embodiments of the present invention. The plot is shaded to illustrate the Z position at optimum focus, with numerical ranges for each shade provided to the right of the graph. In this example, an increase in the X or Y coordinate correspond to an increase in this Z position.

The invention also provides a method of mapping the topology of a sample surface comprising, performing an autofocusing method, moving the sample in the plane of the sample (i.e. in the X and/or Y axis) to a second position in the plane of the sample, and performing the autofocusing method of the invention, again to record the optimum focal position at the second position in the plane of the sample. In some embodiments, the autofocusing method is an autofocusing method of the invention. In some embodiments, the method further comprises moving the sample in the plane of the sample to one or more further positions, such as at least a 3rd, 4th, 5th, 6th, 7th, 8th, 9th, 10th, 15th, 20th, 25th, 50th, 100th, 250th, 500th or 1000th position in the plane of the sample, and recording the optimum focal position at each of those positions. Sometimes, the method further comprising plotting the optimum focal position at each of the positions in the plane of the sample. Sometimes, the method further comprises interpolating between the optimum focal position at each of the positions in the plane of the sample to produce a surface representation of the sample. FIG. 11 provides a plot of the surface of a sample according to this method of the invention. In some embodiments, the interpolation is polynomial interpolation, spline interpolation or interpolation via Gaussian processes.

In certain aspects, the method may include creating a focal map of best focus across X, Y, or X-Y coordinates.

Methods of Sampling Comprising Use of an Autofocus System

As noted above, the autofocusing system can be used to bring the sample into optimum focal position for sampling, for instance when the system is in an apparatus of the invention.

A method of autofocusing using the apparatus of any of the above embodiments may further include sampling. For example, a method of autofocusing may include autofocusing a laser for ablating sample material, and may include analysis of sample material (e.g., by ICP-MS). The sample material may include mass tags.

Thus, the invention provides a method of analysing a sample, such as a biological sample, comprising:
  performing an autofocusing method of the invention to place the sample at the focus point of a sampling and ionisation system;
  determining the elemental composition of the sample, for instance by imaging mass cytometry or imaging mass spectrometry.

The invention also provides a method of analysing a sample comprising:

performing an autofocusing method of the invention to place the sample, such as a biological sample, at the focus point of a sampling and ionisation system;

performing sampling and ionization of the sample on a sample stage at multiple locations; and detecting the ions from locations on the sample, whereby detection of the ions permits construction of an image of the sample, optionally wherein the multiple locations are multiple known locations.

Thus, more specifically the invention provides a method of analysing a sample comprising:

performing an autofocusing method of the invention to place the sample at the focus point of a sampling laser for laser ablation;

performing laser ablation of the sample on a sample stage at multiple locations; and subjecting the plumes to ionisation and mass spectrometry, whereby detection of atoms in the plumes permits construction of an image of the sample, optionally wherein the multiple locations are multiple known locations.

In imaging mass cytometry, the sample is labelled before analysis. Accordingly, the invention also provides a method of performing mass cytometry on a sample comprising a plurality of cells, the method comprising:

labelling a plurality of different target molecules in the sample with one or more different labelling atoms, to provide a labelled sample;

performing an autofocusing method of the invention to place the sample at the focus point of a sampling laser for laser ablation;

performing laser ablation of the sample on a sample stage at multiple locations; and subjecting the plumes to ionisation and mass spectrometry, whereby detection of atoms in the plumes permits construction of an image of the sample, optionally wherein the multiple locations are multiple known locations.

As understood by one of skill in the art, laser ablation in these method is achieved by directing laser radiation to the sample. In some embodiments, at each position, multiple laser shots are fired at the sample, and after each shot at the position the sample on the sample stage is moved in the Z axis toward the focus point of the laser to affect the depth of the sample ablated at the position. In some embodiments, the starting position in the Z axis for ablation of the sample is the optimum focus position at that position on the sample determined by sample topology mapping method of the invention and wherein each plume generated from each shot at a position in the Z axis at the position on the sample, is detected individually, such as permits construction of a 3D image of the sample.

In some embodiments, the method comprising using an autofocus component of the invention.

In some embodiments, the method comprising using an autofocus system of the invention.

In some embodiments, the method comprising using an apparatus of the invention.

Additional Aspects of Methods

Prior to autofocusing and/or sampling based on autofocusing, methods of the subject application may include providing a labelled biological sample. In certain aspects, a method may include labelling the biological sample. The biological sample may be labelled with a labelling atom conjugated to a specific binding pair (SBP) member as described herein. For example, the SBP member may include an antibody and/or the labelling atom may include a metal tag (such as an enriched metal isotope). Suitable samples, labelling atoms, SBP members, and methods of labelling are described further herein.

Considerations in Autofocus System

A valuable function of the imaging mass cytometry system is the ability to perform automatic focusing of the sample in the camera view. Major performance characteristics for an autofocusing system are the average time needed to perform autofocusing, the robustness/reliability of the system across a variety of samples, and the focusing range over which the autofocusing system will produce reliable results. Most autofocusing systems currently available (including the autofocusing system implemented in the first-generation IMC) suffer from poor performance in at least one of these three requirements.

For example, an IMC autofocusing system using a plurality of apertures and a single LED source is robust and generally reliable, and it is able to find the optimal focus over a long translation range, but it may be slow (e.g., on the scale of milliseconds). This may not be an issue when the rate of laser ablation and mass analysis is comparable.

Many after-market commercial systems suffer from the opposite limitations: they are fast and mostly robust (except for some immersion-type samples), but only work when the sample is already relatively close to optimal focus, and can suffer from focus drift over the life of the device.

Autofocusing systems may be categorized into two major types: hardware-based or image analysis-based. The latter category analyses the current image of the sample in terms of sharpness, contrast, etc., and attempts to maximize those characteristics by moving the sample. Such systems tend to work quite well for a subset of samples, but cannot work with samples that intrinsically lack contrast. Furthermore, the range over which the autofocusing method works is limited, and the system will need to 'hunt' to find optimal focus. Overall, this type of autofocusing can be quite fast, but is generally not reliable enough for unsupervised application in IMC.

Hardware-based autofocusing systems (in particular aftermarket solutions aimed at standard microscopes) often project an illuminated aperture onto the sample using invisible light, with the illumination coming from only one side of the back aperture of the microscope objective. The effect of this one-sided illumination is that in the image plane of the objective the aperture will move from side to side (in addition to becoming defocused) as the sample is moved through focus. A position-sensitive detector is used to quantify this lateral shift, and in this way the optimal focus position can be maintained. The range over which this method works method quite limited, and so the application of this method is usually in keeping a sample in focus rather than finding the optimal focus in the first place. This is exacerbated by the fact that these autofocus methods have trouble keeping calibration over time, temperature and for various samples and objectives. Second, the structure of the sample may have an impact on the image observed in the image plane of the objective. Therefore, the output of the detector when the sample is in perfect focus is not the same for all samples. Again this limits the application of these systems to 'locking in' to a particular focus position, and only observing one area of one sample over a long time.

In certain aspects, an autofocusing system or method may provide rapid autofocusing independent of sample surface quality, and may perform on-the-fly corrections to focus quality, which could mitigate the effect of sample tilt, stage flatness issues, and/or sample surface topology.

In certain aspects, the light from the LEDs may be sent through an aperture and then into the objective itself (epi-illumination). The use of an aperture may improve performance of the system by producing sharp images with high contrast when the system is in-focus.

1. Sampling and Ionisation Systems

Sampling of the sample involves removing material from the sample by a beam of particles (e.g. photons) that are focused on the sample and excite the sample, such that material is moved from it. The focus of the beam of particles (e.g. photons) is confocal with the autofocus system described in the previous section, and accordingly when the autofocus system brings the sample into focus, the sample is placed in an optimum position for sample.

As such, an apparatus of the subject application may include a sampling system (such as a laser ablation sampling system), an ionisation system (such as an ICP system), or both. For example, the apparatus may include an autofocus system, movable sample stage, and laser ablation sampling system, which may be coupled to a mass spectrometer such as an ICP-MS system. In certain cases, such an apparatus may further include the ICP-MS system.

In certain aspects, the sampling system is a laser ablation sampling system. The apparatus may further include an ionisation system, such as an ICP ionisation system coupled to the laser ablation sampling system by a gas conduit. The apparatus may further include a mass spectrometer. The mass spectrometer may be configured to simultaneously detect a plurality of mass tags.

a. Laser Ablation Sampling and Ionising System

A laser ablation based analyser typically comprises three components. The first is a laser ablation sampling system for the generation of plumes of vaporous and particulate material from the sample for analysis. Before the atoms in the plumes of ablated sample material (including any detectable labelling atoms as discussed below) can be detected by the detector system—a mass spectrometer component (MS component; the third component), the sample must be ionised (and atomised). Accordingly, the apparatus comprises a second component which is an ionisation system that ionises the atoms to form elemental ions to enable their detection by the MS component based on mass/charge ratio (some ionisation of the sample material may occur at the point of ablation, but space charge effects result in the almost immediate neutralisation of the charges). The laser ablation sampling system is connected to the ionisation system by a transfer conduit.

Laser Ablation Sampling System

In brief summary, the components of a laser ablation sampling system include a laser source that emits a beam of laser radiation that is directed upon a sample. The sample is positioned on a stage within a chamber in the laser ablation sampling system (the sample chamber). The stage is usually a translation stage, so that the sample can be moved relative to the beam of laser radiation, whereby different locations on the sample can be sampled for analysis. As discussed below in more detail, gas is flowed through the sample chamber, and the flow of gas carries away the plumes of aerosolised material generated when the laser source ablates the sample, for analysis and construction of an image of the sample based on its elemental composition (including labelling atoms such as labelling atoms from elemental tags). As explained further below, in an alternative mode of action, the laser system of the laser ablation sampling system can also be used to desorb material from the sample.

For biological samples (cells, tissues sections etc.) in particular, the sample is often heterogeneous (although heterogeneous samples are known in other fields of application of the disclosure, i.e. samples of a non-biological nature). A heterogeneous sample is a sample containing regions composed of different materials, and so some regions of the sample can ablate at lower threshold fluence at a given wavelength than the others. The factors that affect ablation thresholds are the absorbance coefficient of the material and mechanical strength of material. For biological tissues, the absorbance coefficient will have a dominant effect as it can vary with the laser radiation wavelength by several orders of magnitude. For instance, in a biological sample, when utilising nanosecond laser pulses a region that contains proteinaceous material will absorb more readily in the 200-230 nm wavelength range, while a region containing predominantly DNA will absorb more readily in the 260-280 nm wavelength range.

It is possible to conduct laser ablation at a fluence near the ablation threshold of the sample material. Ablating in this manner often improves aerosol formation which in turn can help improve the quality of the data following analysis. Often to obtain the smallest crater, to maximise the resolution of the resulting image, a Gaussian beam is employed. A cross section across a Gaussian beam records an energy density profile that has a Gaussian distribution. In that case, the fluence of the beam changes with the distance from the centre. As a result, the diameter of the ablation spot size is a function of two parameters: (i) the Gaussian beam waist ($1/e^2$), and (ii) the ratio between the fluence applied and the threshold fluence.

Thus, in order to ensure consistent removal of a reproducible quantity of material with each ablative laser pulse, and thus maximise the quality of the imaging data, it is useful to maintain a consistent ablation diameter which in turn means adjusting the ratio of the energy supplied by the laser pulse to the target to the ablation threshold energy of the material being ablated. This requirement represents a problem when ablating a heterogeneous sample where the threshold ablation energy varies across the sample, such as a biological tissue where the ratio of DNA and protein material varies, or in a geological sample, where it varies with the particular composition of the mineral in the region of the sample. To address this, more than one wavelength of laser radiation can be focused onto the same ablation location on a sample, to more effectively ablate the sample based on the composition of the sample at that location.

Laser System of the Laser Ablation Sampling System

The laser system can be set up to produce single or multiple (i.e. two or more) wavelengths of laser radiation. Typically, the wavelengths of laser radiation discussed refer to the wavelength which has the highest intensity (the "peak" wavelength). If the system produces different wavelengths, they can be used for different purposes, for example, for targeting different materials in a sample (by targeting here is meant that the wavelength chosen is one which is absorbed well by a material).

Where multiple wavelengths are used, at least two of the two or more wavelengths of the laser radiation can be discrete wavelengths. Thus when a first laser source emits a first wavelength of radiation that is discrete from a second wavelength of radiation, it means that no, or a very low level of radiation of the second wavelength is produced by the first laser source in a pulse of the first wavelength, for example, less than 10% of the intensity at the first wavelength, such as less than 5%, less than 4%, less than 3%, less than 2%, or less than 1%. Typically, when different wavelengths of laser radiation are produced by harmonics generation, or other non-linear frequency conversion processes, then when a specific wavelength is referred to herein, it will be understood by the skilled person that there will be some degree of variation about the specified wavelength in the spectrum produced by the laser. For example, a reference to X nm encompasses a laser producing a spectrum in the range X±10 nm, such as X±5 nm, for example X±3 nm.

Lasers

Generally, the choice of wavelength and power of the laser used for ablation of the sample can follow normal usage in cellular analysis. The laser must have sufficient fluence to cause ablation to a desired depth, without substantially ablating the sample carrier. A laser fluence of between 0.1-5 J/cm$^2$ is typically suitable e.g. from 3-4 J/cm$^2$ or about 3.5 J/cm$^2$, and the laser will ideally be able to generate a pulse with this fluence at a rate of 200 Hz or greater. In some instances, a single laser pulse from such a laser should be sufficient to ablate cellular material for analysis, such that the laser pulse frequency matches the frequency with which ablation plumes are generated. In general, to be a laser useful for imaging biological samples, the laser should produce a pulse with duration below 100 ns (preferably below 1 ns) which can be focused to, for example, the specific spot sizes discussed herein. In some embodiments of the present invention, the ablation rate (i.e. the rate at which the laser ablates a spot on the surface of the sample) is 200 Hz or greater, such as 500 Hz or greater, 750 Hz or greater, 1 kHz or greater, 1.5 kHz or greater, 2 kHz or greater, 2.5 kHz or greater, 3 kHz or greater, 3.5 kHz or greater, 4 kHz or greater, 4.5 kHz or greater, 5 kHz or greater, 10 kHz or greater, 100 kHz or greater, 1 MHz or greater, 10 MHz or greater, or 100 MHz or greater. Many lasers have a repetition rate in excess of the laser ablation frequency, and so appropriate components, such as pulse pickers etc. can be employed to control the rate of ablation as appropriate. Accordingly, in some embodiments, the laser repetition rate is at least 1 kHz, such as at least 10 kHz, at least 100 kHz, at least 1 MHz, at least 10 MHz, around 80 MHz, or at least 100 MHz, optionally wherein the sampling system further comprises a pulse picker, such as wherein the pulse picker is controlled by the control module that also controls the movement of the sample stage and/or the positioner(s). In other instances, multiple closely spaced pulse bursts (for example a train of 3 closely spaced pulses) can be used to ablate one single spot. As an example a 10×10 μm area may be ablated by using 100 bursts of 3 closely spaced pulses in each spot; this can be useful for lasers which have limited ablation depth, for example femtosecond lasers, and can generate a continuous plume of ablated cellular material without losing resolution.

For instance, the frequency of ablation by the laser system is within the range 200 Hz-100 MHz, 200 Hz-10 MHz, 200 Hz-1 MHz, 200 Hz-100 kHz, within the range 500-50 kHz, or within the range 1 kHz-10 kHz.

At these frequencies the instrumentation must be able to analyse the ablated material rapidly enough to avoid substantial signal overlap between consecutive ablations, if it is desired to resolve each ablated plume individually (which as set out below may not necessarily be desired when firing a burst of pulses at a sample). It is preferred that the overlap between signals originating from consecutive plumes is <10% in intensity, more preferably <5%, and ideally <2%. The time required for analysis of a plume will depend on the washout time of the sample chamber (see sample chamber section below), the transit time of the plume aerosol to and through the laser ionisation system, and the time taken to analyse the ionised material. Each laser pulse can be correlated to a pixel on the image of the sample that is subsequently built up, as discussed in more detail below.

In some embodiments, the laser source comprises a laser with a nanosecond pulse duration or an ultrafast laser (pulse duration of 1 ps ($10^{-12}$ s) or quicker, such as a femtosecond laser. Ultrafast pulse durations provide a number of advantages, because they limit heat diffusion from the ablated zone, and thereby provide more precise and reliable ablation craters, as well as minimising scattering of debris from each ablation event.

In some instances a femtosecond laser is used as the laser source. A femtosecond laser is a laser which emits optical pulses with a duration below 1 ps. The generation of such short pulses often employs the technique of passive mode locking. Femtosecond lasers can be generated using a number of types of laser. Typical durations between 30 fs and 30 ps can be achieved using passively mode-locked solid-state bulk lasers. Similarly, various diode-pumped lasers, e.g. based on neodymium-doped or ytterbium-doped gain media, operate in this regime. Titanium-sapphire lasers with advanced dispersion compensation are even suitable for pulse durations below 10 fs, in extreme cases down to approximately 5 fs. The pulse repetition rate is in most cases between 10 MHz and 500 MHz, though there are low repetition rate versions with repetition rates of a few megahertz for higher pulse energies (available from e.g. Lumentum (CA, USA), Radiantis (Spain), Coherent (CA, USA)). This type of laser can come with an amplifier system which increases the pulse energy There are also various types of ultrafast fiber lasers, which are also in most cases passively mode-locked, typically offering pulse durations between 50 and 500 fs, and repetition rates between 10 and 100 MHz. Such lasers are commercially available from e.g. NKT Photonics (Denmark; formerly Fianium), Amplitude Systems (France), Laser-Femto (CA, USA). The pulse energy of this type of laser can also be increased by an amplifier, often in the form of an integrated fiber amplifier.

Some mode-locked diode lasers can generate pulses with femtosecond durations. Directly at the laser output, the pulse duration is usually around several hundred femtoseconds (available e.g. from Coherent (CA, USA)).

In some instances, a picosecond laser is used. Many of the types of lasers already discussed in the preceding paragraphs can also be adapted to produce pulses of picosecond range duration. The most common sources are actively or passively mode-locked solid-state bulk lasers, for example a passively mode-locked Nd-doped YAG, glass or vanadate laser. Likewise, picosecond mode-locked lasers and laser diodes are commercially available (e.g. NKT Photonics (Denmark), EKSPLA (Lithuania)).

Nanosecond pulse duration lasers (gain switched and Q switched) can also find utility in particular apparatus set ups (Coherent (CA, USA), Thorlabs (NJ, USA)), Alternatively, a continuous wave laser may be used, externally modulated to produce nanosecond or shorter duration pulses.

Typically, the laser beam used for ablation in the laser systems discussed herein has a spot size, i.e., at the sampling location, of 100 μm or less, such as 50 μm or less, 25 μm or less, 20 μm or less, 15 μm or less, or 10 μm or less, such as about 3 μm or less, about 2 μm or less, about 1 μm or less, about 500 nm or less, about 250 nm or less. The distance referred to as spot size corresponds to the longest internal dimension of the beam, e.g. for a circular beam it is the beam diameter, for a square beam it corresponds to the length of the diagonal between opposed corners, for a quadrilateral it is the length of the longest diagonal etc. (as noted above, the diameter of a circular beam with a Gaussian distribution is defined as the distance between the points at which the fluence has decreased to $1/e^2$ times the peak fluence). As an alternative to the Gaussian beam, beam shaping and beam masking can be employed to provide the desired ablation spot. For example, in some applications, a square ablation spot with a top hat energy distribution can be useful (i.e. a beam with near uniform fluence as opposed to a Gaussian energy distribution). This arrangement reduces the dependence of the ablation spot size on the ratio between the fluence at the peak of the Gaussian energy distribution and the threshold fluence. Ablation at close to the threshold fluence provides more reliable ablation crater generation and controls debris generation. Accordingly, the laser system may comprise beam masking and/or beam shaping components, such as a diffractive optical element, arranged in a Gaussian beam to re-shame the beam and produce a laser focal spot of uniform or near-uniform fluence, such as a fluence that varies across the beam by less than ±25%, such as less than ±20%, ±15%, ±10% or less than ±5%. Sometimes, the laser beam has a square cross-sectional shape. Sometimes, the beam has a top hat energy distribution.

When used for analysis of biological samples, in order to analyse individual cells the spot size of laser beam used will depend on the size and spacing of the cells. For example, where the cells are tightly packed against one another (such as in a tissue section) one or more laser sources in the laser system can have a spot size which is no larger than these cells. This size will depend on the particular cells in a sample, but in general the laser spot will have a diameter of less than 4 µm e.g. about 3 µm or less, about 2 µm or less, about 1 µm or less, about 500 nm or less, about 250 nm or less, or between 300 nm and 1 µm. In order to analyse given cells at a subcellular resolution the system uses a laser spot size which is no larger than these cells, and more specifically uses a laser spot size which can ablate material with a subcellular resolution. Sometimes, single cell analysis can be performed using a spot size larger than the size of the cell, for example where cells are spread out on the slide, with space between the cells. Here, a larger spot size can be used and single cell characterisation achieved, because the additional ablated area around the cell of interest does not comprise additional cells. The particular spot size used can therefore be selected appropriately dependent upon the size of the cells being analysed. In biological samples, the cells will rarely all be of the same size, and so if subcellular resolution imaging is desired, the ablation spot size should be smaller than the smallest cell, if constant spot size is maintained throughout the ablation procedure. Small spot sizes can be achieved using focusing of laser beams. A laser spot diameter of 1 µm corresponds to a laser focus point (i.e. the diameter of the laser beam at the focal point of the beam) of 1 µm, but the laser focus point can vary by +20% or more due to spatial distribution of energy on the target (for instance, Gaussian beam shape) and variation in total laser energy with respect to the ablation threshold energy. Suitable objectives for focusing a laser beam include a reflecting objective, such as an objective of a Schwarzschild Cassegrain design (reverse Cassegrain). Refracting objectives can also be used, as can combination reflecting-refracting objectives. A single aspheric lens can also be used to achieve the required focusing. A solid-immersion lens or diffractive optic can also be used to focus the laser beam. Another means for controlling the spot size of the laser, which can be used alone or in combination with the above objectives is to pass the beam through an aperture prior to focusing. Different beam diameters can be achieved by passing the beam through apertures of different diameter from an array of diameters. In some instances, there is a single aperture of variable size, for example when the aperture is a diaphragm aperture. Sometimes, the diaphragm aperture is an iris diaphragm. Variation of the spot size can also be achieved through dithering of the optics. The one or more lenses and one or more apertures are positioned between the laser and the sample stage.

For completeness, the standard lasers for LA at subcellular resolution, as known in the art, are excimer or exciplex lasers. Suitable results can be obtained using an argon fluoride laser ($\lambda$=193 nm). Pulse durations of 10-15 ns with these lasers can achieve adequate ablation.

Overall, the laser pulse frequency and strength are selected in combination with the response characteristics of the MS detector to permit distinct detection of individual laser ablation plumes. In combination with using a small laser spot and a sample chamber having a short washout time, rapid and high resolution imaging is now feasible.

Laser Ablation Focal Point

To maximise the efficiency of a laser to ablate material from a sample, the sample should be at a suitable position with regard to the laser's focal point, for example at the focal point, as the focal point is where the laser beam will have the smallest diameter and so most concentrated energy. This can be achieved in a number of ways. A first way is that the sample can be moved in the axis of the laser light directed upon it (i.e. up and down the path of the laser light/towards and away from the laser source) to the desired point at which the light is of sufficient intensity to effect the desired ablation. Alternatively, or additionally, lenses can be used to move the focal point of the laser light and so its effective ability to ablate material at the location of the sample, for example by demagnification. The one or more lenses are positioned between the laser and the sample stage. A third way, which can be used alone or in combination with either or both of the two preceding ways, is to alter the position of the laser.

To assist the user of the system in placing the sample at the most suitable location for ablation of material from it, a camera can be directed at the stage holding the sample (discussed in more detail below). Accordingly, the disclosure provides a laser ablation sampling system comprising a camera directed on the sample stage. The image detected by the camera can be focused to the same point at which the laser is focused. This can be accomplished by using the same objective lens for both laser ablation and optical imaging.

By bringing the focal point of two into accordance, the user can be sure that laser ablation will be most effective when the optical image is in focus. Precise movement of the stage to bring the sample into focus can be effected by use of piezo activators, as available from Physik Instrumente, Cedrat-technologies, Thorlabs and other suppliers.

In a further mode of operation, the laser ablation is directed to the sample through the sample carrier. In this instance, the sample support should be chosen so that it is transparent (at least partially) to the frequency of laser radiation being employed to ablate the sample. Ablation through the sample can have advantages in particular situations, because this mode of ablation can impart additional kinetic energy to the plume of material ablated from the sample, driving the ablated material further away from the surface of the sample, so facilitating the ablated material's being transported away from the sample for analysis in the detector. Likewise, desorption based methods which remove slugs of sample material can also be mediated by laser radiation which passes through the carrier. The additional kinetic energy provided to the slug of material being desorbed can assist in catapulting the slug away from the sample carrier, and so facilitating the slug's being entrained in the carrier gas being flowed through the sample chamber.

In order to achieve 3D-imaging of the sample, the sample, or a defined area thereof, can be ablated to a first depth, which is not completely through the sample. Following this, the same area can be ablated again to a second depth, and so on to third, fourth, etc. depths. This way a 3D image of the sample can be built up. In some instances, it may be preferred to ablate all of the area for ablation to a first depth before proceeding to ablate at the second depth. Alternatively, repeated ablation at the same spot may be performed to ablate through different depths before proceeding onto the next location in the area for ablation. In both instances, deconvolution of the resulting signals at the MS to locations and depths of the sample can be performed by the imaging software. Thick tissue staining can be employed and the tissue is stabilized in the wet state similar to the workflow employed in confocal imaging (Clendenon et al., 2011. Microsc Microanal. 17:614-617).

Laser System Optics for Multiple Modes of Operation

As a matter of routine arrangement, optical components can be used to direct laser radiation, optionally of different wavelengths, to different relative locations. Optical components can also be arranged in order to direct laser radiation, optionally of different wavelengths, onto the sample from different directions. For example one or more wavelengths can be directed onto the sample from above, and one or more wavelengths of laser radiation (optionally different wavelengths) can be directed from below (i.e. through the substrate, such as a microscope slide, which carries the sample, also termed the sample carrier). This enables multiple modes of operation for the same apparatus. Accordingly, the laser system can comprise an arrangement of optical components, arranged to direct laser radiation, optionally of different wavelengths, onto the sample from different directions. Thus optical components may be arranged such that the arrangement directs laser radiation, optionally of different wavelengths, onto the sample from opposite directions. "Opposite" directions in this context is not limited to laser radiation directed perpendicularly onto the sample from above and below (which would be 180° opposite), but includes arrangements which direct laser radiation onto the sample at angles other than perpendicular to the sample. There is no requirement for the laser radiation directed onto the sample from different directions to be parallel. Sometimes, when the sample is on a sample carrier, the reflector arrangement can be arranged to direct laser radiation of a first wavelength directly onto the sample and to direct laser radiation of a second wavelength to the sample through the sample carrier.

Directing laser radiation through the sample carrier to the sample can be used to ablate the sample. In some systems, however, directing the laser radiation through the carrier can be used for "LIFTing" modes of operation, as discussed below in more detail in relation to desorption based sampling systems (although as will be appreciated by one of skill in the art, ablation and LIFTing can be performed by the same apparatus, and so what is termed herein a laser ablation sampling system can also act as a desorption based sampling system). The NA (numerical aperture) of the lens used to focus the laser radiation onto the sample from the first direction may be different from the NA of the lens used to focus the laser radiation (optionally at a different wavelength) onto the sample from the second direction. The lifting operation (e.g. where laser radiation is directed through the sample carrier) often employs a spot size of greater diameter than when ablation is being performed.

Sample Chamber of the Laser Ablation Sampling System

The sample is placed in the sample chamber when it is subjected to laser ablation. The sample chamber comprises a stage, which holds the sample (typically the sample is on a sample carrier). When ablated, the material in the sample forms plumes, and the flow of gas passed through the sample chamber from a gas inlet to a gas outlet carries away the plumes of aerosolised material, including any labelling atoms that were at the ablated location. The gas carries the material to the ionisation system, which ionises the material to enable detection by the detector. The atoms, including the labelling atoms, in the sample can be distinguished by the detector and so their detection reveals the presence or absence of multiple targets in a plume and so a determination of what targets were present at the ablated locus on the sample. Accordingly, the sample chamber plays a dual role in hosting the solid sample that is analysed, but also in being the starting point of the transfer of aerosolised material to the ionisation and detection systems. This means that the gas flow through the chamber can affect how spread out the ablated plume of material becomes as it passes through the system. A measure of how spread out the ablated plume becomes is the washout time of the sample chamber. This value is a measure of how long it takes material ablated from the sample to be carried out of the sample chamber by the gas flowing through it.

The spatial resolution of the signals generated from laser ablation (i.e. when ablation is used for imaging rather than exclusively for clearing, as discussed below) in this way depends on factors including: (i) the spot size of the laser, as signal is integrated over the total area which is ablated; and the speed with which plumes are generated versus the movement of the sample relative to the laser, and (ii) the speed at which a plume can be analysed, relative to the speed at which plumes are being generated, to avoid overlap of signal from consecutive plumes as mentioned above. Accordingly, being able to analyse a plume in the shortest time possible minimises the likelihood of plume overlap (and so in turn enables plumes to be generated more frequently), if individual analysis of plumes is desired.

Accordingly, a sample chamber with a short washout time (e.g. 100 ms or less) is advantageous for use with the apparatus and methods disclosed herein. A sample chamber with a long washout time will either limit the speed at which an image can be generated or will lead to overlap between signals originating from consecutive sample spots (e.g. Kindness et al. (2003; Clin Chem 49:1916-23), which had signal duration of over 10 seconds). Therefore aerosol washout time is a key limiting factor for achieving high resolution without increasing total scan time. Sample chambers with washout times of ≤100 ms are known in the art. For example, Gurevich & Hergenröder (2007; J. Anal. At. Spectrom., 22:1043-1050) discloses a sample chamber with a washout time below 100 ms. A sample chamber was disclosed in Wang et al. (2013; Anal. Chem. 85:10107-16) (see also WO 2014/146724) which has a washout time of 30 ms or less, thereby permitting a high ablation frequency (e.g. above 20 Hz) and thus rapid analysis. Another such sample chamber is disclosed in WO 2014/127034. The sample chamber in WO 2014/127034 comprises a sample capture cell configured to be arranged operably proximate to the target, the sample capture cell including: a capture cavity having an opening formed in a surface of the capture cell, wherein the capture cavity is configured to receive, through the opening, target material ejected or generated from the laser ablation site and a guide wall exposed within the capture cavity and configured to direct a flow of the carrier gas within the capture cavity from an inlet to an outlet such that at least a portion of the target material received within the capture cavity is transferrable into the outlet as a sample. The volume of the capture cavity in the sample chamber of WO 2014/127034 is less than 1 cm$^3$ and can be below 0.005 cm$^3$. Sometimes the sample chamber has a washout time of 25 ms or less, such as 20 ms or less, 10 ms or less, 5 ms or less, 2 ms or less, 1 ms, less or 500 µs or less, 200 µs or less, 100 µs or less, 50 µs or less, or 25 µs or less. For example, the sample chamber may have a washout time of 10 µs or more. Typically, the sample chamber has a washout time of 5 ms or less.

For completeness, sometimes the plumes from the sample can be generated more frequently than the washout time of the sample chamber, and the resulting images will smear accordingly (e.g. if the highest possible resolution is not deemed necessary for the particular analysis being undertaken).

The sample chamber typically comprises a translation stage which holds the sample (and sample carrier) and moves the sample relative to a beam of laser radiation. When a mode of operation is used which requires the direction of laser radiation through the sample carrier to the sample, e.g. as in the LIFTing methods discussed herein, the stage holding the sample carrier should also be transparent to the laser radiation used.

Thus, the sample may be positioned on the side of the sample carrier (e.g., glass slide) facing the laser radiation as it is directed onto the sample, such that ablation plumes are released on, and captured from, the same side as that from which the laser radiation is directed onto the sample. Alternatively, the sample may be positioned on the side of the sample carrier opposite to the laser radiation as it is directed onto the sample (i.e. the laser radiation passes through the sample carrier before reaching the sample), and ablation plumes are released on, and captured from, the opposite side to the laser radiation.

One feature of a sample chamber, which is of particular use where specific portions in various discrete areas of sample are ablated, is a wide range of movement in which the sample can be moved in the x and y (i.e. horizontal) axes in relation to the laser (where the laser beam is directed onto the sample in the z axis), with the x and y axes being perpendicular to one another. More reliable and accurate relative positions are achieved by moving the stage within the sample chamber and keeping the laser's position fixed in the laser ablation sampling system of the apparatus. The greater the range of movement, the more distant the discrete ablated areas can be from one another. The sample is moved in relation to the laser by moving the stage on which the sample is placed. Accordingly, the sample stage can have a range of movement within the sample chamber of at least 10 mm in the x and y axes, such as 20 mm in the x and y axes, 30 mm in the x and y axes, 40 mm in the x and y axes, 50 mm in the x and y axes, such as 75 mm in the x and y axes. Sometimes, the range of movement is such that it permits the entire surface of a standard 25 mm by 75 mm microscope slide to be analysed within the chamber. Of course, to enable subcellular ablation to be achieved, in addition to a wide range of movement, the movement should be precise. Accordingly, the stage can be configured to move the sample in the x and y axes in increments of less than 10 µm, such as less than 5 µm, less than 4 µm, less than 3 µm, less than 2 µm, 1 µm, or less than 1 µm, less than 500 nm, less than 200 nm, less than 100 nm. For example, the stage may be configured to move the sample in increments of at least 50 nm. Precise stage movements can be in increments of about 1 µm, such as 1 µm±0.1 µm. Commercially available microscope stages can be used, for example as available from Thorlabs, Prior Scientific, and Applied Scientific Instrumentation. Alternatively, the motorised stage can be built from components, based on positioners providing the desired range of movement and suitably fine precision movement, such as the SLC-24 positioners from Smaract. The movement speed of the sample stage can also affect the speed of the analysis. Accordingly, the sample stage has an operating speed of greater than 1 mm/s, such as 10 mm/s, 50 mm/s or 100 mm/s.

Naturally, when a sample stage in a sample chamber has a wide range of movement, the sample must be sized appropriately to accommodate the movements of the stage. Sizing of the sample chamber is therefore dependent on size of the sample to be involved, which in turn determines the size of the mobile sample stage. Exemplary sizes of sample chamber have an internal chamber of 10×10 cm, 15×15 cm or 20×20 cm. The depth of the chamber may be 3 cm, 4 cm or 5 cm. The skilled person will be able to select appropriate dimensions following the teaching herein. The internal dimensions of the sample chamber for analysing biological samples using a laser ablation sampler must be bigger than the range of movement of the sample stage, for example at least 5 mm, such as at least 10 mm. This is because if the walls of the chamber are too close to the edge of the stage, the flow of the carrier gas passing through the chamber which takes the ablated plumes of material away from the sample and into the ionisation system can become turbulent. Turbulent flow disturbs the ablated plumes, and so instead of remaining as a tight cloud of ablated material, the plume of material begins to spread out after it has been ablated and carried away to the ionisation system of the apparatus. A broader peak of the ablated material has negative effects on the data produced by the ionisation and detection systems because it leads to interference due to peak overlap, and so ultimately, less spatially resolved data, unless the rate of ablation is slowed down to such a rate that it is no longer experimentally of interest. As noted above, the sample chamber comprises a gas inlet and a gas outlet that takes material to the ionisation system. However, it may contain further ports acting as inlets or outlets to direct the flow of gas in the chamber and/or provide a mix of gases to the chamber, as determined to be appropriate by the skilled artisan for the particular ablative process being undertaken.

Camera

In addition to identifying the most effective positioning of the sample for laser ablation, the inclusion of a camera (e.g., an image sensor such as a charged coupled device image sensor based (CCD) camera, a complementary metal-oxide-semiconductor (CMOS) senor, or an active pixel sensor based camera), or any other light detecting means in a laser ablation sampling system enables various further analyses and techniques. A CCD is a means for detecting light and converting it into digital information that can be used to generate an image. In a CCD image sensor, there are a series of capacitors that detect light, and each capacitor represents a pixel on the determined image. These capacitors allow the conversion of incoming photons into electrical charges. The CCD is then used to read out these charges, and the recorded charges can be converted into an image. An active-pixel sensor (APS) is an image sensor consisting of an integrated circuit containing an array of pixel sensors, each pixel containing a photodetector and an active amplifier, e.g. a CMOS sensor.

A camera can be incorporated into any laser ablation sampling system discussed herein. The camera can be used to scan the sample to identify cells of particular interest or regions of particular interest (for example cells of a particular morphology), or for fluorescent probes specific for an antigen, or an intracellular or structure. In certain embodiments, the fluorescent probes are histochemical stains or antibodies that also comprise a detectable metal tag. Once such cells have been identified, then laser pulses can be directed at these particular cells to ablate material for analysis, for example in an automated (where the system both identifies and ablates the feature(s)/regions(s), such as cell(s), of interest) or semi-automated process (where the user of the system, for example a clinical pathologist, identifies the features/region(s) of interest, which the system then ablates in an automated fashion). This enables a significant increase in the speed at which analyses can be conducted, because instead of needing to ablate the entire sample to analyse particular cells, the cells of interest can be specifically ablated. This leads to efficiencies in methods of analysing biological samples in terms of the time taken to perform the ablation, but in particular in the time taken to interpret the data from the ablation, in terms of constructing images from it. Constructing images from the data is one of the more time-consuming parts of the imaging procedure, and therefore by minimising the data collected to the data from relevant parts of the sample, the overall speed of analysis is increased.

The camera may record the image from a confocal microscope. Confocal microscopy is a form of optical microscopy that offers a number of advantages, including the ability to reduce interference from background information (light) away from the focal plane. This happens by elimination of out-of-focus light or glare. Confocal microscopy can be used to assess samples for the morphology of the cells, or whether a cell is a discrete cell or part of a clump of cells. Often, the sample is specifically labelled with fluorescent markers (such as by labelled antibodies or by labelled nucleic acids). These fluorescent makers can be used to stain specific cell populations (e.g. expressing certain genes and/or proteins) or specific morphological features on cells (such as the nucleus, or mitochondria) and when illuminated with an appropriate wavelength of light, these regions of the sample are specifically identifiable. Some systems described herein therefore can comprise a laser for exciting fluorophores in the labels used to label the sample. Alternatively, an LED light source can be used for exciting the fluorophores. Non-confocal (e.g. wide field) fluorescent microscopy can also be used to identify certain regions of the biological sample, but with lower resolution than confocal microscopy.

An alternative imaging technique is two-photon excitation microscopy (also referred to as non-linear or multiphoton microscopy). The technique commonly employs near-IR light to excite fluorophores. Two photons of IR light are absorbed for each excitation event. Scattering in the tissue is minimized by IR. Further, due to the multiphoton absorption, the background signal is strongly suppressed. The most commonly used fluorophores have excitation spectra in the 400-500 nm range, whereas the laser used to excite the two-photon fluorescence lies in near-IR range. If the fluorophore absorbs two infrared photons simultaneously, it will absorb enough energy to be raised into the excited state. The fluorophore will then emit a single photon with a wavelength that depends on the type of fluorophore used that can then be detected.

When a laser is used to excite fluorophores for fluorescence microscopy, sometimes this laser is the same laser that generates the laser light used to ablate material from the biological sample, but used at a power that is not sufficient to cause ablation of material from the sample. Sometimes the fluorophores are excited by the wavelength of light that the laser then ablates the sample with. In others, a different wavelength may be used, for example by generating different harmonics of the laser to obtain light of different wavelengths, or exploiting different harmonics generated in a harmonic generation system, discussed above, apart from the harmonics which are used to ablate the sample. For example, if the fourth and/or fifth harmonic of a Nd:YAG laser are used, the fundamental harmonic, or the second to third harmonics, could be used for fluorescence microscopy.

As an example technique combining fluorescence and laser ablation, it is possible to label the nuclei of cells in the biological sample with an antibody or nucleic acid conjugated to a fluorescent moiety. Accordingly, by exciting the fluorescent label and then observing and recording the positions of the fluorescence using a camera, it is possible to direct the ablating laser specifically to the nuclei, or to areas not including nuclear material. The division of the sample into nuclei and cytoplasmic regions will find particular application in field of cytochemistry. By using an image sensor (such as a CCD detector or an active pixel sensor, e.g. a CMOS sensor), it is possible to entirely automate the process of identifying features/regions of interest and then ablating them, by using a control module (such as a computer or a programmed chip) which correlates the location of the fluorescence with the x,y coordinates of the sample and then directs the ablation laser to that location. As part of this process the first image taken by the image sensor may have a low objective lens magnification (low numerical aperture), which permits a large area of the sample to be surveyed. Following this, a switch to an objective with a higher magnification can be used to home in on the particular features of interest that have been determined to fluoresce by higher magnification optical imaging. These features recorded to fluoresce may then be ablated by a laser. Using a lower numerical aperture lens first has the further advantage that the depth of field is increased, thus meaning features buried within the sample may be detected with greater sensitivity than screening with a higher numerical aperture lens from the outset.

In methods and systems in which fluorescent imaging is used, the emission path of fluorescent light from the sample to the camera may include one or more lenses and/or one or more optical filters. By including an optical filter adapted to pass a selected spectral bandwidth from one or more of the fluorescent labels, the system is adapted to handle chromatic aberrations associated with emissions from the fluorescent labels. Chromatic aberrations are the result of the failure of lenses to focus light of different wavelengths to the same focal point. Accordingly, by including an optical filter, the background in the optical system is reduced, and the resulting optical image is of higher resolution. A further way to minimise the amount of emitted light of undesired wavelengths that reaches the camera is to exploit chromatic aberration of lenses deliberately by using a series of lenses designed for the transmission and focus of light at the wavelength transmitted by the optical filter, akin to the system explained in WO 2005/121864.

A higher resolution optical image is advantageous in this coupling of optical techniques and laser ablation sampling, because the accuracy of the optical image then determines the precision with which the ablating laser can be directed to ablate the sample.

Accordingly, in some embodiments disclosed herein, the apparatus of the invention comprises a camera. This camera can be used on-line to identify features/areas of the sample, e.g. specific cells, which can then be ablated (or desorbed by LIFTing—see below), such as by firing a burst of pulses at the feature/region of interest to ablate or desorb a slug of sample material from the feature/region of interest. Where a burst of pulses is directed at the sample, the material in the resulting plumes detected can be as a continuous event (the plumes from each individual ablation in effect form a single plume, which is then carried on for detection). While each cloud of sample material formed from the aggregated plumes from locations within a feature/region of interest can be analysed together, sample material in plumes from each different feature/region of interest is still kept discrete. That is to say, that sufficient time is left between ablation of different features/areas of interest to allow sample material from the nth feature/area interest before ablation of the (n+1)th feature/area is begun.

In a further mode of operation combining both fluorescence analysis and laser ablation sampling, instead of analysing the entire slide for fluorescence before targeting laser ablation to those locations, it is possible to fire a pulse from the laser at a spot on the sample (at low energy so as only to excite the fluorescent moieties in the sample rather than ablate the sample) and if a fluorescent emission of expected wavelength is detected, then the sample at the spot can be ablated by firing the laser at that spot at full energy, and the resulting plume analysed by a detector as described below. This has the advantage that the rastering mode of analysis is maintained, but the speed is increased, because it is possible to pulse and test for fluorescence and obtain results immediately from the fluorescence (rather than the time taken to analyse and interpret ion data from the detector to determine if the region was of interest), again enabling only the loci of importance to be targeted for analysis. Accordingly, applying this strategy in imaging a biological sample comprising a plurality of cells, the following steps can be performed: (i) labelling a plurality of different target molecules in the sample with one or more different labelling atoms and one or more fluorescent labels, to provide a labelled sample; (ii) illuminating a known location of the sample with light to excite the one or more fluorescent labels; (iii) observing and recording whether there is fluorescence at the location; (iv) if there is fluorescence, directing laser ablation at the location, to form a plume; (v) subjecting the plume to inductively coupled plasma mass spectrometry, and (vi) repeating steps (ii)-(v) for one or more further known locations on the sample, whereby detection of labelling atoms in the plumes permits construction of an image of the sample of the areas which have been ablated.

In some instances, the sample, or the sample carrier, may be modified so as to contain optically detectable (e.g., by optical or fluorescent microscopy) moieties at specific locations. The fluorescent locations can then be used to positionally orient the sample in the apparatus. The use of such marker locations finds utility, for example, where the sample may have been examined visually "offline"—i.e. in a piece of apparatus other than the apparatus of the invention. Such an optical image can be marked with feature(s)/region(s) of interest, corresponding to particular cells by, say, a physician, before the optical image with the feature(s)/region(s) of interest highlighted and the sample are transferred to an apparatus according to the invention. Here, by reference to the marker locations in the annotated optical image, the apparatus of the invention can identify the corresponding fluorescent positions by use of the camera and calculate an ablative and/or desorptive (LIFTing) plan for the positions of the laser pulses accordingly. Accordingly, in some embodiments, the invention comprises an orientation controller module capable of performing the above steps.

In some instances, selection of the features/regions of interest may performed using the apparatus of the invention, based on an image of the sample taken by the camera of the apparatus of the invention.

The methods disclosed herein may also be provided as a computer program product including a non-transitory, machine-readable medium having stored thereon instructions that may be used to program a computer (or other electronic device) to perform the processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/computer-readable medium suitable for storing electronic instructions. Accordingly, the invention also provides a machine-readable medium comprising instructions for performing a method as disclosed herein.

Optical Microscope

As described above, the autofocus sensor may include a camera (e.g., image sensor). This camera may be shared with an inspection system (e.g., an optical microscope) of the apparatus, such as a camera for identifying positioning of laser ablation. Alternatively, the optical microscope may include a camera (e.g., image sensor) separate from the autofocus sensor, such as when the autofocus sensor has a non-camera sensor.

An optical microscope of the subject application may include a confocal, fluorescence or brightfield/widefield microscope.

In certain aspects, the focal point of a laser source of the laser ablation sampling system may confocal with the autofocus component and autofocus sensor of the autofocus system. For example, the optical microscope may confocal with the sampling system and the autofocus system. The sampling system, the autofocus system, and the optical microscope may share at lease some optical components.

Transfer Conduit

The transfer conduit forms a link between the laser ablation sampling system and the ionisation system, and allows the transportation of plumes of sample material, generated by the laser ablation of the sample, from the laser ablation sampling system to the ionisation system. Part (or all) of the transfer conduit may be formed, for example, by drilling through a suitable material to produce a lumen (e.g., a lumen with a circular, rectangular or other cross-section) for transit of the plume. The transfer conduit sometimes has an inner diameter in the range 0.2 mm to 3 mm. Sometimes, the internal diameter of the transfer conduit can be varied along its length. For example, the transfer conduit may be tapered at an end. A transfer conduit sometimes has a length in the range of 1 centimeter to 100 centimeters. Sometimes the length is no more than 10 centimeters (e.g., 1-10 centimeters), no more than 5 centimeters (e.g., 1-5 centimeters), or no more than 3 cm (e.g., 0.1-3 centimeters). Sometimes the transfer conduit lumen is straight along the entire distance, or nearly the entire distance, from the ablation system to the ionisation system. Other times the transfer conduit lumen is not straight for the entire distance and changes orientation. For example, the transfer conduit may make a gradual 90 degree turn. This configuration allows for the plume generated by ablation of a sample in the laser ablation sampling system to move in a vertical plane initially while the axis at the transfer conduit inlet will be pointing straight up, and move horizontally as it approaches the ionisation system (e.g. an ICP torch which is commonly oriented horizontally to take advantage of convectional cooling). The transfer conduit can be straight for a distance of least 0.1 centimeters, at least 0.5 centimeters or at least 1 centimeter from the inlet aperture though which the plume enters or is formed. In general terms, typically, the transfer conduit is adapted to minimize the time it takes to transfer material from the laser ablation sampling system to the ionisation system.

Transfer Conduit Inlet, Including Sample Cone

The transfer conduit comprises an inlet in the laser ablation sampling system (in particular within the sample chamber of the laser ablation sampling system; it therefore also represents the principal gas outlet of the sample chamber). The inlet of the transfer conduit receives sample material ablated from a sample in the laser ablation sampling system, and transfers it to the ionisation system. In some instances, the laser ablation sampling system inlet is the source of all gas flow along the transfer conduit to the ionisation system. In some instances, the laser ablation sampling system inlet that receives material from the laser ablation sampling system is an aperture in the wall of a conduit along which a second "transfer" gas is flowed (as disclosed, for example in WO2014146724 and WO2014147260) from a separate transfer flow inlet. In this instance, the transfer gas forms a significant proportion, and in many instances the majority of the gas flow to the ionisation system. The sample chamber of the laser ablation sampling system contains a gas inlet. Flowing gas into the chamber through this inlet creates a flow of gas out of the chamber though the inlet of the transfer conduit. This flow of gas captures plumes of ablated material, and entrains it as it into the transfer conduit (typically the laser ablation sampling system inlet of the transfer conduit is in the shape of a cone, termed herein the sample cone) and out of the sample chamber into the conduit passing above the chamber. This conduit also has gas flowing into it from the separate transfer flow inlet. The component comprising the transfer flow inlet, laser ablation sampling system inlet and which begins the transfer conduit which carries the ablated sample material towards the ionisation system can also termed a flow cell (as it is in WO2014146724 and WO2014147260).

The transfer flow fulfils at least three roles: it flushes the plume entering the transfer conduit in the direction of the ionisation system, and prevents the plume material from contacting the side walls of the transfer conduit; it forms a "protection region" above the sample surface and ensures that the ablation is carried out under a controlled atmosphere; and it increases the flow speed in the transfer conduit. Usually, the viscosity of the capture gas is lower than the viscosity of the transfer gas. This helps to confine the plume of sample material in the capture gas in the center of the transfer conduit and to minimize the diffusion of the plume of sample material downstream of the laser ablation sampling system (because in the center of the flow, the transport rate is more constant and nearly flat). The gas(es) may be, for example, and without limitation, argon, xenon, helium, nitrogen, or mixtures of these. A common transfer gas is argon. Argon is particularly well-suited for stopping the diffusion of the plume before it reaches the walls of the transfer conduit (and it also assists improved instrumental sensitivity in apparatus where the ionisation system is an argon gas-based ICP). The capture gas is preferably helium. However, the capture gas may be replaced by or contain other gases, e.g., hydrogen, nitrogen, or water vapor. At 25° C., argon has a viscosity of 22.6 µPas, whereas helium has a viscosity of 19.8 µPas. Sometimes, the capture gas is helium and the transfer gas is argon.

As described in WO2014169394, the use of a sample cone minimizes the distance between the target and the laser ablation sampling system inlet of the transfer conduit. Because of the reduced distance between the sample and the point of the cone through which the capture gas can flow cone, this leads to improved capture of sample material with less turbulence, and so reduced spreading of the plumes of ablated sample material. The inlet of the transfer conduit is therefore the aperture at the tip of the sample cone. The cone projects into the sample chamber.

An optional modification of the sample cone is to make it asymmetrical. When the cone is symmetrical, then right at the center the gas flow from all directions neutralizes, so the overall flow of gas is zero along the surface of the sample at the axis of the sample cone. By making the cone asymmetrical, a non-zero velocity along the sample surface is created, which assists in the washout of plume materials from the sample chamber of the laser ablation sampling system.

In practice, any modification of the sample cone that causes a non-zero vector gas flow along the surface of the sample at the axis of the cone may be employed. For instance, the asymmetric cone may comprise a notch or a series of notches, adapted to generate non-zero vector gas flow along the surface of the sample at the axis of the cone. The asymmetric cone may comprise an orifice in the side of the cone, adapted to generate non-zero vector gas flow along the surface of the sample at the axis of the cone. This orifice will imbalance gas flows around the cone, thereby again generating a non-zero vector gas flow along the surface of the sample at the axis of the cone at the target. The side of the cone may comprise more than one orifice and may include both one or more notches and one or more orifices. The edges of the notch(es) and/or orifice(s) are typically smoothed, rounded or chamfered in order to prevent or minimize turbulence.

Different orientations of the asymmetry of the cone will be appropriate for different situations, dependent on the choice of capture and transfer gas and flow rates thereof, and it is within the abilities of the skilled person to appropriately identify the combinations of gas and flow rate for each orientation.

All of the above adaptations may be present in a single asymmetric sample cone as use in the invention. For example, the cone may be asymmetrically truncated and formed from two different elliptical cone halves, the cone may be asymmetrically truncated and comprise one of more orifices and so on.

The sample cone is therefore adapted to capture a plume of material ablated from a sample in the laser ablation sampling system. In use, the sample cone is positioned operably proximate to the sample, e.g. by maneuvering the sample within the laser ablation sampling system on a movable sample carrier tray, as described already above. As noted above, plumes of ablated sample material enter the transfer conduit through an aperture at the narrow end of the sample cone. The diameter of the aperture can be a) adjustable; b) sized to prevent perturbation to the ablated plume as it passes into the transfer conduit; and/or c) about the equal to the cross-sectional diameter of the ablated plume.

Tapered Conduits

In tubes with a smaller internal diameter, the same flow rate of gas moves at a higher speed. Accordingly, by using a tube with a smaller internal diameter, a plume of ablated sample material carried in the gas flow can be transported across a defined distance more rapidly at a given flow rate (e.g. from the laser ablation sampling system to the ionisation system in the transfer conduit). One of the key factors in how quickly an individual plume can be analysed is how much the plume has diffused during the time from its generation by ablation through to the time its component ions are detected at the mass spectrometer component of the apparatus (the transience time at the detector). Accordingly, by using a narrow transfer conduit, the time between ablation and detection is reduced, thereby meaning diffusion is decreased because there is less time in which it can occur, with the ultimate result that the transience time of each ablation plume at the detector is reduced. Lower transience times mean that more plumes can be generated and analyzed per unit time, thus producing images of higher quality and/or faster.

The taper may comprise a gradual change in the internal diameter of the transfer conduit along said portion of the length of the transfer conduit (i.e. the internal diameter of the tube were a cross section taken through it decreases along the portion from the end of the portion towards the inlet (at the laser ablation sampling system end) to the outlet (at the ionisation system end). Usually, the region of the conduit near where ablation occurs has a relatively wide internal diameter. The larger volume of the conduit before the taper facilitates the confinement of the materials generated by ablation. When the ablated particles fly off from the ablated spot they travel at high velocities. The friction in the gas slows these particles down but the plume can still spread on a sub-millimeter to a millimeter scale. Allowing for sufficient distances to the walls helps with the containment of the plume near the center of the flow.

Because the wide internal diameter section is only short (of the order of 1-2 mm), it does not contribute significantly to the overall transience time providing the plume spends more time in the longer portion of the transfer conduit with a narrower internal diameter. Thus, a larger internal diameter portion is used to capture the ablation product and a smaller internal diameter conduit is used to transport these particles rapidly to the ionisation system.

The diameter of the narrow internal diameter section is limited by the diameter corresponding to the onset of turbulence. A Reynolds number can be calculated for a round tube and a known flow. In general a Reynolds number above 4000 will indicate a turbulent flow, and thus should be avoided. A Reynolds number above 2000 will indicate a transitional flow (between non-turbulent and turbulent flow), and thus may also be desired to be avoided. For a given mass flow of gas the Reynolds number is inversely proportional to the diameter of the conduit. The internal diameter of the narrow internal diameter section of the transfer conduit commonly is narrower than 2 mm, for example narrower than 1.5 mm, narrower than 1.25 mm, narrower than 1 mm, but greater than the diameter at which a flow of helium at 4 liters per minute in the conduit has a Reynolds number greater than 4000.

Rough or even angular edges in the transitions between the constant diameter portions of the transfer conduit and the taper may cause turbulence in the gas flow, and typically are avoided.

Sacrificial Flow

At higher flows, the risk of turbulence occurring in the conduit increases. This is particularly the case where the transfer conduit has a small internal diameter (e.g. 1 mm). However, it is possible to achieve high speed transfer (up to and in excess of 300 m/s) in transfer conduits with a small internal diameter if a light gas, such as helium or hydrogen, is used instead of argon which is traditionally used as the transfer flow of gas.

High speed transfer presents problems insofar as it may cause the plumes of ablated sample material to be passed through the ionisation system without an acceptable level of ionisation occurring. The level of ionisation can drop because the increased flow of cool gas reduces the temperature of the plasma at the end of the torch. If a plume of sample material is not ionised to a suitable level, information is lost from the ablated sample material—because its components (including any labelling atoms/elemental tags) cannot be detected by the mass spectrometer. For example, the sample may pass so quickly through the plasma at the end of the torch in an ICP ionisation system that the plasma ions do not have sufficient time to act on the sample material to ionise it. This problem, caused by high flow, high speed transfer in narrow internal diameter transfer conduits can be solved by the introduction of a flow sacrificing system at the outlet of the transfer conduit. The flow sacrificing system is adapted to receive the flow of gas from the transfer conduit, and pass only a portion of that flow (the central portion of the flow comprising any plumes of ablated sample material) onwards into the injector that leads to the ionisation system. To facilitate dispersion of gas from the transfer conduit in the flow sacrificing system, the transfer conduit outlet can be flared out.

The flow sacrificing system is positioned close to the ionisation system, so that the length of the tube (e.g. injector) that leads from the flow sacrificing system to the ionisation system is short (e.g. ~1 cm long; compared to the length of the transfer conduit which is usually of a length of the order of tens of cm, such as ~50 cm). Thus the lower gas velocity within the tube leading from the flow sacrificing system to the ionisation system does not significantly affect the total transfer time, as the relatively slower portion of the overall transport system is much shorter.

In most arrangements, it is not desirable, or in some cases possible, to significantly increase the diameter of the tube (e.g. the injector) which passes from the flow sacrificing system to the ionisation system as a way of reducing the speed of the gas at a volumetric flow rate. For example, where the ionisation system is an ICP, the conduit from the flow sacrificing system forms the injector tube in the center of the ICP torch. When a wider internal diameter injector is used, there is a reduction in signal quality, because the plumes of ablated sample material cannot be injected so precisely into the center of the plasma (which is the hottest and so the most efficiently ionising part of the plasma). The strong preference is for injectors of 1 mm internal diameter, or even narrower (e.g. an internal diameter of 800 µm or less, such as 600 µm or less, 500 µm or less or 400 µm or less). Other ionisation techniques rely on the material to be ionised within a relatively small volume in three dimensional space (because the necessary energy density for ionisation can only be achieved in a small volume), and so a conduit with a wider internal diameter means that much of the sample material passing through the conduit is outside of the zone in which energy density is sufficient to ionise the sample material. Thus narrow diameter tubes from the flow sacrificing system into the ionisation system are also employed in apparatus with non-ICP ionisation systems. As noted above, if a plume of sample material is not ionised to a suitable level, information is lost from the ablated sample material—because its components (including any labelling atoms/ elemental tags) cannot be detected by the mass spectrometer.

Pumping can be used to help ensure a desired split ratio between the sacrificial flow and the flow passing into the inlet of the ionisation system. Accordingly, sometimes, the flow sacrificing system comprises a pump attached to the sacrificial flow outlet. A controlled restrictor can be added to the pump to control the sacrificial flow. Sometimes, the flow sacrificing system also comprises a mass flow controller, adapted to control the restrictor.

Where expensive gases are used, the gas pumped out of the sacrificial flow outlet can be cleaned up and recycled back into the same system using known methods of gas purification. Helium is particularly suited as a transport gas as noted above, but it is expensive; thus, it is advantageous to reduce the loss of helium in the system (i.e. when it is passed into the ionisation system and ionised). Accordingly, sometimes a gas purification system is connected to the sacrificial flow outlet of the flow sacrificing system.

Ionisation System

In order to generate elemental ions, it is necessary to use a hard ionisation technique that is capable of vaporising, atomising and ionising the atomised sample.

Inductively Coupled Plasma Torch

An apparatus of the subject application may further include an inductively coupled plasma (ICP) torch, or may be coupled to an ICP torch. For example, an apparatus of the subject application may further include an ICP mass spectrometer (ICP-MS).

Commonly, an inductively coupled plasma is used to ionise the material to be analysed before it is passed to the mass detector for analysis. It is a plasma source in which the energy is supplied by electric currents produced by electromagnetic induction. The inductively coupled plasma is sustained in a torch that consists of three concentric tubes, the innermost tube being known as the injector.

The induction coil that provides the electromagnetic energy that maintains the plasma is located around the output end of the torch. The alternating electromagnetic field reverses polarity many millions of times per second. Argon gas is supplied between the two outermost concentric tubes. Free electrons are introduced through an electrical discharge and are then accelerated in the alternating electromagnetic field whereupon they collide with the argon atoms and ionise them. At steady state, the plasma consists of mostly of argon atoms with a small fraction of free electrons and argon ions.

The ICP can be retained in the torch because the flow of gas between the two outermost tubes keeps the plasma away from the walls of the torch. A second flow of argon introduced between the injector (the central tube) and the intermediate tube keeps the plasma clear of the injector. A third flow of gas is introduced into the injector in the centre of the torch. Samples to be analysed are introduced through the injector into the plasma.

The ICP can comprise an injector with an internal diameter of less than 2 mm and more than 250 µm for introducing material from the sample into the plasma. The diameter of the injector refers to the internal diameter of the injector at the end proximal to the plasma. Extending away from the plasma, the injector may be of a different diameter, for example a wider diameter, wherein the difference in diameter is achieved through a stepped increase in diameter or because the injector is tapered along its length. For instance, the internal diameter of the injector can be between 1.75 mm and 250 µm, such as between 1.5 mm and 300 µm in diameter, between 1.25 mm and 300 µm in diameter, between 1 mm and 300 µm in diameter, between 900 µm and 300 µm in diameter, between 900 µm and 400 µm in diameter, for example around 850 µm in diameter. The use of an injector with an internal diameter less than 2 mm provides significant advantages over injectors with a larger diameter. One advantage of this feature is that the transience of the signal detected in the mass detector when a plume of sample material is introduced into the plasma is reduced with a narrower injector (the plume of sample material being the cloud of particular and vaporous material removed from the sample by the laser ablation sampling system). Accordingly, the time taken to analyse a plume of sample material from its introduction into the ICP for ionisation until the detection of the resulting ions in the mass detector is reduced. This decrease in time taken to analyse a plume of sample material enables more plumes of sample material to be detected in any given time period. Also, an injector with a smaller internal diameter results in the more accurate introduction of sample material into the centre of the induction coupled plasma, where more efficient ionisation occurs (in contrast to a larger diameter injector which could introduce sample material more towards the fringe of the plasma, where ionisation is not as efficient).

ICP torches (Agilent, Varian, Nu Instruments, Spectro, Leeman Labs, PerkinElmer, Thermo Fisher etc.) and injectors (for example from Elemental Scientific and Meinhard) are available.

Other Ionisation Techniques

Electron Ionisation

Electron ionisation involves bombarding a gas-phase sample with a beam of electrons. An electron ionisation chamber includes a source of electrons and an electron trap. A typical source of the beam of electrons is a rhenium or tungsten wire, usually operated at 70 electron volts energy. Electron beam sources for electron ionisation are available from Markes International. The beam of electrons is directed towards the electron trap, and a magnetic field applied parallel to the direction of the electrons travel causes the electrons to travel in a helical path. The gas-phase sample is directed through the electron ionisation chamber and interacts with the beam of electrons to form ions. Electron ionisation is considered a hard method of ionisation since the process typically causes the sample molecules to fragment. Examples of commercially available electron ionisation systems include the Advanced Markus Electron Ionisation Chamber.

Optional Further Components of the Laser Ablation Based Sampling and Ionisation System Ion Deflector Mass spectrometers detect ions when they hit a surface of their detector. The collision of an ion with the detector causes the release of electrons from the detector surface. These electrons are multiplied as they pass through the detector (the first released electron knocks out further electrons in the detector, these electrons then hit secondary plates which further amplify the number of electrons). The number of electrons hitting the anode of the detector generates a current. The number of electrons hitting the anode can be controlled by altering the voltage applied to the secondary plates. The current is an analog signal that can then be converted into a count of the ions hitting the detector by an analog-digital converter. When the detector is operating in its linear range, the current can be directly correlated to the number of ions. The quantity of ions that can be detected at once has a limit (which can be expressed as the number of ions detectable per second). Above this point, the number electrons released by ions hitting the detector is no longer correlated to the number of ions. This therefore places an upper limit on the quantitative capabilities of the detector.

When ions hit the detector, its surface becomes damaged by contamination. Over time, this irreversible contamination damage results in fewer electrons being released by the detector surface when an ion hits the detector, with the ultimate result that the detector needs replacing. This is termed "detector aging", and is a well-known phenomenon in MS.

Detector life can therefore be lengthened by avoiding the introduction of overloading quantities of ions into the MS. As noted above, when the total number of ions hitting the MS detector exceeds the upper limit of detection, the signal is not as informative as when the number of ions is below the upper limit because it is no longer quantitative. It is therefore desirable to avoid exceeding the upper limit of detection as it results in accelerated detector aging without generating useful data.

Analysis of large packets of ions by mass spectrometry involves a particular set of challenges not found in normal mass spectrometry. In particular, typical MS techniques involve introducing a low and constant level of material into the detector, which should not approach the upper detection limit or cause accelerated aging of the detector. On the other hand, laser ablation- and desorption-based techniques analyse a relatively large amount of material in a very short time window in the MS: e.g. the ions from a cell-sized patch of a tissue sample which is much larger than the small packets of ions typically analysed in MS. In effect, it is a deliberate almost overloading of the detector with analysed packed of ions resulting from ablation or lifting. In between the analysis events the signal is at baseline (a signal that is close to zero because no ions from labelling atoms are deliberately being entering into the MS from the sampling and ionisation system; some ions will inevitably be detected because the MS is not a complete vacuum).

Thus in apparatus described herein, there is an elevated risk of accelerated detector aging, because the ions from packets of ionised sample material labelled with a large number of detectable atoms can exceed the upper limit of detection and damage the detector without providing useful data.

To address these issues, the apparatus can comprise an ion deflector positioned between the sampling and ionisation system and the detector system (a mass spectrometer), operable to control the entry of ions into the mass spectrometer. In one arrangement, when the ion deflector is on, the ions received from the sampling and ionisation system are deflected (i.e. the path of the ions is changed and so they do not reach the detector), but when the deflector is off the ions are not deflected and reach the detector. How the ion deflector is deployed will depend on the arrangement of the sampling and ionisation system and MS of the apparatus. E.g. if the portal through which the ions enter the MS is not directly in line with the path of ions exiting the sampling and ionisation system, then by default the appropriately arranged ion deflector will be on, in order to direct ions from the sampling and ionisation system into the MS. When an event resulting from the ionisation a packet of ionised sample material considered likely to overload the MS is detected (see below), the ion deflector is switched off, so that the rest of the ionised material from the event is not deflected into the MS and can instead simply hit an internal surface of the system, thereby preserving the life of the MS detector. The ion deflector is returned to its original state after the ions from the damaging event have been prevented from entering the MS, thereby allowing the ions from subsequent packets of ionised sample material to enter the MS and be detected.

Alternatively, in arrangements where (under normal operating conditions) there is no change in the direction of the ions emerging from the sampling and ionisation system before they enter the MS the ion deflector will be off, and the ions from the sampling and ionisation system will pass through it to be analysed in the MS. To prevent damage when a potential overload of the detector is detected, in this configuration the ion deflector is turned on, and so diverts ions so that they do not enter the detector in order to prevent damage to the detector.

The ions entering the MS from ionisation of sample material (such as a plume of material generated by laser ablation or desorption) do not enter the MS all at the same time, but instead enter as a peak with a frequency that follows a probability distribution curve about a maximum frequency: from baseline, at first a small number of ions enters the MS and are detected, and then the frequency of ions increases to a maximum before the number decreases again and trails off to baseline. An event likely to damage the detector can be identified because instead of a slow increase in the frequency of ions at the leading edge of the peak, there is a very quick increase in counts of ions hitting the detector.

The flow of ions hitting the detector of a TOF MS, a particular type of detector as discussed below, is not continual during the analysis of the ions in a packet of ionised sample material. The TOF comprises a pulser which releases the ions periodically into the flight chamber of the TOF MS in pulsed groups. By releasing the ions all at the known same time, the time of flight mass determination is enabled. The time between the releases of pulses of ions for time of flight mass determination is known as an extraction or push of the TOF MS. The push is in the order of microseconds. The signal from one or more packets of ions from the sampling and ionisation system therefore covers a number of pushes.

Accordingly, when the ion count reading jumps from the baseline to a very high count within one push (i.e. the first portion of the ions from a particular packet of ionised sample material) then it can be predicted that the main body of ions resulting from ionisation of the packet of sample material will be even greater, and so exceed the upper detection limit. It is at this point that an ion deflector can be operated to ensure that the damaging bulk of the ions are directed away from the detector (by being activated or deactivated, depending on the arrangement of the system, as discussed above).

Suitable ion deflectors based on quadrupoles are available in the art (e.g. from Colutron Research Corporation and Dreebit GmbH).

b. Desorption Based Sampling and Ionising System

A desorption based analyser typically comprises three components. The first is a desorption system for the generation of slugs of sample material from the sample for analysis. Before the atoms in the slugs of desorbed sample material (including any detectable labelling atoms as discussed below) can be detected, the sample must be ionised (and atomised). Accordingly, the apparatus comprises a second component which is an ionisation system that ionises the atoms to form elemental ions to enable their detection by the MS detector component (third component) based on mass/charge ratio. The desorption based sampling system and the ionisation system are connected by a transfer conduit. In many instances the desorption based sampling system is also a laser ablation based sampling system.

Desorption Sampling System

Figure 8:
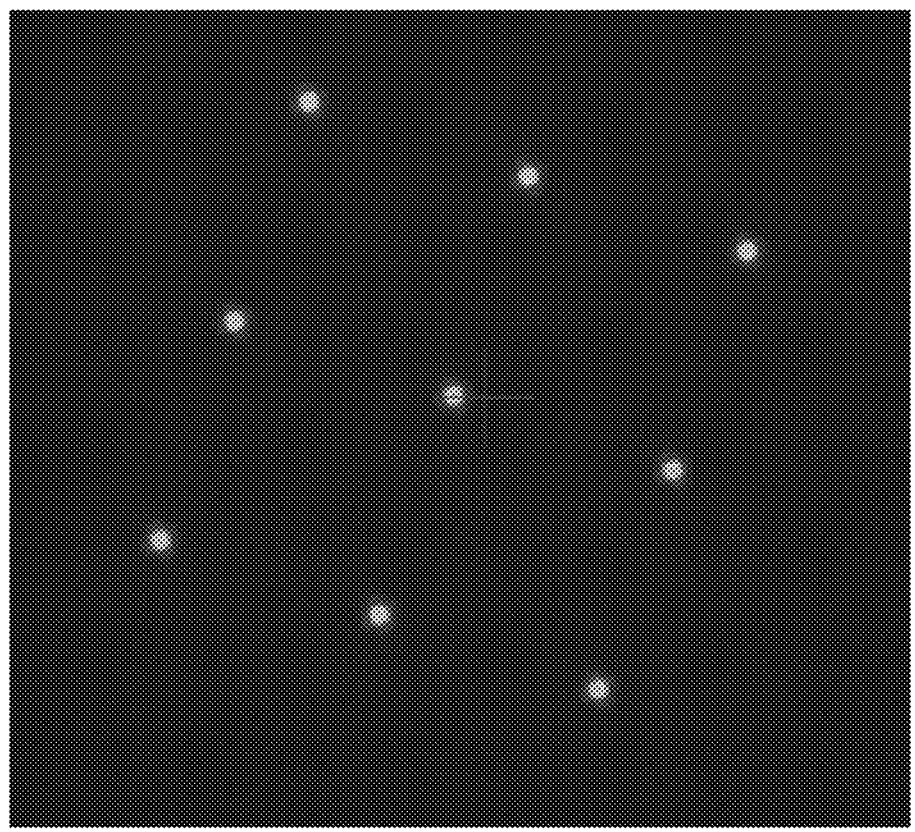
FIG. 8—Image from autofocus sensor in the autofocus system of embodiments of the present invention detecting reflected illumination radiation from a 9-aperture autofocus component of the invention, showing reflected radiation detected at 9 of the expected positions (i.e. regions of interest).
Figure 9:
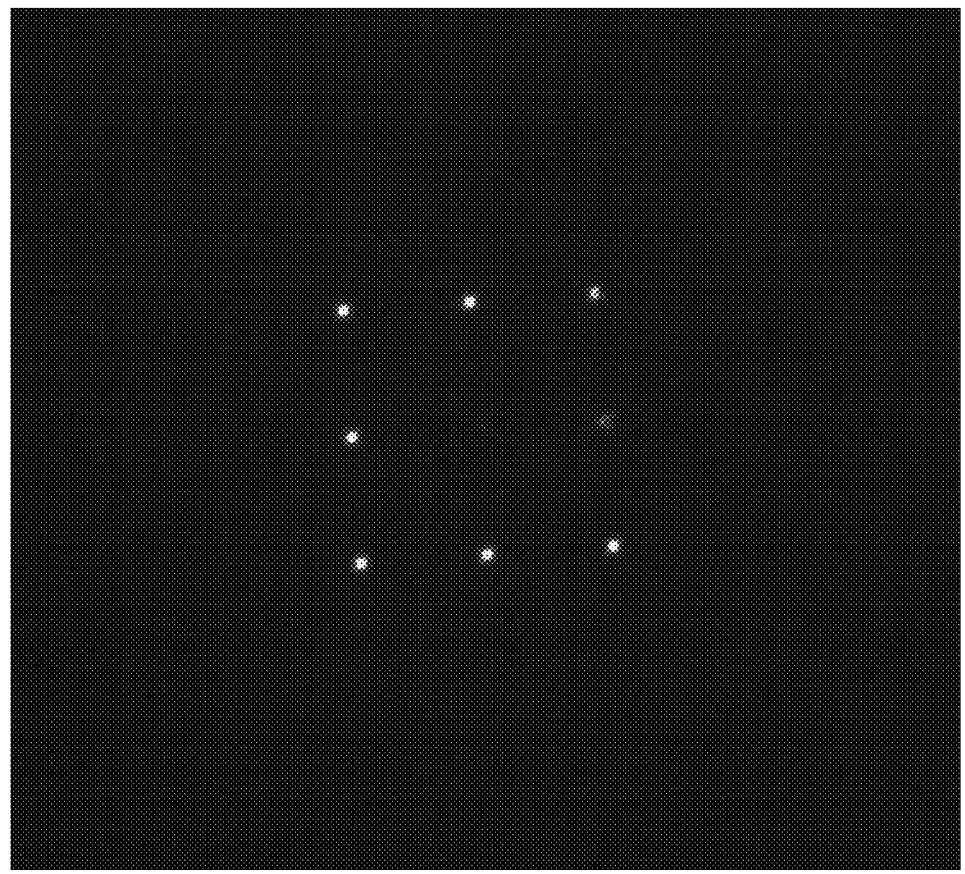
FIG. 9—Image from autofocus sensor in the autofocus system of embodiments of the present invention detecting reflected illumination radiation from a 9-aperture autofocus component of the invention, showing reflected radiation detected at several, but not all, of the expected positions (i.e. regions of interest).
Figure 10:
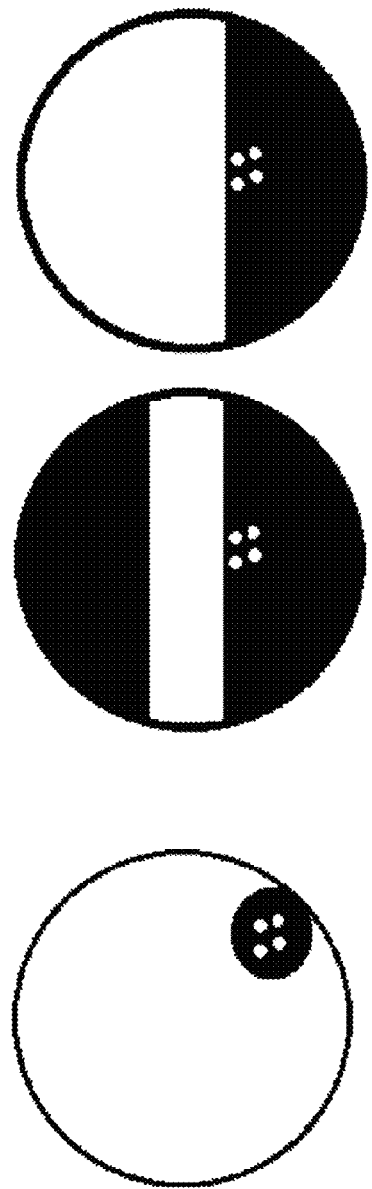
FIG. 10—Illustration of arrangements of hybrid autofocus components of embodiments of the present invention.

In some instances, rather than laser ablation being used to generate a particulate and/or vaporised plume of sample material, a bulk mass of sample material is desorbed from the sample carrier on which it is located without substantial disintegration of the sample and its conversion into small particles and/or vaporisation (see e.g. FIG. 8 of WO2016109825, and the accompanying description, which are herein incorporated by reference). Herein, the term slug is used to refer to this desorbed material (one particular form of a packet of sample material discussed herein). The slug can have dimensions from 10 nm to 10 µm, from 100 nm to 10 µm, and in certain instances from 1 µm to 100 µm. This process can be termed sample catapulting. Commonly, the slug represents a single cell (in which case the process can be termed cell catapulting).

The slug of sample material released from the sample can be a portion of the sample which has been cut into individual slugs for desorption prior to the desorption step, optionally in a process prior to the sample being inserted into the apparatus. A sample divided into discrete slugs prior to analysis is called a structured sample. Each of these individual slugs therefore represents a discrete portion of the sample that can be desorbed, ionised and analysed in the apparatus. By analysis of slugs from the discrete sites, an image can be built up with each slug representing a pixel of the image, in the same way that each location of a sample ablated by the laser ablation sampling system described above.

A structured sample may be prepared by various methods. For instance, a sample carrier comprising topographic features configured to cut a biological sample may be used. Here, a biological sample is applied onto the surface of the carrier, which causes the topographic features to cut and section the sample, in turn causing the sections of biological material to be retained by the plurality of discrete sites between the features to provide a structured biological sample. Alternatively, the sample carrier may not comprise such topographical features (in effect, a flat surface like a microscope slide, optionally functionalised as discussed below), in which case the sample may be applied to the sample carrier and the sample may be sectioned to define slugs of sample that can be desorbed for ionisation and analysis. The sectioning of the sample can be accomplished by mechanical tools such as blades or stamps, if the sample is a tissue section. Alternatively, the material around the sections of the sample to be desorbed can be removed by laser ablation in the same or a separate sample preparation setup. In certain techniques, the material can be removed by a setup employing a focused electron or ion beam. The focused electron or ion beam can lead to particularly narrow cuts (potentially on the 10 nm scale) between subsections leading to a pixel size on the order of 1 µm or in certain instances, 100 nm.

The slugs of sample material can be released from the carrier and each discrete portion of sample material sequentially introduced into the detector for analysis as a discrete event (generating a pixel of an image by the techniques discussed below). The benefits of sequential introduction of discrete material as opposed to random introduction of biological samples as in conventional mass cytometry or mass spectrometry include a higher sample processing rate. This is because the slug is transported from the sample chamber to the ionisation system as preferably a single piece of matter, and so cannot spread out as a plume of ablated material would in a flow of gas (in particular a gas flow in which there is some turbulence).

Desorption for Sampling

Sample material can be desorbed from the sample by thermal energy, mechanical energy, kinetic energy, and a combination of any of the foregoing. This kind of sampling is useful in particular in analysing biological samples.

In certain instances, sample material may be released from the sample by thermal mechanisms. For example, the surface of sample carrier becomes sufficiently hot to desorb a slug of sample material. The sample carrier may be coated to facilitate the bulk desorption process, for example with polyethylene naphthalate (PEN) polymer or PMMA polymer film. Heat can be provided by a radiative source such as a laser (such as the laser of a laser ablation sampling system discussed above). The energy applied to the surface should be sufficient to desorb the biological material, preferably without altering the sample material if it is from a biological sample. Any suitable radiation wavelength can be used, which can depend in part on the absorptive properties of the sample carrier. A surface or layer of the sample carrier may be coated with or include an absorber that absorbs laser radiation for conversion to heat. The radiation may be delivered to a surface of the carrier other than the surface on which the sample is located, or it may be delivered to the surface carrying the sample, such as through the thickness of the carrier. The heated surface may be a surface layer or may be an inner layer of a multilayer structure of the sample carrier. One example of the use of laser radiation energy is in a technique called LIFTing (Laser Induced Forward Transfer; see e.g. Doraiswamy et al., 2006, Applied Surface Science, 52: 4743-4747; Fernandez-Pradas, 2004, Thin Solid Films 453-454: 27-30; Kyrkis et al., in Recent Advances in Laser Processing of Materials, Eds. Perriere et al., 2006, Elsivier), in which the sample carrier may comprise a desorption film layer. The desorption film can absorb the radiation to cause release of the desorption film and/or the biological sample (e.g. in some instances the sample film desorbs from the sample carrier together with the biological sample, in other instances, the film remains attached to the sample carrier, and the biological sample desorbs from the desorption film).

Desorption by heating can take place on a nanosecond, picosecond or femtosecond time scale, depending on the laser used for desorption.

A sample may be attached to the sample carrier by a cleavable photoreactive moiety. Upon irradiating the cleavable photoreactive moiety with radiation (e.g. from a laser in the laser system of the laser ablation sampling system), the photoreactive moiety can cleave to release sample material. The sample carrier may comprise (i) a cleavable photoreactive moiety that couples the sample to the sample carrier and (ii) a desorption film as discussed above. In this situation, a first laser radiation pulse may be used to cause cleavage of the photoreactive moiety and a second laser radiation pulse may be used to target the desorption film to cause separation of the sample from the sample carrier by lifting (or a thermal energy pulse introduced by other means may be used to heat the desorption film and so cause separation of sample material from the sample carrier). The first and second pulses may be of different wavelengths. Thus in some methods (e.g. comprising both ablation and desorption), separation of the sample from the sample carrier may involve multiple laser pulses of different wavelengths. In some instances, cleavage of the photoreactive moiety and lifting may be accomplished by the same laser pulse.

The sample carrier may include a coating or layer of a chemically reactive species that imparts kinetic energy to the sample to release the sample from the surface. For example, a chemically reactive species may release a gas such as, for example, $H_2$, $CO_2$, $N_2$ or hydrochlorofluorocarbons. Examples of such compounds include blowing and foaming agents, which release gas upon heating. Generation of gas can be used to impart kinetic energy to desorbing sample material that can improve the reproducibility and direction of release of the material.

A sample carrier may comprise photoinitiated chemical reactants that undergo an exothermic reaction to generate heat for desorbing sample material. The coating of the carrier, or indeed particular chemical linkages in that carrier, discussed in the above paragraphs (that is irradiated by the laser to release the slug of sample material from the carrier) is an example of a material that can be targeted by a wavelength of laser radiation.

Typically, when performing ablation, the locations ablated are resolved as individual, non-overlapping, spots. However, when desorption is used as the means for introducing sample material into the apparatus, then overlapping spots may be used, for instance to ensure that all of the desorption film anchoring the sample to the sample carrier at a particular location is removed. The inventors have identified that desorption of cells with a single laser pulse with spot size large enough to fully desorb the cell from the sample carrier often causes break up of the slug of material. As soon as the slug of sample material breaks down into smaller parts, the transient time of the material in the ablated slug increases, because it inevitably spreads out as it passes from the chamber in which the sample is desorbed through the transport conduit, to the ionisation system and then on to the detector. Accordingly, maintaining the integrity of the desorbed slug enables the fastest rate of analysis of ablated slugs, meaning the fastest rate of analysis of cells, if the sample is a cell smear for example. Desorption of single cells as discrete slugs that commonly maintain their integrity until ionisation provides the opportunity to analyse single cells from a slide at a similar rate to that enabled by analysis of cells in liquid solution by CyTOF (Fluidigm, CA, USA). However, desorption of individual cells from a slide provides the additional advantages that the cells can be analysed visually first, thus meaning that cells of interest can be selected and cells of e.g. the wrong cell type can be excluded, thus increasing efficiency of the analysis. Moreover, it means that the slugs of material that are desorbed can be selected so that they are indeed single cells. Sometimes in the analysis of liquid samples, cells can clump together in doublets, triplets of higher multimers, or, by chance, two discrete cells can be analysed in the same event as a result of the sample introduction process. Accordingly, the atoms from two or more cells pass into the ionisation and detection systems together, resulting not only in inaccurate results but also in possible equipment damage due to overloading of the MS detector.

Often, the feature/region on the sample that is of interest does not represent a discrete entity, such as a lone cell, at a discrete site which can be easily desorbed in isolation. Instead, the cell of interest may be surrounded by other cells or material, of which analysis is not required or desired. Trying to perform desorption (e.g. lifting) of the feature/region of interest may therefore desorb both the cell of interest and surrounding material together. Atoms, such as labelling atoms which are used in elemental tags (see discussion below), from the surrounding area of the sample (e.g. from other cells which have been labelled) that are carried in a desorbed slug of material in addition to the specific feature/region (e.g. cell) of interest could therefore contaminate the reading for the location of interest.

The techniques of ablation and desorption (such as by lifting) can be combined in a single method. For example, to perform precise desorption of a feature/region (e.g. cell) of interest on a biological sample, e.g. a tissue section sample or cell suspension dispersion, on the sample carrier, laser ablation can be used to ablate the area around the cell of interest to clear it of other material. After clearing the surrounding area by ablation, the feature/region of interest can then be desorbed from the sample carrier, and then ionised and analyzed by mass spectrometry in line with standard mass cytometry or mass spectrometry procedures. In line with the above discussion, thermal, photolytic, chemical, or physical techniques can be used to desorb material from a feature/region of interest, optionally after ablation has been used to clear the area surrounding the location that will be desorbed. Often, lifting will be employed, to separate the slug of material from the sample carrier (e.g. a sample carrier which has been coated with a desorption film to assist the lifting procedure, as discussed above with regard to desorption of discrete slugs of sample material).

Accordingly, the invention provides a method of analysing a sample comprising
  (i) performing the method of the invention to place the sample at the focus point of a laser for laser ablation;
  (ii) desorbing a slug of sample material using laser radiation directed onto the sample on a sample stage; and
  (iii) ionizing the slug of sample material and detecting atoms in the slug by mass spectrometry.

The sample can be on a sample carrier, and in some instances, laser radiation is directed through the sample carrier to desorb the slug of sample material from the sample carrier.

In some embodiments, the method additionally comprises, prior to step (i) performing laser ablation of the sample. Sometimes, the ablation of the sample generates one or more plumes of sample material, and the plumes are individually ionised and the atoms in the plume detected by mass spectrometry. Sometimes the method further comprises, prior to step (i), the additional step labelling a plurality of different target molecules in the sample with one or more different labelling atoms/elemental tags, to provide a labelled sample. Laser ablation is used in some variants of the method to ablate the material around a feature/region of interest to clear the surrounding area before the sample material at the feature/region of interest is desorbed from the sample carrier as a slug of material.

The feature/region of interest can be identified by another technique before the laser ablation and desorption (e.g. by lifting) is performed. The inclusion of a camera (such as a charged coupled device image sensor based (CCD) camera or a CMOS camera or an active pixel sensor based camera), or any other light detecting means as described in the preceding sections is one way of enabling these techniques, for both online and offline analyses. The camera can be used to scan the sample to identify cells of particular interest or features/regions of particular interest (for example cells of a particular morphology). Once such locations have been identified, the locations can be lifted after laser pulses have been directed at the area around the feature/region of interest to clear other material by ablation before the location (e.g. cell) is lifted. This process may be automated (where the system both identifies, ablates and lifts the feature(s)/region(s) of interest) or semi-automated process (where the user of the system, for example a clinical pathologist, identifies the feature(s)/region(s) of interest, following which the system then performs ablation and lifting in an automated fashion). This enables a significant increase in the speed at which analyses can be conducted, because instead of needing to ablate the entire sample to analyze particular cells, the cells of interest can be specifically ablated.

The camera can record the image from a microscope (e.g. a confocal microscope). The identification may be by light microscopy, for example by examining cell morphology or cell size, or on whether the cell is a discrete single cell (in contrast to a member of a clump of cells). Sometimes, the sample can be specifically labelled to identify the feature(s) (e.g. cell(s)) of interest. Often, fluorescent markers are used to specifically stain the cells of interest (such as by using labelled antibodies or labelled nucleic acids), as discussed above in relation to methods of ablating visually-identified features/regions of interest; that section is not repeated here in full in the interests of brevity, but one of skill in the art will immediately appreciate that the features of those methods can be applied to desorption based methods and that this is within the technical teaching of this document. A high resolution optical image is advantageous in this coupling of optical techniques and lifting, because the accuracy of the optical image then determines the precision with which the ablating laser source can be directed to ablate the area surrounding the cell of interest which can subsequently be desorbed.

The invention also provides a method of analysing a sample comprising a plurality of cells, the method comprising steps of:
(i) labelling a plurality of different target molecules in the sample with one or more different labelling atoms, to provide a labelled sample;
(ii) illuminating the sample to identify one or more features of interest;
(iii) recording locational information of the one or more features of interest on the sample;
(iv) using the locational information of the features of interest to desorb a slug of sample material from a feature of interest, comprising first performing laser ablation to remove sample material surrounding the feature of interest using laser radiation, before the slug of sample material is desorbed from the location using laser radiation, wherein the laser radiation is directed onto the sample;
(v) ionizing the desorbed slug of sample material; and
(vi) subjecting the ionised sample material to mass spectrometry, for detection of labelling atoms in the sample material,
wherein the laser radiation used to desorb the slug of sample material is focused on the sample using an autofocusing method of the invention.

The invention also provides variants of the above method, for instance, a method of performing mass cytometry comprising a plurality of cells, comprising steps of:
(i) labelling a plurality of different target molecules in the sample with one or more different labelling atoms and one or more fluorescent labels, to provide a labelled sample;
(ii) illuminating the sample with laser radiation to excite the one or more fluorescent labels;
(iii) recording locational information of one or more locations of the sample based on the pattern of fluorescence;
(iv) using the locational information of based on the pattern of fluorescence to desorb a slug of sample material from a feature of interest, comprising first performing laser ablation to remove sample material surrounding the feature of interest using laser radiation, before the slug of sample material is desorbed from the location using laser radiation, wherein the laser radiation is directed onto the sample;
(v) ionizing the desorbed slug of sample material; and
(vi) subjecting the ionised sample material to mass spectrometry, for detection of labelling atoms in the sample material,
wherein the laser radiation used to desorb the slug of sample material is focused on the sample using an autofocusing method as described herein.

Sometimes, no data are recorded from the ablation performed to clear the area around the location to be desorbed (e.g. the cell of interest). Sometimes, data is recorded from the ablation of the surrounding area. Useful information that can be obtained from the surrounding area includes what target molecules, such as proteins and RNA transcripts, are present in the surrounding cells and intercellular milieu. This may be of particular interest when imaging solid tissue samples, where direct cell-cell interactions are common, and what proteins etc. are expressed in the surrounding cells may be informative on the state of the cell of interest.

Camera

The camera used in the desorption based sampling system can be as described above for the laser ablation based sampling system, and the discussion for the camera of the laser ablation based sampling system should be read in here.

Sample Chamber

The sample chamber used in the desorption based sampling system can be as described above for the laser ablation based sampling system. In instances where sampling of large slugs of sample material is being undertaken, the skilled practitioner will appreciate that gas flow volumes may need to be increased to ensure that the slug of material is entrained in the flow of gas and carried into the transfer conduit for transport to the ionisation system.

Transfer Conduit

The sample chamber used in the desorption based sampling system can be as described above for the laser ablation based sampling system. In instances where sampling of large slugs of sample material is being undertaken, the skilled practitioner will appreciate that the diameter of the lumen of the conduit will need to be appropriately sized to accommodate any slugs without the slug contacting the side of the lumen (because any contact may lead to fragmentation of the slug, and to the overlapping of signals—where atoms from the slug resulting the nth desorption event are spread into the detection window for the n+1th or subsequent slugs).

Ionisation System of the Desorption Based System

In many instances, the lifting techniques discussed above involve the removal of relatively large slugs of sample material (10 nm to 10 µm, from 100 nm to 10 µm, and in certain instances from 1 µm to 100 µm) which have not been converted into particulate and vaporous material. Accordingly, an ionisation technique which is capable of vaporising and atomising this relatively large quantity of material is required.

Inductively Coupled Plasma Torch

One such suitable ionisation system is an inductively coupled plasma, as already discussed above in the section beginning on page 57 in relation to laser ablation based sampling and ionisation systems.

Optional Further Components of the Desorption Based Sampling and Ionisation System Ion Deflector The ion deflector used in the desorption based sampling system can be as described above for the laser ablation based sampling system. Given the potential for desorption based sampling to remove intact large slugs of sample material, ion deflectors can be particularly useful in this kind of system for protecting the detector.

c. Laser Desorption/Ionisation Systems

In certain aspects, a sampling system may be a laser desorption system. A laser desorption/ionisation based analyser typically comprises two components. The first is a system for the generation of ions from the sample for analysis. In this apparatus, this is achieved by directing a laser beam onto the sample to generate ions; herein it is called a laser desorption ion generation system. These ejected sample ions (including any detectable ions from labelling atoms as discussed below) can be detected by a detector system (the second component) for instance a mass spectrometer (detectors are discussed in more detail below). This technique is known as laser desorption/ionisation mass spectrometry (LDI-MS). LDI is different from the desorption based sampling systems discussed in more detail below, because in the desorption based sampling system the sample material is desorbed as charge neutral slugs of material which are subsequently ionised to form elemental ions. On the contrary, here, ions are produced directly as a result of irradiation of the sample by the laser and no separate ionisation system is required.

The laser desorption ion generation system comprises: a laser; a sample chamber for housing the sample onto which radiation from the laser is directed; and ion optics that take ions generated from the sample and direct them to the detector for analysis. Accordingly, the invention provides an apparatus for analysing a sample comprising: a. a sample chamber to house the sample; b. a laser, adapted to desorb and ionize material from the sample, forming ions; c. ion optics, arranged to sample the ions formed by desorption ionisation, and to direct them away from sample towards the detector; and d. a detector to receive ions from said ion optics and to analyse said ions. In some embodiments, the apparatus comprises a laser adapted to desorb and ionize material from the sample, forming elemental ions, and wherein the detector receives the elemental ions from said sampling and ionisation system and detects said elemental ions. In some instances, the LDI is matrix assisted (i.e. MALDI)

In this process some molecules reach an energy level at which they desorb from the sample and become ionised. The ions may arise as primary ions directly as a result of the laser irradiation or as secondary ions, formed by collision of charge neutral species with the primary ions (e.g. proton transfer, cationization and electron capture). In some instances, ionisation is assisted by compounds (e.g. a matrix) added to the sample as the sample is being prepared, as discussed below.

Laser

A variety of different lasers can be used for LDI, including commercial lasers as discussed above in relation to the laser of the laser ablation sampling system, adapted as appropriate to enable desorption of ions. Accordingly, in some embodiments, the apparatus comprises a laser adapted to desorb and ionize material from the sample, forming elemental ions, and wherein the detector receives the elemental ions from said sampling and ionisation system and is adapted to detect said elemental ions. Sometimes, the apparatus comprises a laser adapted to desorb and ionize material from the sample, forming molecular ions, and wherein the detector receives the molecular ions from said sampling and ionisation system and is adapted to detect said molecular ions. In other instances, the apparatus comprises a laser adapted to desorb and ionize material from the sample, forming both elemental and molecular ions, and wherein the detector receives the ions from said sampling and ionisation system and is adapted to detect both said elemental and said molecular ions.

Exemplary lasers include those which emit at 193 nm, 213 nm or 266 nm (deep UV lasers that can cause release of ions from the sample without requiring a matrix to promote ionization, as in MALDI). Desorption of ions representing lichen metabolites following laser irradiation of a sample is demonstrated in Le Pogam et al., 2016 (Scientific Reports 6, Article number: 37807) at 355 nm.

Femtosecond lasers as discussed above are also advantageous in particular LDI applications.

For rapid analysis of a sample a high frequency of ablation is needed, for example more than 200 Hz (i.e. more than 200 laser shots per second, giving more than 200 clouds of ions per second). Commonly, the frequency of ion cloud generation by the laser system is at least 400 Hz, such as at least 500 Hz, at least 1 kHz, at least 10 kHz, at least 100 kHz or at least 1 MHz. For instance, the frequency of ablation by the laser system is within the range 200 Hz-1 MHz, within the range 500 Hz-100 kHz, within the range 1-10 kHz.

As explained above in relation to laser ablation sampling systems, the laser radiation can be directed to the sample via various optical components, and focused to a spot size (i.e. size of the beam of laser radiation when it hits the sample) of 100 µm or less, such as 50 µm or less, 25 µm or less, 20 µm or less, 15 µm or less, or 10 µm or 1 µm or less. When used for analysis of biological samples, including tissue sections, in order to analyse individual cells the spot size of laser beam used will depend on the size and spacing of the cells. For example, where the cells are tightly packed against one another (such as in a tissue section) the laser spot can have a spot size which is no larger than these cells if single cell analysis is to be conducted. This size will depend on the particular cells in a sample, but in general the laser spot for LDI will have a diameter of less than 4 µm e.g. within the range 0.1-4 µm, 0.25-3 µm, or 0.4-2 µm. In order to analyse cells at a subcellular resolution the LDI system uses a laser spot size which is no larger than these cells, and more specifically uses a laser beam spot size which can ablate material with a subcellular resolution. Sometimes, single cell analysis can be performed using a spot size larger than the size of the cell, for example where cells are spread out on the slide, with space between the cells. The particular spot size used can therefore be selected appropriately dependent upon the size of the cells being analysed. In biological samples, the cells will rarely all be of the same size, and so if subcellular resolution imaging is desired, the laser spot size should be smaller than the smallest cell, if constant spot size is maintained throughout the ion generation procedure.

Sample Chamber

The sample chamber of the LDI system shares many features in common with the sample chamber of the laser ablation-based and desorption-based sampling systems discussed above. It comprises a stage to support the sample. The stage may be a translation stage, movable in the x-y or x-y-z axes. The sample chamber will also comprise an outlet, through which material removed from the sample by the laser radiation can be directed. The outlet is connected to the detector, enabling analysis of the sample ions.

The sample chamber can be at atmospheric pressure. LDI (in particular MALDI) at atmospheric pressure is known. Here, the ions produced by LDI are assisted in their transfer from ionisation to the high vacuum region for analysis (e.g. MS detector) by a pneumatic stream of gas, for instance nitrogen (Laiko et al., 2000. Anal. Chem., 72:652-657).

In some instances, the sample chamber is held under a vacuum, or a partial vacuum. Accordingly, in some instances, the sample chamber pressure is lower than 50 000 Pa, lower than 10 000 Pa, lower than 5 000 Pa, lower than 1 000 Pa, lower than 500 Pa, lower than 100 Pa, lower than 10 Pa, lower than 1 Pa, around 0.1 Pa or less than 0.1 Pa, such as 0.01 Pa or lower. For instance, partial vacuum pressure may be around 200-700 Pa, and vacuum pressure 0.2 Pa or lower.

The selection of whether the sample pressure is at atmospheric pressure under a (partial) vacuum depends on the particular analysis being performed, as will be understood by one of skill in the art. For instance, at atmospheric pressure, sample handing is easier, and softer ionisation may be applied. Further, the presence of gas molecules may be desired so as to enable the phenomenon of collisional cooling to occur, which can be of interest when the label is a large molecule, the fragmentation of which is not desired, e.g. a molecular fragment comprising a labelling atom or combination thereof.

Holding the sample chamber under vacuum can prevent collisions between sample ions generated by LDI and other particles within the chamber. This, in some instances, may be preferred because collisions with gas molecules in the chamber may result in loss of charge from the generated sample ions. Loss of charge from the sample ions would result in their not being detected by the apparatus.

In some embodiments, the sample chamber comprises one or more gas ports arranged to enable delivery of one or more flows of gas to locations of laser desorption/ionisation on the sample during laser desorption/ionisation, such as wherein one or more gas ports is in the form of a nozzle. The gas ports (e.g. nozzle) are operable to deliver gas at the moment of desorption and ionisation, to provide collisional cooling for the desorbed ions, but only at that particular time. The rest of the time, they do not introduce gas into the chamber, thus reducing strain on the vacuum pump.

Ion Optics

The sample ion beams are captured from the sample via electrostatic plates positioned near to the sample, known in the art as the extraction electrode(s). The extraction electrode(s) remove(s) the sample ions desorbed by laser ablation from the locality of the sample. This is typically achieved by the sample, situated on a plate which also acts and an electrode (the sample electrode), and the extraction electrode(s) having a large difference in voltage potential. Depending on the polarity of the sample vis-à-vis the extraction electrodes, positively or negatively charged secondary ions are captured by the extraction electrodes.

In some embodiments, the charge across the electrodes is constant during laser desorption/ionisation. Sometimes, the charge is varied following the desorption/ionization, for instance delayed extraction, in which the accelerating voltage is applied after some short time delay following desorption/ionisation induced by a laser pulse. This technique produces time-of-flight compensation for ion energy spread, where ions with greater kinetic energy would move with greater velocity from the sample towards the detector than those with lower kinetic energy. Accordingly, this difference in velocity can cause lower resolution at the detector, because not all ions are moving at the same velocity. Accordingly, by delaying the application of the voltage across the sample and extraction electrodes, those ions with lower kinetic energy will have remained closer to the sample electrode when the accelerating voltage is applied and therefore start being accelerated at a greater potential compared to the ions farther from the target electrode. With the proper delay time, the slower ions are accelerated sufficiently to catch the ions that had higher kinetic energy after laser desorption/ionization after flying some distance from the pulsed acceleration system. Ions of the same mass-to-charge ratio will then drift through the flight tube to the detector in the same time. Accordingly, in some embodiments the sample and extraction electrodes are controllable to apply a charge across the electrodes at a set time following the laser short causing desorption/ionization of the sample.

The sample ions are then transferred to the detector via one or more further electrostatic lenses (known as transfer lenses in the art). The transfer lens(es) focus(es) the beam of sample ions into the detector. Typically, in systems with multiple transfer lenses, only one transfer lens is engaged in a given analysis. Each lens may provide a different magnification of the sample surface. Commonly, further ion manipulation components are present between the electrodes and the detector, for example one or more apertures, mass filters or sets of deflector plates. Together, the electrodes, transfer lens, and any further components, form the ion optics. Components for the production of an appropriate ion optics arrangement are available from commercial suppliers e.g. Agilent, Waters, Bruker, and can be positioned appropriately by one of skilled in the art, to deliver the ions to a detector as discussed herein below.

In addition to the detectors discussed below, as LDI can be performed so that it results in soft ionisation (e.g. ionisation without breaking of bonds in the molecules being analysed), in some instances, the detector may be a tandem MS, in which a first m/z separation is performed to select ions from the sample, before the selected ions are broken down into their fragments and undergo a second m/z separation whereupon the fragments are detected.

Methods Employing LDI

The invention also provides methods for analysing biological samples using LDI. In this analysis, the cells are labelled with labels, and these labels are then detected in the ions produced following LDI of the samples. Accordingly, the invention provides a method for performing mass cytometry on a sample comprising a plurality of cells, comprising: a. labelling a plurality of different target molecules in the sample with one or more different labels, to provide a labelled sample; b. performing laser desorption/ionisation of the sample, wherein laser desorption/ionisation is performed at multiple locations to form a plurality of individual ion clouds; and c. subjecting the ion clouds individually to mass spectrometry, whereby detection of labels in the plumes permits construction of an image of the sample, optionally wherein the multiple locations are multiple known locations.

In some embodiments, the one or more labels comprise labelling atoms. In this instance, labelling works as described below herein, whereby a member of a specific binding pair (e.g. antibody binding to a protein antigen, or a nucleic acid binding to a RNA in the sample) is attached to an elemental tag comprising one or more labelling atoms (e.g. lanthanides and actinides). The elemental tag can comprise just a single type of labelling atom (e.g. one or more atoms of a single isotope of a particular element), or can comprise different multiple kinds of labelling atom (e.g. different elements/isotopes) thereby enabling large numbers of different tags to be generated as the specific combination elements/isotopes acts as the label. In some instances, the labelling atom is detected as an elemental ion. In some embodiments, the labelling atom is emitted from the sample within a molecular ion. Thus, instead of the detection in the mass channel for the labelling atom, the presence of the labelled material in the sample will be detected in the mass channel for the molecular ion (i.e. the mass channel will simply be shifted by the mass of the molecule minus the labelling atom, vis-à-vis the labelling atom alone). In some embodiments, however, the molecule that contains the labelling atom may vary between different labelling atoms. In that case the ion containing molecular residue and labelling atom will be subjected to a fragmentation method that yields a more consistent mass peak for each reagent, such as through the application of tandem MS. The goal of all these variations and modifications to the main LDI imaging mass cytometry scheme is to maximize the number of available mass channels while simultaneously reducing the overlap between mass channels.

In some embodiments, the staining reagents can be designed to promote the release and ionization of mass tagging material and individual elemental ions or molecular ions containing a single copy of the labelling atom. The staining reagent can also be designed to promote the release and ionization of mass tagging material and individual elemental ions or molecular ions containing a several copies of the labelling atom (or combinations thereof, as discussed above). As a further alternative, the mass of the staining reagent itself can be utilized to create a detection channel for mass cytometry. In this instance, no rare-earth isotopes will be used in the staining and the mass of the staining reagent will be varied by changing the chemistry of the staining reagents to create a number of mass channels. This variation can be done with carbon, oxygen, nitrogen, sulphur, phosphorus, hydrogen and similar isotopes without the need for the rare-earth isotopes.

In some embodiments, the sample is also treated with a laser radiation absorber composition. This composition acts to enhance absorption of laser light by the sample when irradiated, and so increases transfer of energy to excite the labelling atoms (and so promote production of elemental ions or molecular ions containing a labelling atom or combination thereof).

Numbered Embodiments Relating to LDI

1. An apparatus for analysing a sample comprising: a. a sample chamber to house the sample; b. a laser, adapted to desorb and ionize material from the sample, forming ions; c. ion optics, arranged to sample the ions formed by desorption ionisation, and to direct them away from sample towards the detector; and d. a detector to receive ions from said ion optics and to analyse said ions.

2. The apparatus of embodiment 1, wherein the apparatus comprises a laser adapted to desorb and ionize material from the sample, forming elemental ions, and wherein the detector receives the elemental ions from said sampling and ionisation system and is adapted to analyse said elemental ions.

3. The apparatus of any preceding embodiment, wherein the apparatus comprises a laser adapted to desorb and ionize material from the sample, forming molecular ions, and wherein the detector receives the molecular ions from said sampling and ionisation system and is adapted to detect said molecular ions.

4. The apparatus of any preceding embodiment, wherein the apparatus comprises a laser adapted to desorb and ionize material from the sample, forming both elemental and molecular ions, and wherein the detector receives the ions from said sampling and ionisation system and is adapted to detect both said elemental and said molecular ions.

5. The apparatus of any preceding embodiment, wherein the laser is a deep UV laser, such as a laser emitting radiation at 193 nm, 213 nm or 266 nm.

6. The apparatus of any preceding embodiment wherein the laser is a femtosecond laser.

7. The apparatus of any preceding embodiment, wherein desorption ionisation occurs in the sample chamber under a vacuum, a partial vacuum or at atmospheric pressure.

8. The apparatus of any preceding embodiment, wherein the sample chamber comprises one or more gas ports arranged to enable delivery of one or more pulses of gas to locations of laser desorption ionisation on the sample during laser desorption ionisation, such as wherein one or more gas ports is in the form of a nozzle.

9. The apparatus according to embodiment 8, wherein the one or more gas ports is arranged so as to enable the one or more pulses of gas to collisionally cool ions generated from a sample by laser radiation from the laser.

10. A method for performing mass cytometry on a sample comprising a plurality of cells, comprising: a. labelling a one or more different target molecules in the sample with one or more mass tags, to provide a labelled sample; b. performing laser desorption ionisation of the sample, wherein laser desorption ionisation is performed at multiple known locations to form a plurality of ion clouds; and c. subjecting the ion clouds to mass spectrometry, whereby detection of ions from the one or more mass tags in the clouds permits construction of an image of the sample.

11. The method according to embodiment 10, wherein the plurality of ion clouds is a plurality of individual ion clouds, each individual ion cloud being formed from laser desorption ionisation at a known location, and wherein the subjecting the ion clouds to mass spectrometry comprises subjecting individual ion clouds to mass spectrometry.

12. The method according to embodiment 10 or 11, wherein each different target is bound by a different specific binding pair member (SBP), and each different SBP is linked to a mass tag, such that each target is labelled with a specific mass tag.

13. The method according to any one of embodiments 10-12, further comprising, prior to step a. or between steps a. and b., the step of treating the sample with an ionization promoter composition.

14. The method according to embodiment 13, wherein the ionization promoter composition promotes ionization of labelling atoms and/or molecular ions containing the labelling atoms.

15. The method according to any one of embodiments 10-14, further comprising, prior to step a. or between steps a. and b., the step of treating the sample with laser radiation absorber composition.

2. Mass Detector System

Exemplary types of mass detector system include quadrupole, time of flight (TOF), magnetic sector, high resolution, single or multicollector based mass spectrometers.

The time taken to analyse the ionised material will depend on the type of mass analyser which is used for detection of ions. For example, instruments which use Faraday cups are generally too slow for analysing rapid signals. Overall, the desired imaging speed, resolution and degree of multiplexing will dictate the type(s) of mass analyser which should be used (or, conversely, the choice of mass analyser will determine the speed, resolution and multiplexing which can be achieved).

Mass spectrometry instruments that detect ions at only one mass-to-charge ratio (m/Q, commonly referred to as m/z in MS) at a time, for example using a point ion detector, will give poor results in imaging detecting. Firstly, the time taken to switch between mass-to-charge ratios limits the speed at which multiple signals can be determined, and secondly, if ions are at low abundance then signals can be missed when the instrument is focused on other mass-to-charge ratios. Thus it is preferred to use a technique which offers substantially simultaneous detection of ions having different m/Q values.

Detector Types

Quadrupole Detector

Quadrupole mass analysers comprise four parallel rods with a detector at one end. An alternating RF potential and fixed DC offset potential is applied between one pair of rods and the other so that one pair of rods (each of the rods opposite each other) has an opposite alternative potential to the other pair of rods. The ionised sample is passed through the middle of the rods, in a direction parallel to the rods and towards the detector. The applied potentials affect the trajectory of the ions such that only ions of a certain mass-charge ratio will have a stable trajectory and so reach the detector. Ions of other mass-charge ratios will collide with the rods.

Magnetic Sector Detector

In magnetic sector mass spectrometry, the ionised sample is passed through a curved flight tube towards an ion detector. A magnetic field applied across the flight tube causes the ions to deflect from their path. The amount of deflection of each ion is based on the mass to charge ratio of each ion and so only some of the ions will collide with the detector—the other ions will be deflected away from the detector. In multicollector sector field instruments, an array of detectors is be used to detect ions of different masses. In some instruments, such as the ThermoScientific Neptune Plus, and Nu Plasma II, the magnetic sector is combined with an electrostatic sector to provide a double-focusing magnetic sector instrument that analyses ions by kinetic energy, in addition to mass to charge ratio. In particular those multidetectors having a Mattauch-Herzog geometry can be used (e.g. the SPECTRO MS, which can simultaneously record all elements from lithium to uranium in a single measurement using a semiconductor direct charge detector). These instruments can measure multiple m/Q signals substantially simultaneously. Their sensitivity can be increased by including electron multipliers in the detectors. Array sector instruments are always applicable, however, because, although they are useful for detecting increasing signals, they are less useful when signal levels are decreasing, and so they are not well suited in situations where labels are present at particularly highly variable concentrations.

Time of Flight (TOF) Detector

A time of flight mass spectrometer comprises a sample inlet, an acceleration chamber with a strong electric field applied across it, and an ion detector. A packet of ionised sample molecules is introduced through the sample inlet and into the acceleration chamber. Initially, each of the ionised sample molecules has the same kinetic energy but as the ionised sample molecules are accelerated through the acceleration chamber, they are separated by their masses, with the lighter ionised sample molecules travelling faster than heaver ions. The detector then detects all the ions as they arrive. The time taking for each particle to reach the detector depends on the mass to charge ratio of the particle.

Thus a TOF detector can quasi-simultaneously register multiple masses in a single sample. In theory TOF techniques are not ideally suited to ICP ion sources because of their space charge characteristics, but TOF instruments can in fact analyse an ICP ion aerosol rapidly enough and sensitively enough to permit feasible single-cell imaging. Whereas TOF mass analyzers are normally unpopular for atomic analysis because of the compromises required to deal with the effects of space charge in the TOF accelerator and flight tube, tissue imaging according to the subject disclosure can be effective by detecting only the labelling atoms, and so other atoms (e.g. those having an atomic mass below 100) can be removed. This results in a less dense ion beam, enriched in the masses in (for example) the 100-250 dalton region, which can be manipulated and focused more efficiently, thereby facilitating TOF detection and taking advantage of the high spectral scan rate of TOF. Thus rapid imaging can be achieved by combining TOF detection with choosing labelling atoms that are uncommon in the sample and ideally having masses above the masses seen in an unlabelled sample e.g. by using the higher mass transition elements. Using a narrower window of label masses thus means that TOF detection to be used for efficient imaging.

Suitable TOF instruments are available from Tofwerk, GBC Scientific Equipment (e.g. the Optimass 9500 ICP-TOFMS), and Fluidigm Canada (e.g. the CyTOF™ and CyTOF™2 instruments). These CyTOF™ instruments have greater sensitivity than the Tofwerk and GBC instruments and are known for use in mass cytometry because they can rapidly and sensitively detect ions in the mass range of rare earth metals (particularly in the m/Q range of 100-200; see Bandura et al. (2009; Anal. Chem., 81:6813-22). Thus these are preferred instruments for use with the disclosure, and they can be used for imaging with the instrument settings already known in the art e.g. Bendall et al. (2011; Science 332, 687-696) & Bodenmiller et al. (2012; Nat. Biotechnol. 30:858-867). Their mass analysers can detect a large number of markers quasi-simultaneously at a high mass-spectrum acquisition frequency on the timescale of high-frequency laser ablation or sample desorption. They can measure the abundance of labelling atoms with a detection limit of about 100 per cell, permitting sensitive construction of an image of the tissue sample. Because of these features, mass cytometry can now be used to meet the sensitivity and multiplexing needs for tissue imaging at subcellular resolution. By combining the mass cytometry instrument with a high-resolution laser ablation sampling system and a rapid-transit low-dispersion sample chamber it has been possible to permit construction of an image of the tissue sample with high multiplexing on a practical timescale.

The TOF may be coupled with a mass-assignment corrector. The vast majority of ionisation events generate $M^+$ ions, where a single electron has been knocked out of the atom. Because of the mode of operation of the TOF MS there is sometimes some bleeding (or cross-talk) of the ions of one mass (M) into the channels for neighbouring masses (M±1), in particular where a large number of ions of mass M are entering the detector (i.e. ion counts which are high, but not so high that an ion deflector positioned between the sampling ionisation system and MS would prevent them from entering the MS, if the apparatus were to comprise such an ion deflector). As the arrival time of each $M^+$ ion at the detector follows a probability distribution about a mean (which is known for each M), when the number of ions at mass $M^+$ is high, then some will arrive at times that would normally be associated with the $M-1^+$ or $M+1^+$ ions. However, as each ion has a known distribution curve upon entering the TOF MS, based on the peak in the mass M channel it is possible to determine, the overlap of ions of mass M into the M±1 channels (by comparison to the known peak shape). The calculation is particularly applicable for TOF MS, because the peak of ions detected in a TOF MS is asymmetrical. Accordingly it is therefore possible to correct the readings for the M−1, M and M+1 channels to appropriately assign all of the detected ions to the M channel. Such corrections have particular use in correcting imaging data due to the nature of the large packets of ions produced by sampling and ionisation systems such as those disclosed herein involving laser ablation (or desorption as discussed below) as the techniques for removing material from the sample. Programs and methods for improving the quality of data by de-convoluting the data from TOF MS are discussed in WO2011/098834, U.S. Pat. No. 8,723,108 and WO2014/091243.

Dead-Time Corrector

As noted above, signals in the MS are detected on the basis of collisions between ions and the detector, and the release of electrons from the surface of the detector hit by the ions. When a high count of ions is detected by the MS resulting in the release of a large number of electrons, the detector of the MS can become temporarily fatigued, with the result that the analog signal output from the detector is temporarily depressed for one or more of the subsequent packets of ions. In other words, a particularly high count of ions in a packet of ionised sample material causes a lot of electrons to be released from the detector surface and secondary multiplier in the process of detecting the ions from that packet of ionised sample material, meaning that fewer electrons are available to be released when the ions in subsequent packets of ionised sample material hit the detector, until the electrons in the detector surface and secondary amplifier are replenished.

Based on a characterisation of the behaviour of the detector, it is possible to compensate for this dead-time phenomenon. A first step is to analyse the ion peak in the analog signal resulting from the detection of the nth packet of ionised sample material by the detector. The magnitude of the peak may be determined by the height of the peak, by the area of the peak, or by a combination of peak height and peak area.

The magnitude of the peak is then compared to see if it exceeds a predetermined threshold. If the magnitude is below this threshold, then no correction is necessary. If the magnitude is above the threshold, then correction of the digital signal from at least one subsequent packet of ionised sample material will be performed (at least the (n+1)th packet of ionised sample material, but possibly further packets of ionised sample material, such as (n+2)th, (n+3)th, (n+4)th etc.) to compensate for the temporary depression of the analog signal from these packets of ionised sample material resulting from the fatiguing of the detector caused by the nth packet of ionised sample material. The greater the magnitude of the peak of the nth packet of ionised sample material, the more peaks from subsequent packets of ionised sample material will need to be corrected and the magnitude of correction will need to be greater. Methods for correcting such phenomena are discussed in Stephan et al. (1994; Vac. Sci. Technol. 12:405), Tyler and Peterson (2013; Surf Interface Anal. 45:475-478), Tyler (2014; Surf Interface Anal. 46:581-590), WO2006/090138 and U.S. Pat. No. 6,229,142, and these methods can be applied by the dead-time corrector to the data, as described herein.

Analyser Apparatus Based on Optical Emission Spectra Detection

1. Sampling and Ionisation Systems a. Laser Ablation Based Sampling and Ionising System The laser ablation sampling system described above in relation to mass-based analysers can be employed in an OES detector-based system. For detection of atomic emission spectra, most preferably, an ICP is used to ionise the sample material removed from the sample, but any hard ionisation technique that can produce elemental ions can be used.

As appreciated by one of skill in the art, certain optional further components of the laser ablation based sampling and ionising system above, described in relation to avoiding overload of the mass-based detector, may not be applicable to all OES detector-based systems, and would not be incorporated, if inappropriate, by the skilled artisan.

b. Desorption Based Sampling and Ionising System

The desorption-based sampling system described above in relation to mass-based analysers can be employed in an OES detector-based system. For detection of atomic emission spectra, most preferably, an ICP is used to ionise the sample material removed from the sample, but any hard ionisation technique that can produce elemental ions can be used.

As appreciated by one of skill in the art, certain optional further components of the desorption based sampling and ionising system above, described in relation to avoiding overload of the mass-based detector, may not be applicable to all OES detector-based systems, and would not be incorporated, if inappropriate, by the skilled artisan.

2. Photodetectors

Exemplary types of photodetectors include photomultipliers and charged-coupled devices (CODs). Photodetetors may be used to image the sample and/or identify a feature/region of interest prior to imaging by elemental mass spectrometry.

Photomultipliers comprise a vacuum chamber comprising a photocathode, several dynodes, and an anode. A photon incident on the photocathode causes the photocathode to emit an electron as a consequence of the photoelectric effect. The electron is multiplied by the dynodes due to the process of secondary emission to produce a multiplied electron current, and then the multiplied electron current is detected by the anode to provide a measure of detection of electromagnetic radiation incident on the photocathode. Photomultipliers are available from, for example, ThorLabs.

A CCD comprises a silicon chip containing an array of light-sensitive pixels. During exposure to light, each pixel generates an electric charge in proportion to the intensity of light incident on the pixel. After the exposure, a control circuit causes a sequence of transfers of electric charge to produce a sequence of voltages. These voltages can then be analysed to produce an image. Suitable CCDs are available from, for example, Cell Biosciences.

Constructing an Image

The apparatus above can provide signals for multiple atoms in packets of ionised sample material removed from the sample. Detection of an atom in a packet of sample material reveals its presence at the position of ablation, be that because the atom is naturally present in the sample or because the atom has been localised to that location by a labelling reagent. By generating a series of packets of ionised sample material from known spatial locations on the sample's surface the detector signals reveal the location of the atoms on the sample, and so the signals can be used to construct an image of the sample. By labelling multiple targets with distinguishable labels it is possible to associate the location of labelling atoms with the location of cognate targets, so the method can build complex images, reaching levels of multiplexing which far exceed those achievable using traditional techniques such as fluorescence microscopy.

Assembly of signals into an image will use a computer and can be achieved using known techniques and software packages. For instance, the GRAPHIS package from Kylebank Software may be used, or other packages such as TERAPLOT can also be used. Imaging using MS data from techniques such as MALDI-MSI is known in the art e.g. Robichaud et al. (2013; J Am Soc Mass Spectrom 24 5:718-21) discloses the 'MSiReader' interface to view and analyze MS imaging files on a Matlab platform, and Klinkert et al. (2014; Int J Mass Spectrom http://dx.doi.org/10.1016/j.ijms.2013.12.012) discloses two software instruments for rapid data exploration and visualization of both 2D and 3D MSI data sets in full spatial and spectral resolution e.g. the 'Datacube Explorer' program.

Images obtained using the methods disclosed herein can be further analysed e.g. in the same way that IHC results are analysed. For instance, the images can be used for delineating cell sub-populations within a sample, and can provide information useful for clinical diagnosis. Similarly, SPADE analysis can be used to extract a cellular hierarchy from the high-dimensional cytometry data which methods of the disclosure provide (Qiu et al. (2011; Nat. Biotechnol. 29:886-91)).

Samples

Certain aspects of the disclosure provides a method of imaging a biological sample. Such samples can comprise a plurality of cells which can be subjected to imaging mass cytometry (IMC) in order to provide an image of these cells in the sample. In general, the invention can be used to analyse tissue samples which are now studied by immunohistochemistry (IHC) techniques, but with the use of labelling atoms which are suitable for detection by mass spectrometry (MS) or optical emission spectrometry (OES).

Any suitable tissue sample can be used in the methods described herein. For example, the tissue can include tissue from one or more of epithelium, muscle, nerve, skin, intestine, pancreas, kidney, brain, liver, blood (e.g. a blood smear), bone marrow, buccal swipes, cervical swipes, or any other tissue. The biological sample may be an immortalized cell line or primary cells obtained from a living subject. For diagnostic, prognostic or experimental (e.g., drug development) purposes the tissue can be from a tumor. In some embodiments, a sample may be from a known tissue, but it might be unknown whether the sample contains tumor cells. Imaging can reveal the presence of targets which indicate the presence of a tumor, thus facilitating diagnosis. Tissue from a tumor may comprise immune cells that are also characterized by the subject methods, and may provide insight into the tumor biology. The tissue sample may comprise formalin-fixed, paraffin-embedded (FFPE) tissue. The tissues can be obtained from any living multicellular organism, such as a mammal, an animal research model (e.g., of a particular disease, such as an immunodeficient rodent with a human tumor xenograft), or a human patient.

The tissue sample may be a section e.g. having a thickness within the range of 2-10 µm, such as between 4-6 µm. Techniques for preparing such sections are well known from the field of IHC e.g. using microtomes, including dehydration steps, fixation, embedding, permeabilization, sectioning etc. Thus, a tissue may be chemically fixed and then sections can be prepared in the desired plane. Cryosectioning or laser capture microdissection can also be used for preparing tissue samples. Samples may be permeabilised e.g. to permit uptake of reagents for labelling of intracellular targets (see above).

The size of a tissue sample to be analysed will be similar to current IHC methods, although the maximum size will be dictated by the laser ablation apparatus, and in particular by the size of sample which can fit into its sample chamber. A size of up to 5 mm×5 mm is typical, but smaller samples (e.g. 1 mm×1 mm) are also useful (these dimensions refer to the size of the section, not its thickness).

In addition to being useful for imaging tissue samples, the disclosure can instead be used for imaging of cellular samples such as monolayers of adherent cells or of cells which are immobilised on a solid surface (as in conventional immunocytochemistry). These embodiments are particularly useful for the analysis of adherent cells that cannot be easily solubilized for cell-suspension mass cytometry. Thus, as well as being useful for enhancing current immunohistochemical analysis, the disclosure can be used to enhance immunocytochemistry.

Sample Carrier

In certain embodiments, the sample may be immobilized on a solid support (i.e. a sample carrier), to position it for imaging mass spectrometry. The solid support may be optically transparent, for example made of glass or plastic. Where the sample carrier is optically transparent, it enables ablation of the sample material through the support. Sometimes, the sample carrier will comprise features that act as reference points for use with the apparatus and methods described herein, for instance to allow the calculation of the relative position of features/regions of interest that are to be ablated or desorbed and analysed. The reference points may be optically resolvable, or may be resolvable by mass analysis.

Target Elements

In imaging mass spectrometry, the distribution of one or more target elements (i.e., elements or elemental isotopes) may be of interest. In certain aspects, target elements are labelling atoms as described herein. A labelling atom may be directly added to the sample alone or covalently bound to or within a biologically active molecule. In certain embodiments, labelling atoms (e.g., metal tags) may be conjugated to a member of a specific binding pair (SBP), such as an antibody (that binds to its cognate antigen), aptamer or oligonucleotide for hybridizing to a DNA or RNA target, as described in more detail below. Labelling atoms may be attached to an SBP by any method known in the art. In certain aspects, the labelling atoms are a metal element, such as a lanthanide or transition element or another metal tag as described herein. The metal element may have a mass greater than 60 amu, greater than 80 amu, greater than 100 amu, or greater than 120 amu. Mass spectrometers described herein may deplete elemental ions below the masses of the metal elements, so that abundant lighter elements do not create space-charge effects and/or overwhelm the mass detector.

Labelling of the Tissue Sample

The disclosure produces images of samples which have been labelled with labelling atoms, for example a plurality of different labelling atoms, wherein the labelling atoms are detected by an apparatus capable of sampling specific, preferably subcellular, areas of a sample (the labelling atoms therefore represent an elemental tag). The reference to a plurality of different atoms means that more than one atomic species is used to label the sample. These atomic species can be distinguished using a mass detector (e.g. they have different m/Q ratios), such that the presence of two different labelling atoms within a plume gives rise to two different MS signals. The atomic species can also be distinguished using an optical spectrometer (e.g. different atoms have different emission spectra), such that the presence of two different labelling atoms within a plume gives rise to two different emission spectral signals.

Mass Tagged Reagents

Mass-tagged reagents as used herein comprise a number of components. The first is the SBP. The second is the mass tag. The mass tag and the SBP are joined by a linker, formed at least in part of by the conjugation of the mass tag and the SBP. The linkage between the SBP and the mass tag may also comprise a spacer. The mass tag and the SBP can be conjugated together by a range of reaction chemistries. Exemplary conjugation reaction chemistries include thiol maleimide, NHS ester and amine, or click chemistry reactivities (preferably Cu(I)-free chemistries), such as strained alkyne and azide, strained alkyne and nitrone and strained alkene and tetrazine.

Mass Tags

The mass tag used in the present invention can take a number of forms. Typically, the tag comprises at least one labelling atom. A labelling atom is discussed herein below.

Accordingly, in its simplest form, the mass tag may comprise a metal-chelating moiety which is a metal-chelating group with a metal labelling atom co-ordinated in the ligand. In some instances, detecting only a single metal atom per mass tag may be sufficient. However, in other instances, it may be desirable of each mass tag to contain more than one labelling atom. This can be achieved in a number of ways, as discussed below.

A first means to generate a mass tag that can contain more than one labelling atom is the use of a polymer comprising metal-chelating ligands attached to more than one subunit of the polymer. The number of metal-chelating groups capable of binding at least one metal atom in the polymer can be between approximately 1 and 10,000, such as 5-100, 10-250, 250-5,000, 500-2,500, or 500-1,000. At least one metal atom can be bound to at least one of the metal-chelating groups. The polymer can have a degree of polymerization of between approximately 1 and 10,000, such as 5-100, 10-250, 250-5,000, 500-2,500, or 500-1,000. Accordingly, a polymer based mass tag can comprise between approximately 1 and 10,000, such as 5-100, 10-250, 250-5,000, 500-2,500, or 500-1,000 labelling atoms.

The polymer can be selected from the group consisting of linear polymers, copolymers, branched polymers, graft copolymers, block polymers, star polymers, and hyperbranched polymers. The backbone of the polymer can be derived from substituted polyacrylamide, polymethacrylate, or polymethacrylamide and can be a substituted derivative of a homopolymer or copolymer of acrylamides, methacrylamides, acrylate esters, methacrylate esters, acrylic acid or methacrylic acid. The polymer can be synthesised from the group consisting of reversible addition fragmentation polymerization (RAFT), atom transfer radical polymerization (ATRP) and anionic polymerization. The step of providing the polymer can comprise synthesis of the polymer from compounds selected from the group consisting of N-alkyl acrylamides, N,N-dialkyl acrylamides, N-aryl acrylamides, N-alkyl methacrylamides, N,N-dialkyl methacrylamides, Naryl methacrylamides, methacrylate esters, acrylate esters and functional equivalents thereof.

The polymer can be water soluble. This moiety is not limited by chemical content. However, it simplifies analysis if the skeleton has a relatively reproducible size (for example, length, number of tag atoms, reproducible dendrimer character, etc.). The requirements for stability, solubility, and non-toxicity are also taken into consideration. Thus, the preparation and characterization of a functional water soluble polymer by a synthetic strategy that places many functional groups along the backbone plus a different reactive group (the linking group), that can be used to attach the polymer to a molecule (for example, an SBP), through a linker and optionally a spacer. The size of the polymer is controllable by controlling the polymerisation reaction. Typically the size of the polymer will be chosen so as the radiation of gyration of the polymer is as small as possible, such as between 2 and 11 nanometres. The length of an IgG antibody, an exemplary SBP, is approximately 10 nanometres, and therefore an excessively large polymer tag in relation to the size of the SBP may sterically interfere with SBP binding to its target.

The metal-chelating group that is capable of binding at least one metal atom can comprise at least four acetic acid groups. For instance, the metal-chelating group can be a diethylenetriaminepentaacetate (DTPA) group or a 1,4,7,10-tetraazacyclododecane-1,4,7,10-tetraacetic acid (DOTA) group. Alternative groups include Ethylenediaminetetraacetic acid (EDTA) and ethylene glycol-bis(β-aminoethyl ether)-N,N,N',N'-tetraacetic acid (EGTA)

The metal-chelating group can be attached to the polymer through an ester or through an amide. Examples of suitable metal-chelating polymers include the X8 and DM3 polymers available from Fluidigm Canada, Inc.

The polymer can be water soluble. Because of their hydrolytic stability, N-alkyl acrylamides, N-alkyl methacrylamides, and methacrylate esters or functional equivalents can be used. A degree of polymerization (DP) of approximately 1 to 1000 (1 to 2000 backbone atoms) encompasses most of the polymers of interest. Larger polymers are in the scope of the invention with the same functionality and are possible as would be understood by practitioners skilled in the art. Typically the degree of polymerization will be between 1 and 10,000, such as 5-100, 10-250, 250-5,000, 500-2,500, or 500-1,000. The polymers may be amenable to synthesis by a route that leads to a relatively narrow polydispersity. The polymer may be synthesized by atom transfer radical polymerization (ATRP) or reversible addition-fragmentation (RAFT) polymerization, which should lead to values of Mw (weight average molecular weight)/Mn (number average molecular weight) in the range of 1.1 to 1.2. An alternative strategy involving anionic polymerization, where polymers with Mw/Mn of approximately 1.02 to 1.05 are obtainable. Both methods permit control over end groups, through a choice of initiating or terminating agents. This allows synthesizing polymers to which the linker can be attached. A strategy of preparing polymers containing functional pendant groups in the repeat unit to which the liganded transition metal unit (for example a Ln unit) can be attached in a later step can be adopted. This embodiment has several advantages. It avoids complications that might arise from carrying out polymerizations of ligand containing monomers.

To minimize charge repulsion between pendant groups, the target ligands for ($M^{3+}$) should confer a net charge of −1 on the chelate.

Polymers that be used in the invention include:
random copolymer poly(DMA-co-NAS): The synthesis of a 75/25 mole ratio random copolymer of N-acryloxysuccinimide (NAS) with N,N-dimethyl acrylamide (DMA) by RAFT with high conversion, excellent molar mass control in the range of 5000 to 130,000, and with Mw/Mn≈1.1 is reported in Relógio et al. (2004) (Polymer, 45, 8639-49). The active NHS ester is reacted with a metal-chelating group bearing a reactive amino group to yield the metal-chelating copolymer synthesised by RAFT polymerization.
poly(NMAS): NMAS can be polymerised by ATRP, obtaining polymers with a mean molar mass ranging from 12 to 40 KDa with Mw/Mn of approximately 1.1 (see e.g. Godwin et al., 2001; Angew. Chem.Int.Ed, 40:594-97).

poly(MAA): polymethacrylic acid (PMAA) can be prepared by anionic polymerization of its t-butyl or trimethylsilyl (TMS) ester.

poly(DMAEMA): poly(dimethylaminoethyl methacrylate) (PDMAEMA) can be prepared by ATRP (see Wang et al, 2004, J.Am.Chem.Soc, 126, 7784-85). This is a well-known polymer that is conveniently prepared with mean Mn values ranging from 2 to 35 KDa with Mw/Mn of approximately 1.2 This polymer can also be synthesized by anionic polymerization with a narrower size distribution.

polyacrylamide, or polymethacrylamide.

The metal-chelating groups can be attached to the polymer by methods known to those skilled in the art, for example, the pendant group may be attached through an ester or through an amide. For instance, to a methylacrylate based polymer, the metal-chelating group can be attached to the polymer backbone first by reaction of the polymer with ethylenediamine in methanol, followed by subsequent reaction of DTPA anhydride under alkaline conditions in a carbonate buffer.

A second means is to generate nanoparticles which can act as mass tags. A first pathway to generating such mass tags is the use of nanoscale particles of the metal which have been coated in a polymer. Here, the metal is sequestered and shielded from the environment by the polymer, and does not react when the polymer shell can be made to react e.g. by functional groups incorporated into the polymer shell. The functional groups can be reacted with linker components (optionally incorporating a spacer) to attach click chemistry reagents, so allowing this type of mass tag to plug in to the synthetics strategies discussed above in a simple, modular fashion.

Grafting-to and grafting-from are the two principle mechanism for generating polymer brushes around a nanoparticle. In grafting to, the polymers are synthesised separately, and so synthesis is not constrained by the need to keep the nanoparticle colloidally stable. Here reversible additionfragmentation chain transfer (RAFT) synthesis has excelled due to a large variety of monomers and easy functionalization. The chain transfer agent (CTA) can be readily used as functional group itself, a functionalized CTA can be used or the polymer chains can be post-functionalized. A chemical reaction or physisorption is used to attach the polymers to the nanoparticle. One drawback of grafting-to is the usually lower grafting density, due to the steric repulsion of the coiled polymer chains during attachment to the particle surface. All grafting-to methods suffer from the drawback that a rigorous workup is necessary to remove the excess of free ligand from the functionalized nanocomposite particle. This is typically achieved by selective precipitation and centrifugation. In the grafting-from approach molecules, like initiators for atomic transfer radical polymerization (ATRP) or CTAs for (RAFT) polymerizations, are immobilized on the particle surface. The drawbacks of this method are the development of new initiator coupling reactions. Moreover, contrary to grafting-to, the particles have to be colloidally stable under the polymerization conditions.

An additional means of generating a mass tag is via the use of doped beads. Chelated lanthanide (or other metal) ions can be employed in miniemulsion polymerization to create polymer particles with the chelated lanthanide ions embedded in the polymer. The chelating groups are chosen, as is known to those skilled in the art, in such a way that the metal chelate will have negligible solubility in water but reasonable solubility in the monomer for miniemulsion polymerization. Typical monomers that one can employ are styrene, methylstyrene, various acrylates and methacrylates, among others as is known to those skilled in the art. For mechanical robustness, the metal-tagged particles have a glass transition temperature (Tg) above room temperature. In some instances, core-shell particles are used, in which the metal-containing particles prepared by miniemulsion polymerization are used as seed particles for a seeded emulsion polymerization to control the nature of the surface functionality. Surface functionality can be introduced through the choice of appropriate monomers for this secondstage polymerization. Additionally, acrylate (and possible methacrylate) polymers are advantageous over polystyrene particles because the ester groups can bind to or stabilize the unsatisfied ligand sites on the lanthanide complexes. An exemplary method for making such doped beads is: (a) combining at least one labelling atom-containing complex in a solvent mixture comprising at least one organic monomer (such as styrene and/or methyl methacrylate in one embodiment) in which the at least one labelling atom-containing complex is soluble and at least one different solvent in which said organic monomer and said at least one labelling atom-containing complex are less soluble, (b) emulsifying the mixture of step (a) for a period of time sufficient to provide a uniform emulsion; (c) initiating polymerization and continuing reaction until a substantial portion of monomer is converted to polymer; and (d) incubating the product of step (c) for a period of time sufficient to obtain a latex suspension of polymeric particles with the at least one labelling atom-containing complex incorporated in or on the particles therein, wherein said at least one labelling atom-containing complex is selected such that upon interrogation of the polymeric mass tag, a distinct mass signal is obtained from said at least one labelling atom. By the use of two or more complexes comprising different labelling atoms, doped beads can be made comprising two or more different labelling atoms. Furthermore, controlling the ration of the complexes comprising different labelling atoms, allows the production of doped beads with different ratios of the labelling atoms. By use of multiple labelling atoms, and in different radios, the number of distinctively identifiable mass tags is increased. In core-shell beads, this may be achieved by incorporating a first labelling atom-containing complex into the core, and a second labelling atom-containing complex into the shell.

A yet further means is the generation of a polymer that include the labelling atom in the backbone of the polymer rather than as a co-ordinated metal ligand. For instance, Carerra and Seferos (Macromolecules 2015, 48, 297-308) disclose the inclusion of tellurium into the backbone of a polymer. Other polymers incorporating atoms capable as functioning as labelling atoms tin-, antimony- and bismuth-incorporating polymers. Such molecules are discussed inter alia in Priegert et al., 2016 (Chem. Soc. Rev., 45, 922-953).

Thus the mass tag can comprise at least two components: the labelling atoms, and a polymer, which either chelates, contains or is doped with the labelling atom. In addition, the mass tag comprises an attachment group (when not-conjugated to the SBP), which forms part of the chemical linkage between the mass tag and the SBP following reaction of the two components, in a click chemistry reaction in line with the discussion above.

A polydopamine coating can be used as a further way to attach SBPs to e.g. doped beads or nanoparticles. Given the range of functionalities in polydopamine, SBPs can be conjugated to the mass tag formed from a PDA coated bead or particle by reaction of e.g. amine or sulfhydryl groups on the SBP, such as an antibody. Alternatively, the functionalities on the PDA can be reacted with reagents such as bifunctional linkers which introduce further functionalities in turn for reaction with the SBP. In some instances, the linkers can contain spacers, as discussed below. These spacers increase the distance between the mass tag and the SBP, minimising steric hindrance of the SBP. Thus the invention comprises a mass-tagged SBP, comprising an SBP and a mass tag comprising polydopamine, wherein the polydopamine comprises at least part of the link between the SBP and the mass tag. Nanoparticles and beads, in particular polydopamine coated nanoparticles and beads, may be useful for signal enhancement to detect low abundance targets, as they can have thousands of metal atoms and may have multiple copies of the same affinity reagent. The affinity reagent could be a secondary antibody, which could further boost signal.

Labelling Atom

Labelling atoms that can be used with the disclosure include any species that are detectable by MS or OES and that are substantially absent from the unlabelled tissue sample. Thus, for instance, $^{12}C$ atoms would be unsuitable as labelling atoms because they are naturally abundant, whereas $^{11}C$ could in theory be used for MS because it is an artificial isotope which does not occur naturally. Often the labelling atom is a metal. In preferred embodiments, however, the labelling atoms are transition metals, such as the rare earth metals (the 15 lanthanides, plus scandium and yttrium). These 17 elements (which can be distinguished by OES and MS) provide many different isotopes which can be easily distinguished (by MS). A wide variety of these elements are available in the form of enriched isotopes e.g. samarium has 6 stable isotopes, and neodymium has 7 stable isotopes, all of which are available in enriched form. The 15 lanthanide elements provide at least 37 isotopes that have non-redundantly unique masses. Examples of elements that are suitable for use as labelling atoms include Lanthanum (La), Cerium (Ce), Praseodymium (Pr), Neodymium (Nd), Promethium (Pm), Samarium (Sm), Europium (Eu), Gadolinium, (Gd), Terbium (Tb), Dysprosium (Dy), Holmium (Ho), Erbium (Er), Thulium (Tm), Ytterbium (Yb), Lutetium (Lu), Scandium (Sc), and Yttrium (Y). In addition to rare earth metals, other metal atoms are suitable for detection e.g. gold (Au), platinum (Pt), iridium (Ir), rhodium (Rh), bismuth (Bi), etc. The use of radioactive isotopes is not preferred as they are less convenient to handle and are unstable e.g. Pm is not a preferred labelling atom among the lanthanides.

In order to facilitate time-of-flight (TOF) analysis (as discussed herein) it is helpful to use labelling atoms with an atomic mass within the range 80-250 e.g. within the range 80-210, or within the range 100-200. This range includes all of the lanthanides, but excludes Sc and Y. The range of 100-200 permits a theoretical 101-plex analysis by using different labelling atoms, while taking advantage of the high spectral scan rate of TOF MS. As mentioned above, by choosing labelling atoms whose masses lie in a window above those seen in an unlabelled sample (e.g. within the range of 100-200), TOF detection can be used to provide rapid imaging at biologically significant levels.

Various numbers of labelling atoms can be attached to a single SBP member dependent upon the mass tag used (and so the number of labelling atoms per mass tag) and the number of mass tags that are attached to each SBP). Greater sensitivity can be achieved when more labelling atoms are attached to any SBP member. For example, greater than 10, 20, 30, 40, 50, 60, 70, 80, 90 or 100 labelling atoms can be attached to a SBP member, such as up to 10,000, for instance as 5-100, 10-250, 250-5,000, 500-2,500, or 500-1,000 labelling atoms. As noted above, monodisperse polymers containing multiple monomer units may be used, each containing a chelator such as diethylenetriaminepentaacetic acid (DTPA) or DOTA. DTPA, for example, binds 3+ lanthanide ions with a dissociation constant of around $10^{-6}$ M. These polymers can terminate in a thiol which can be used for attaching to a SBP via reaction of that with a maleimide to attach a click chemistry reactivity in line with those discussed above. Other functional groups can also be used for conjugation of these polymers e.g. amine-reactive groups such as N-hydroxy succinimide esters, or groups reactive against carboxyls or against an antibody's glycosylation. Any number of polymers may bind to each SBP. Specific examples of polymers that may be used include straight-chain ("X8") polymers or third-generation dendritic ("DN3") polymers, both available as MaxPar™ reagents. Use of metal nanoparticles can also be used to increase the number of atoms in a label, as also discussed above.

In some embodiments, all labelling atoms in a mass tag are of the same atomic mass. Alternatively, a mass tag can comprise labelling atoms of differing atomic mass. Accordingly, in some instances, a labelled sample may be labelled with a series of mass-tagged SBPs each of which comprises just a single type of labelling atom (wherein each SBP binds its cognate target and so each kind of mass tag is localised on the sample to a specific e.g. antigen). Alternatively, in some instance, a labelled sample may be labelled with a series of mass-tagged SBPs each of which comprises a mixture of labelling atoms. In some instances, the mass-tagged SBPs used to label the sample may comprise a mix of those with single labelling atom mass tags and mixes of labelling atoms in their mass tags.

Spacer

As noted above, in some instances, the SBP is conjugated to a mass tag through a linker which comprises a spacer. There may be a spacer between the SBP and the click chemistry reagent (e.g. between the SBP and the strained cycloalkyne (or azide); strained cycloalkene (or tetrazine); etc.). There may be a spacer between the between the mass tag and the click chemistry reagent (e.g. between the mass tag and the azide (or strained cycloalkyne); tetrazine (or strained cycloalkene); etc.). In some instances there may be a spacer both between the SNP and the click chemistry reagent, and the click chemistry reagent and the mass tag.

The spacer might be a polyethylene glycol (PEG) spacer, a poly(N-vinylpyrolide) (PVP) spacer, a polyglycerol (PG) spacer, poly(N-(2-hydroxylpropyl)methacrylamide) spacer, or a polyoxazoline (POZ, such as polymethyloxazoline, polyethyloxazoline or polypropyloxazoline) or a C5-C20 non-cyclic alkyl spacer. For example, the spacer may be a PEG spacer with 3 or more, 4 or more, 5 or more, 6 or more, 7 or more, 8 or more, 9 or more, 10 or more, 11 or more, 12 or more, 15 or more of 20 or more EG (ethylene glycol) units. The PEG linker may have from 3 to 12 EG units, from 4 to 10, or may have 4, 5, 6, 7, 8, 9, or 10 EG units. The linker may include cystamine or derivatives thereof, may include one or more disulfide groups, or may be any other suitable linker known to one of skill in the art.

Spacers may be beneficial to minimize the steric effect of the mass tag on the SBP to which is conjugated. Hydrophilic spacers, such as PEG based spacers, may also act to improve the solubility of the mass-tagged SBP and act to prevent aggregation.

SBPs (Specific Binding Pair Members)

Mass cytometry, including imaging mass cytometry is based on the principle of specific binding between members of specific binding pairs. The mass tag is linked to a specific binding pair member, and this localises the mass tag to the target/analyte which is the other member of the pair. Specific binding does not require binding to just one molecular species to the exclusion of others, however. Rather it defines that the binding is not-nonspecific, i.e. not a random interaction. An example of an SBP that binds to multiple targets would therefore be an antibody which recognises an epitope that is common between a number of different proteins. Here, binding would be specific, and mediated by the CDRs of the antibody, but multiple different proteins would be detected by the antibody. The common epitopes may be naturally occurring, or the common epitope could be an artificial tag, such as a FLAG tag. Similarly, for nucleic acids, a nucleic acid of defined sequence may not bind exclusively to a fully complementary sequence, but varying tolerances of mismatch can be introduced under the use of hybridisation conditions of a differing stringencies, as would be appreciated by one of skill in the art. Nonetheless, this hybridisation is not non-specific, because it is mediated by homology between the SBP nucleic acid and the target analyte. Similarly, ligands can bind specifically to multiple receptors, a facile example being TNFα which binds to both TNFR1 and TNFR2.

The SBP may comprise any of the following: a nucleic acid duplex; an antibody/antigen complex; a receptor/ligand pair; or an aptamer/target pair. Thus a labelling atom can be attached to a nucleic acid probe which is then contacted with a tissue sample so that the probe can hybridise to complementary nucleic acid(s) therein e.g. to form a DNA/DNA duplex, a DNA/RNA duplex, or a RNA/RNA duplex. Similarly, a labelling atom can be attached to an antibody which is then contacted with a tissue sample so that it can bind to its antigen. A labelling atom can be attached to a ligand which is then contacted with a tissue sample so that it can bind to its receptor. A labelling atom can be attached to an aptamer ligand which is then contacted with a tissue sample so that it can bind to its target. Thus, labelled SBP members can be used to detect a variety of targets in a sample, including DNA sequences, RNA sequences, proteins, sugars, lipids, or metabolites.

The mass-tagged SBP therefore can be a protein or peptide, or a polynucleotide or oligonucleotide.

Examples of protein SBPs include an antibody or antigen binding fragment thereof, a monoclonal antibody, a polyclonal antibody, a bispecific antibody, a multispecific antibody, an antibody fusion protein, scFv, antibody mimetic, avidin, streptavidin, neutravidin, biotin, or a combination thereof, wherein optionally the antibody mimetic comprises a nanobody, affibody, affilin, affimer, affitin, alphabody, anticalin, avimer, DARPin, Fynomer, kunitz domain peptide, monobody, or any combination thereof, a receptor, such as a receptor-Fc fusion, a ligand, such as a ligand-Fc fusion, a lectin, for example an agglutinin such as wheat germ agglutinin.

The peptide may be a linear peptide, or a cyclical peptide, such as a bicyclic peptide. One example of a peptide that can be used is Phalloidin.

A polynucleotide or oligonucleotide generally refers to a single- or double-stranded polymer of nucleotides containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), yPNAs, morpholino polynucleotides, locked nucleic acids (LNAs), threose nucleic acid (TNA), 2'-0-Methyl polynucleotides, 2'-0-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding.

Antibody SBP Members

In a typical embodiment, the labelled SBP member is an antibody. Labelling of the antibody can be achieved through conjugation of one or more labelling atom binding molecules to the antibody, by attachment of a mass tag using e.g. NHS-amine chemistry, sulfhydryl-maleimide chemistry, or the click chemistry (such as strained alkyne and azide, strained alkyne and nitrone, strained alkene and tetrazine etc.). Antibodies which recognise cellular proteins that are useful for imaging are already widely available for IHC usage, and by using labelling atoms instead of current labelling techniques (e.g. fluorescence) these known antibodies can be readily adapted for use in methods disclosure herein, but with the benefit of increasing multiplexing capability. Antibodies can recognise targets on the cell surface or targets within a cell. Antibodies can recognise a variety of targets e.g. they can specifically recognise individual proteins, or can recognise multiple related proteins which share common epitopes, or can recognise specific post-translational modifications on proteins (e.g. to distinguish between tyrosine and phosphor-tyrosine on a protein of interest, to distinguish between lysine and acetyl-lysine, to detect ubiquitination, etc.). After binding to its target, labelling atom(s) conjugated to an antibody can be detected to reveal the location of that target in a sample.

The labelled SBP member will usually interact directly with a target SBP member in the sample. In some embodiments, however, it is possible for the labelled SBP member to interact with a target SBP member indirectly e.g. a primary antibody may bind to the target SBP member, and a labelled secondary antibody can then bind to the primary antibody, in the manner of a sandwich assay. Usually, however, the method relies on direct interactions, as this can be achieved more easily and permits higher multiplexing. In both cases, however, a sample is contacted with a SBP member which can bind to a target SBP member in the sample, and at a later stage label attached to the target SBP member is detected.

Nucleic Acid SBPs, and Labelling Methodology Modifications

RNA is another biological molecule which the methods and apparatus disclosed herein are capable of detecting in a specific, sensitive and if desired quantitative manner. In the same manner as described above for the analysis of proteins, RNAs can be detected by the use of a SBP member labelled with an elemental tag that specifically binds to the RNA (e.g. an poly nucleotide or oligonucleotide of complementary sequence as discussed above, including a locked nucleic acid (LNA) molecule of complementary sequence, a peptide nucleic acid (PNA) molecule of complementary sequence, a plasmid DNA of complementary sequence, an amplified DNA of complementary sequence, a fragment of RNA of complementary sequence and a fragment of genomic DNA of complementary sequence). RNAs include not only the mature mRNA, but also the RNA processing intermediates and nascent pre-mRNA transcripts.

In certain embodiments, both RNA and protein are detected using methods of the claimed invention.

To detect RNA, cells in biological samples as discussed herein may be prepared for analysis of RNA and protein content using the methods and apparatus described herein. In certain aspects, cells are fixed and permeabilized prior to the hybridization step. Cells may be provided as fixed and/or pemeabilized. Cells may be fixed by a crosslinking fixative, such as formaldehyde, glutaraldehyde. Alternatively or in addition, cells may be fixed using a precipitating fixative, such as ethanol, methanol or acetone. Cells may be permeabilized by a detergent, such as polyethylene glycol (e.g., Triton X-100), Polyoxyethylene (20) sorbitan monolaurate (Tween-20), Saponin (a group of amphipathic glycosides), or chemicals such as methanol or acetone. In certain cases, fixation and permeabilization may be performed with the same reagent or set of reagents. Fixation and permeabilization techniques are discussed by Jamur et al. in "Permeabilization of Cell Membranes" (Methods Mol. Biol., 2010).

Detection of target nucleic acids in the cell, or "in-situ hybridization" (ISH), has previously been performed using fluorophore-tagged oligonucleotide probes. As discussed herein, mass-tagged oligonucleotides, coupled with ionization and mass spectrometry, can be used to detect target nucleic acids in the cell. Methods of in-situ hybridization are known in the art (see Zenobi et al. "Single-Cell Metabolomics: Analytical and Biological Perspectives," Science vol. 342, no. 6163, 2013). Hybridization protocols are also described in U.S. Pat. No. 5,225,326 and US Pub. No. 2010/0092972 and 2013/0164750, which are incorporated herein by reference.

Prior to hybridization, cells present in suspension or immobilized on a solid support may be fixed and permeabilized as discussed earlier. Permeabilization may allow a cell to retain target nucleic acids while permitting target hybridization nucleotides, amplification oligonucleotides, and/or mass-tagged oligonucleotides to enter the cell. The cell may be washed after any hybridization step, for example, after hybridization of target hybridization oligonucleotides to nucleic acid targets, after hybridization of amplification oligonucleotides, and/or after hybridization of mass-tagged oligonucleotides.

Cells can be in suspension for all or most of the steps of the method, for ease of handling. However, the methods are also applicable to cells in solid tissue samples (e.g., tissue sections) and/or cells immobilized on a solid support (e.g., a slide or other surface). Thus, sometimes, cells can be in suspension in the sample and during the hybridization steps. Other times, the cells are immobilized on a solid support during hybridization.

Target nucleic acids include any nucleic acid of interest and of sufficient abundance in the cell to be detected by the subject methods. Target nucleic acids may be RNAs, of which a plurality of copies exist within the cell. For example, 10 or more, 20 or more, 50 or more, 100 or more, 200 or more, 500 or more, or 1000 or more copies of the target RNA may be present in the cell. A target RNA may be a messenger NA (mRNA), ribosomal RNA (rRNA), transfer RNA (tRNA), small nuclear RNA (snRNA), small interfering RNA (siRNA), long noncoding RNA (lncRNA), or any other type of RNA known in the art. The target RNA may be 20 nucleotides or longer, 30 nucleotides or longer, 40 nucleotides or longer, 50 nucleotides or longer, 100 nucleotides or longer, 200 nucleotides or longer, 500 nucleotides or longer, 1000 nucleotides or longer, between 20 and 1000 nucleotides, between 20 and 500 nucleotides in length, between 40 and 200 nucleotides in length, and so forth.

In certain embodiments, a mass-tagged oligonucleotide may be hybridized directly to the target nucleic acid sequence. However, hybridization of additional oligonucleotides may allow for improved specificity and/or signal amplification.

In certain embodiments, two or more target hybridization oligonucleotides may be hybridized to proximal regions on the target nucleic acid, and may together provide a site for hybridization of an additional oligonucleotides in the hybridization scheme.

In certain embodiments, the mass-tagged oligonucleotide may be hybridized directly to the two or more target hybridization oligonucleotides. In other embodiments, one or more amplification oligonucleotides may be added, simultaneously or in succession, so as to hybridize the two or more target hybridization oligonucleotides and provide multiple hybridization sites to which the mass-tagged oligonucleotide can bind. The one or more amplification oligonucleotides, with or without the mass-tagged oligonucleotide, may be provided as a multimer capable of hybridizing to the two or more target hybridization oligonucleotides.

While the use of two or more target hybridization oligonucleotides improves specificity, the use of amplification oligonucleotides increases signal. Two target hybridization oligonucleotides are hybridized to a target RNA in the cell. Together, the two target hybridization oligonucleotides provide a hybridization site to which an amplification oligonucleotide can bind. Hybridization and/or subsequent washing of the amplification oligonucleotide may be performed at a temperature that allows hybridization to two proximal target hybridization oligonucleotides, but is above the melting temperature of the hybridization of the amplification oligonucleotide to just one target hybridization oligonucleotide. The first amplification oligonucleotide provides multiple hybridization sites, to which second amplification oligonucleotides can be bound, forming a branched pattern. Mass-tagged oligonucleotides may bind to multiple hybridization sites provided by the second amplification nucleotides. Together, these amplification oligonucleotides (with or without mass-tagged oligonucleotides) are referred to herein as a "multimer". Thus the term "amplification oligonucleotide" includes oligonucleotides that provides multiple copies of the same binding site to which further oligonucleotides can anneal. By increasing the number of binding sites for other oligonucleotides, the final number of labels that can be found to a target is increased. Thus, multiple labelled oligonucleotides are hybridized, indirectly, to a single target RNA. This is enables the detection of low copy number RNAs, by increasing the number of detectable atoms of the element used per RNA.

One particular method for performing this amplification comprises using the RNAscope® method from Advanced cell diagnostics, as discussed in more detail below. A further alternative is the use of a method that adapts the Quanti- Gene® FlowRNA method (Affymetrix eBioscience). The assay is based on oligonucleotide pair probe design with branched DNA (bDNA) signal amplification. There are more than 4,000 probes in the catalog or custom sets can be requested at no additional charge. In line with the previous paragraph, the method works by hybridization of target hybridization oligonucleotides to the target, followed by the formation of a branched structure comprising first amplification oligonucleotides (termed preamplification oligonucleotides in the QuantiGene® method) to form a stem to which multiple second amplification oligonucleotides can anneal (termed simply amplification oligonucleotides in the QuantiGene® method). Multiple mass-tagged oligonucleotides can then bind.

Another means of amplification of the RNA signal relies on the rolling circle means of amplification (RCA). There are various means why which this amplification system can be introduced into the amplification process. In a first instance, a first nucleic acid is used as the hybridisation nucleic acid wherein the first nucleic acid is circular. The first nucleic acid can be single stranded or may be double-stranded. It comprises as sequence complementary to the target RNA. Following hybridisation of the first nucleic acid to the target RNA, a primer complementary to the first nucleic acid is hybridised to the first nucleic acid, and used for primer extension using a polymerase and nucleic acids, typically exogenously added to the sample. In some instances, however, when the first nucleic acid is added to sample, it may already have the primer for extension hybridised to it. As a result of the first nucleic acid being circular, once the primer extension has completed a full round of replication, the polymerase can displace the primer and extension continues (i.e. without 5'→3' exonuclease activity), producing linked further and further chained copies of the complement of the first nucleic acid, thereby amplifying that nucleic acid sequence. Oligonucleotides comprising an elemental tag (RNA or DNA, or LNA or PNA and the like) as discussed above) may therefore be hybridised to the chained copies of the complement of the first nucleic acid. The degree of amplification of the RNA signal can therefore be controlled by the length of time allotted for the step of amplification of the circular nucleic acid.

In another application of RCA, rather than the first, e.g., oligonucleotide that hybridises to the target RNA being circular, it may be linear, and comprise a first portion with a sequence complementary to its target and a second portion which is user-chosen. A circular RCA template with sequence homologous to this second portion may then be hybridised to this the first oligonucleotide, and RCA amplification carried out as above. The use of a first, e.g., oligonucleotide having a target specific portion and user-chosen portion is that the user-chosen portion can be selected so as to be common between a variety of different probes. This is reagent-efficient because the same subsequent amplification reagents can be used in a series of reactions detecting different targets. However, as understood by the skilled person, when employing this strategy, for individual detection of specific RNAs in a multiplexed reaction, each first nucleic acid hybridising to the target RNA will need to have a unique second sequence and in turn each circular nucleic acid should contain unique sequence that can be hybridised by the labelled oligonucleotide. In this manner, signal from each target RNA can be specifically amplified and detected.

Other configurations to bring about RCA analysis will be known to the skilled person. In some instances, to prevent the first, e.g., oligonucleotide dissociating from the target during the following amplification and hybridisation steps, the first, e.g., oligonucleotide may be fixed following hybridisation (such as by formaldehyde).

Further, hybridisation chain reaction (HCR) may be used to amplify the RNA signal (see, e.g., Choi et al., 2010, Nat. Biotech, 28:1208-1210). Choi explains that an HCR amplifier consists of two nucleic acid hairpin species that do not polymerise in the absence of an initiator. Each HCR hairpin consists of an input domain with an exposed single-stranded toehold and an output domain with a single-stranded toehold hidden in the folded hairpin. Hybridization of the initiator to the input domain of one of the two hairpins opens the hairpin to expose its output domain. Hybridization of this (previously hidden) output domain to the input domain of the second hairpin opens that hairpin to expose an output domain identical in sequence to the initiator. Regeneration of the initiator sequence provides the basis for a chain reaction of alternating first and second hairpin polymerization steps leading to formation of a nicked double-stranded 'polymer'. Either or both of the first and second hairpins can be labelled with an elemental tag in the application of the methods and apparatus disclosed herein. As the amplification procedure relies on output domains of specific sequence, various discrete amplification reactions using separate sets of hairpins can be performed independently in the same process. Thus this amplification also permits amplification in multiplex analyses of numerous RNA species. As Choi notes, HCR is an isothermal triggered self-assembly process. Hence, hairpins should penetrate the sample before undergoing triggered self-assembly in situ, suggesting the potential for deep sample penetration and high signal-to-background ratios Hybridization may include contacting cells with one or more oligonucleotides, such as target hybridization oligonucleotides, amplification oligonucleotides, and/or mass-tagged oligonucleotides, and providing conditions under which hybridization can occur. Hybridization may be performed in a buffered solution, such as saline sodium-citrate (SCC) buffer, phosphate-buffered saline (PBS), saline-sodium phosphate-EDTA (SSPE) buffer, TNT buffer (having Tris-HCl, sodium chloride and Tween 20), or any other suitable buffer. Hybridization may be performed at a temperature around or below the melting temperature of the hybridization of the one or more oligonucleotides.

Specificity may be improved by performing one or more washes following hybridization, so as to remove unbound oligonucleotide. Increased stringency of the wash may improve specificity, but decrease overall signal. The stringency of a wash may be increased by increasing or decreasing the concentration of the wash buffer, increasing temperature, and/or increasing the duration of the wash. RNAse inhibitor may be used in any or all hybridization incubations and subsequent washes.

A first set of hybridization probes, including one or more target hybridizing oligonucleotides, amplification oligonucleotides and/or mass-tagged oligonucleotides, may be used to label a first target nucleic acid. Additional sets of hybridization probes may be used to label additional target nucleic acids. Each set of hybridization probes may be specific for a different target nucleic acid. The additional sets of hybridization probes may be designed, hybridized and washed so as to reduce or prevent hybridization between oligonucleotides of different sets. In addition, the mass-tagged oligonucleotide of each set may provide a unique signal. As such, multiple sets of oligonucleotides may be used to detect 2, 3, 5, 10, 15, 20 or more distinct nucleic acid targets.

Sometimes, the different nucleic acids detected are splice variants of a single gene. The mass-tagged oligonucleotide can be designed to hybridize (directly or indirectly through other oligonucleotides as explained below) within the sequence of the exon, to detect all transcripts containing that exon, or may be designed to bridge the splice junctions to detect specific variants (for example, if a gene had three exons, and two splice variants—exons 1-2-3 and exons 1-3—then the two could be distinguished: variant 1-2-3 could be detected specifically by hybridizing to exon 2, and variant 1-3 could be detected specifically by hybridizing across the exon 1-3 junction.

Histochemical Stains

The histochemical stain reagents having one or more intrinsic metal atoms may be combined with other reagents and methods of use as described herein. For example, histochemical stains may be colocalized (e.g., at cellular or subcellular resolution) with metal containing drugs, metal-labelled antibodies, and/or accumulated heavy metals. In certain aspects, one or more histochemical stains may be used at lower concentrations (e.g., less than half, a quarter, a tenth, etc.) from what is used for other methods of imaging (e.g., fluorescence microscopy, light microscopy, or electron microscopy).

To visualize and identify structures, a broad spectrum of histological stains and indicators are available and well characterized. The metal-containing stains have a potential to influence the acceptance of the imaging mass cytometry by pathologists. Certain metal containing stains are well known to reveal cellular components, and are suitable for use in the subject invention. Additionally, well defined stains can be used in digital image analysis providing contrast for feature recognition algorithms. These features are strategically important for the development of imaging mass cytometry.

Often, morphological structure of a tissue section can be contrasted using affinity products such as antibodies. They are expensive and require additional labelling procedure using metal-containing tags, as compared to using histochemical stains. This approach was used in pioneering works on imaging mass cytometry using antibodies labelled with available lanthanide isotopes thus depleting mass (e.g. metal) tags for functional antibodies to answer a biological question.

The subject invention expands the catalog of available isotopes including such elements as Ag, Au, Ru, W, Mo, Hf, Zr (including compounds such as Ruthenium Red used to identify mucinous stroma, Trichrome stain for identification of collagen fibers, osmium tetroxide as cell counterstain). Silver staining is used in karyotyping. Silver nitrate stains the nucleolar organization region (NOR)-associated protein, producing a dark region wherein the silver is deposited and denoting the activity of rRNA genes within the NOR. Adaptation to IMC may require that the protocols (e.g., oxidation with potassium permanganate and a silver concentration of 1% during) be modified for use lower concentrations of silver solution, e.g., less than 0.5%, 0.01%, or 0.05% silver solution.

Autometallographic amplification techniques have evolved into an important tool in histochemistry. A number of endogenous and toxic heavy metals form sulfide or selenide nanocrystals that can be autocatalytically amplified by reaction with Ag ions. The larger Ag nanocluster can then be readily visualized by IMC. At present, robust protocols for the silver amplified detection of Zn—S/Se nanocrystals have been established as well as detection of selenium through formation of silver-selenium nanocrystals. In addition, commercially available quantum dots (detection of Cd) are also autocatalytically active and may be used as histochemical labels.

Aspects of the subject invention may include histochemical stains and their use in imaging by elemental mass spectrometry. Any histochemical stain resolvable by elemental mass spectrometry may be used in the subject invention. In certain aspects, the histochemical stain includes one or more atoms of mass greater than a cut-off of the elemental mass spectrometer used to image the sample, such as greater than 60 amu, 80 amu, 100 amu, or 120 amu. For example, the histochemical stain may include a metal tag (e.g., metal atom) as described herein. The metal atom may be chelated to the histochemical stain, or covalently bound within the chemical structure of the histochemical stain. In certain aspects, the histochemical stain may be an organic molecule. Histochemical stains may be polar, hydrophobic (e.g., lipophilic), ionic or may comprise groups with different properties. In certain aspects, a histochemical stain may comprise more than one chemical.

Histochemical stains include small molecules of less than 2000, 1500, 1000, 800, 600, 400, or 200 amu. Histochemical stains may bind to the sample through covalent or non-covalent (e.g., ionic or hydrophobic) interactions. Histochemical stains may provide contrast to resolve the morphology of the biological sample, for example, to help identify individual cells, intracellular structures, and/or extracellular structures. Intracellular structures that may be resolved by histochemical stains include cell membrane, cytoplasm, nucleus, Golgi body, ER, mitochondria, and other cellular organelles. Histochemical stains may have an affinity for a type of biological molecule, such as nucleic acids, proteins, lipids, phospholipids or carbohydrates. In certain aspects, a histochemical stain may bind a molecule other than DNA. Suitable histochemical stains also include stains that bind extracellular structures (e.g., structures of the extracellular matrix), including stroma (e.g., mucosal stroma), basement membrane, interstitial stroma, proteins such as collage or elastin, proteoglycans, non-proteoglycan polysaccharides, extracellular vesicles, fibronectin, laminin, and so forth.

In certain aspects, histochemical stains and/or metabolic probes may indicate a state of a cell or tissue. For example, histochemical stains may include vital stains such as cisplatin, eosin, and propidium iodide. Other histochemical stains may stain for hypoxia, e.g., may only bind or deposit under hypoxic conditions. Probes such as Iododeoxyuridine (IdU) or a derivative thereof, may stain for cell proliferation. In certain aspects, the histochemical stain may not indicate the state of the cell or tissue. Probes that detect cell state (e.g., viability, hypoxia and/or cell proliferation) but are administered in-vivo (e.g., to a living animal or cell culture) be used in any of the subject methods but do not qualify as histochemical stains.

Histochemical stains may have an affinity for a type of biological molecule, such as nucleic acids (e.g., DNA and/or RNA), proteins, lipids, phospholipids, carbohydrates (e.g., sugars such as mono-saccharides or di-saccharides or polyols; oligosaccharides; and/or polysaccharides such as starch or glycogen), glycoproteins, and/or glycolipids. In certain aspects the histochemical stain may be a counterstain.

The following are examples of specific histochemical stains and their use in the subject methods:

Ruthenium Red stain as a metal-containing stain for mucinous stroma detection may be used as follows: Immunostained tissue (e.g., de-paraffinized FFPE or cryosection) may be treated with 0.0001-0.5%, 0.001-0.05%, less than 0.1%, less than 0.05%, or around 0.0025% Ruthenium Red (e.g., for at least 5 minutes, at least 10 minutes, at least 30 minutes, or around 30 min at 4-42° C., or around room temperature). The biological sample may be rinsed, for example with water or a buffered solution. Tissue may then be dried before imaging by elemental mass spectrometry.

Phosphotungstic Acid (e.g., as a Trichrome stain) may be used as a metal-containing stain for collagen fibers. Tissue sections on slides (de-paraffinized FFPE or cryosection) may be fixed in Bouin's fluid (e.g., for at least 5 minutes, at least 10 minutes, at least 30 minutes, or around 30 minutes at 4-42° C. or around room temperature). The sections may then be treated with 0.0001%-0.01%, 0.0005%-0.005%, or around 0.001% Phosphotungstic Acid for (e.g., for at least 5 minutes, at least 10 minutes, at least 30 minutes, or around 15 minutes at 4-42° C. or around room temperature). Sample may then be rinsed with water and/or buffered solution, and optionally dried, prior to imaging by elemental mass spectrometry. Trichrome stain may be used at a dilution (e.g., 5 fold, 10 fold, 20 fold, 50 fold or great dilution) compared to concentrations used for imaging by light (e.g., fluorescence) microscopy.

In some embodiments, the histochemical stain is an organic molecule. In some embodiments, the second metal is covalently bound. In some embodiments, the second metal is chelated. In some embodiments, the histochemical stain specifically binds cell membrane. In some embodiments, the histochemical stain is osmium tetroxide. In some embodiments, the histochemical stain is lipophilic. In some embodiments, the histochemical stain specifically binds an extracellular structure. In some embodiments, the histochemical stain specifically binds extracellular collagen. In some embodiments, the histochemical stain is a trichrome stain comprising phosphotungstic/phosphomolybdic acid. In some embodiments, trichrome stain is used after contacting the sample with the antibody, such as at a lower concentration than would be used for optical imaging, for instance wherein the concentration is a 50 fold dilution of trichrome stain or greater.

Metal-Containing Drugs

Metals in medicine is a new and exciting field in pharmacology. Little is known about the cellular structures that are involved in transiently storing metal ions prior to their incorporation into metalloproteins, nucleic acid metal complexes or metal-containing drugs or the fate of metal ions upon protein or drug degradation. An important first step towards unravelling the regulatory mechanisms involved in trace metal transport, storage, and distribution represents the identification and quantitation of the metals, ideally in context of their native physiological environment in tissues, cells, or even at the level of individual organelles and subcellular compartments. Histological studies are typically carried out on thin sections of tissue or with cultured cells.

A number of metal-containing drugs are being used for treatment of various diseases, however not enough is known about their mechanism of action or biodistribution: cisplatin, ruthenium imidazole, metallocene-based anti-cancer agents with Mo, tungstenocenes with W, B-diketonate complexes with Hf or Zr, auranofin with Au, polyoxomolybdate drugs. Many metal complexes are used as MRI contrast agents (Gd(III) chelates). Characterization of the uptake and biodistribution of metal-based anti-cancer drugs is of critical importance for understanding and minimizing the underlying toxicity.

The atomic masses of certain metals present in drugs fall into the range of mass cytometry. Specifically, cisplatin and others with Pt complexes (iproplatin, lobplatin) are extensively used as a chemotherapeutic drug for treating a wide range of cancers. The nephrotoxicity and myelotoxicity of platinum-based anti-cancer drugs is well known. With the methods and reagents described herein, their subcellular localization within tissue sections, and colocalization with mass- (e.g. metal-) tagged antibodies and/or histochemical stains can now be examined. Chemotherapeutic drugs may be toxic to certain cells, such as proliferating cells, through direct DNA damage, inhibition of DNA damage repair pathways, radioactivity, and so forth. In certain aspects, chemotherapeutic drugs may be targeted to tumor through an antibody intermediate.

In certain aspects, the metal containing drug is a chemotherapeutic drug. Subject methods may include administering the metal containing drug to a living animal, such as an animal research model or human patient as previously described, prior to obtaining the biological sample. The biological sample may be, for example, a biopsy of cancerous tissue or primary cells. Alternatively, the metal containing drug may be added directly to the biological sample, which may be an immortalized cell line or primary cells. When the animal is a human patient, the subject methods may include adjusting a treatment regimen that includes the metal containing drug, based on detecting the distribution of the metal containing drug.

The method step of detecting the metal containing drug may include subcellular imaging of the metal containing drug by elemental mass spectrometry, and may include detecting the retention of the metal containing drug in an intracellular structure (such as membrane, cytoplasm, nucleus, Golgi body, ER, mitochondria, and other cellular organelles) and/or extracellular structure (such as including stroma, mucosal stroma, basement membrane, interstitial stroma, proteins such as collage or elastin, proteoglycans, non-proteoglycan polysaccharides, extracellular vesicles, fibronectin, laminin, and so forth).

A histochemical stain and/or mass- (e.g. metal-) tagged SBP that resolves (e.g., binds to) one or more of the above structures may be colocalized with the metal containing drug to detected retention of the drug at specific intracellular or extracellular structures. For example, a chemotherapeutic drug such as cisplatin may be colocalized with a structure such as collagen. Alternatively or in addition, the localization of the drug may be related to presence of a marker of cell viability, cell proliferation, hypoxia, DNA damage response, or immune response.

In some embodiments, the metal containing drug comprises a non-endogenous metal, such as wherein the non-endogenous metal is platinum, palladium, cerium, cadmium, silver or gold. In certain aspects, the metal containing drug is one of cisplatin, ruthenium imidazole, metallocene-based anti-cancer agents with Mo, tungstenocenes with W, B-diketonate complexes with Hf or Zr, auranofin with Au, polyoxomolybdate drugs, N-myristoyltransferase-1 inhibitor (Tris(dibenzylideneacetone) dipalladium) with Pd, or a derivative thereof. For example the drug may comprise Pt, and may be, for example, cisplatin, carboplatin, oxaliplatin, iproplatin, lobaplatin or a derivative thereof. The metal containing drug may include a non-endogenous metal, such as platinum (Pt), ruthenium (Ru), molybdenum (Mo), tungsten (W), hafnium (Hf), zirconium (Zr), gold (Au), gadolinium (Gd), palladium (Pd) or an isotope thereof. Gold compounds (Auranofin, for example) and gold nanoparticle bioconjugates for photothermal therapy against cancer can be identified in tissue sections.

Multiplexed Analysis

One feature of the disclosure is its ability to detect multiple (e.g. 10 or more, and even up to 100 or more) different target SBP members in a sample e.g. to detect multiple different proteins and/or multiple different nucleic acid sequences. To permit differential detection of these target SBP members their respective SBP members should carry different labelling atoms such that their signals can be distinguished. For instance, where ten different proteins are being detected, ten different antibodies (each specific for a different target protein) can be used, each of which carries a unique label, such that signals from the different antibodies can be distinguished. In some embodiments, it is desirable to use multiple different antibodies against a single target e.g. which recognise different epitopes on the same protein. Thus, a method may use more antibodies than targets due to redundancy of this type. In general, however, the disclosure will use a plurality of different labelling atoms to detect a plurality of different targets.

If more than one labelled antibody is used with the disclosure, it is preferable that the antibodies should have similar affinities for their respective antigens, as this helps to ensure that the relationship between the quantity of labelling atoms detected and the abundance of the target antigen in the tissue sample will be more consistent across different SBPs (particularly at high scanning frequencies). Similarly, it is preferable if the labelling of the various antibodies has the same efficiency, so that the antibodies each carry a comparable quantity of the labelling atom.

In some instances, the SBP may carry a fluorescent label as well as an elemental tag. Fluorescence of the sample may then be used to determine regions of the sample, e.g. a tissue section, comprising material of interest which can then be sampled for detection of labelling atoms. E.g. a fluorescent label may be conjugated to an antibody which binds to an antigen abundant on cancer cells, and any fluorescent cell may then be targeted to determine expression of other cellular proteins that are about by SBPs conjugated to labelling atoms.

If a target SBP member is located intracellularly, it will typically be necessary to permeabilize cell membranes before or during contacting of the sample with the labels. For example, when the target is a DNA sequence but the labelled SBP member cannot penetrate the membranes of live cells, the cells of the tissue sample can be fixed and permeabilised. The labelled SBP member can then enter the cell and form a SBP with the target SBP member. In this respect, known protocols for use with IHC and FISH can be utilised.

A method may be used to detect at least one intracellular target and at least one cell surface target. In some embodiments, however, the disclosure can be used to detect a plurality of cell surface targets while ignoring intracellular targets. Overall, the choice of targets will be determined by the information which is desired from the method, as the disclosure will provide an image of the locations of the chosen targets in the sample.

As described further herein, specific binding partners (i.e., affinity reagents) comprising labelling atoms may be used to stain (contact) a biological sample. Suitable specific binging partners include antibodies (including antibody fragments). Labelling atoms may be distinguishable by mass spectrometry (i.e., may have different masses). Labelling atoms may be referred to herein as metal tags when they include one or more metal atoms. Metal tags may include a polymer with a carbon backbone and a plurality of pendant groups that each bind a metal atom. Alternatively, or in addition, metal tags may include a metal nanoparticle. Antibodies may be tagged with a metal tag by a covalent or non-covalent interaction.

Antibody stains may be used to image proteins at cellular or subcellular resolution. Aspects of the invention include contacting the sample with one or more antibodies that specifically bind a protein expressed by cells of the biological sample, wherein the antibody is tagged with a first metal tag. For example, the sample may be contacted with 5 or more, 10 or more, 15 or more, 20 or more, 30 or more, 40 or more, 50 or more antibodies, each with a distinguishable metal tag. The sample may further be contacted with one or more histochemical stains before, during (e.g., for ease of workflow), or after (e.g., to avoid altering antigen targets of antibodies) staining the sample with antibodies. The sample may further comprise one or more metal containing drugs and/or accumulated heavy metals as described herein.

Metal tagged antibodies for use in the subject inventions may specifically bind a metabolic probe that does not comprise a metal (e.g., EF5). Other metal tagged antibodies may specifically bind a target (e.g., of epithelial tissue, stromal tissue, nucleus, etc.) of traditional stains used in fluorescence and light microscopy. Such antibodies include anti-cadherin, anti-collagen, anti-keratin, anti-EFS, anti-Histone H3 antibodies, and a number of other antibodies known in the art.

Histochemical Stains

Histochemical stain reagents having one or more intrinsic metal atoms and methods of use described herein may be combined with other reagents and methods of use as described herein. For example, histochemical stains may be colocalized (e.g., at cellular or subcellular resolution) with metal containing drugs, metal-labelled antibodies, and/or accumulated heavy metals. In certain aspects, one or more histochemical stains may be used at lower concentrations (e.g., less than half, a quarter, a tenth, etc.) from what is used for other methods of imaging (e.g., fluorescence microscopy, light microscopy, or electron microscopy).

To visualize and identify structures, a broad spectrum of histological stains and indicators are available and well characterized. The metal-containing stains have a potential to influence the acceptance of the imaging mass cytometry by pathologists. Certain metal containing stains are well known to reveal cellular components, and are suitable for use in the subject invention. Additionally, well defined stains can be used in digital image analysis providing contrast for feature recognition algorithms. These features are strategically important for the development of imaging mass cytometry.

Often, morphological structure of a tissue section can be contrasted using affinity products such as antibodies. They are expensive and require additional labelling procedure using metal-containing tags, as compared to using histochemical stains. This approach was used in pioneering works on imaging mass cytometry using antibodies labelled with available lanthanide isotopes thus depleting metal tags for functional antibodies to answer a biological question.

The subject invention expands the catalog of available isotopes including such elements as Ag, Au, Ru, W, Mo, Hf, Zr (including compounds such as Ruthenium Red used to identify mucinous stroma, Trichrome stain for identification of collagen fibers, osmium tetroxide as cell counterstain). Silver staining is used in karyotyping. Silver nitrate stains the nucleolar organization region (NOR)-associated protein, producing a dark region wherein the silver is deposited and denoting the activity of rRNA genes within the NOR. Adaptation to IMC may require that the protocols (e.g., oxidation with potassium permanganate and a silver concentration of 1% during) be modified for use lower concentrations of silver solution, e.g., less than 0.5%, 0.01%, or 0.05% silver solution.

Autometallographic amplification techniques have evolved into an important tool in histochemistry. A number of endogenous and toxic heavy metals form sulfide or selenide nanocrystals that can be autocatalytically amplified by reaction with Ag ions. The larger Ag nanocluster can then be readily visualized by IMC. At present, robust protocols for the silver amplified detection of Zn—S/Se nanocrystals have been established as well as detection of selenium through formation of silver-selenium nanocrystals. In addition, commercially available quantum dots (detection of Cd) are also autocatalytically active and may be used as histochemical labels.

Aspects of the subject invention may include histochemical stains and their use in imaging by elemental mass spectrometry. Any histochemical stain resolvable by elemental mass spectrometry may be used in the subject invention. In certain aspects, the histochemical stain includes one or more atoms of mass greater than a cut-off of the elemental mass spectrometer used to image the sample, such as greater than 60 amu, 80 amu, 100 amu, or 120 amu. For example, the histochemical stain may include a metal tag (e.g., metal atom) as described herein. The metal atom may be chelated to the histochemical stain, or covalently bound within the chemical structure of the histochemical stain. In certain aspects, the histochemical stain may be an organic molecule. Histochemical stains may be polar, hydrophobic (e.g., lipophilic), ionic or may comprise groups with different properties. In certain aspects, a histochemical stain may comprise more than one chemical.

Histochemical stains include small molecules of less than 2000, 1500, 1000, 800, 600, 400, or 200 amu. Histochemical stains may bind to the sample through covalent or non-covalent (e.g., ionic or hydrophobic) interactions. Histochemical stains may provide contrast to resolve the morphology of the biological sample, for example, to help identify individual cells, intracellular structures, and/or extracellular structures. Intracellular structures that may be resolved by histochemical stains include cell membrane, cytoplasm, nucleus, Golgi body, ER, mitochondria, and other cellular organelles. Histochemical stains may have an affinity for a type of biological molecule, such as nucleic acids, proteins, lipids, phospholipids or carbohydrates. In certain aspects, a histochemical stain may bind a molecule other than DNA. Suitable histochemical stains also include stains that bind extracellular structures (e.g., structures of the extracellular matrix), including stroma (e.g., mucosal stroma), basement membrane, interstitial stroma, proteins such as collage or elastin, proteoglycans, non-proteoglycan polysaccharides, extracellular vesicles, fibronectin, laminin, and so forth.

Histochemical stains and/or metabolic probes may indicate a state of a cell or tissue. For example, histochemical stains may include vital stains such as cisplatin, eosin, and propidium iodide. Other histochemical stains may stain for hypoxia, e.g., may only bind or deposit under hypoxic conditions. Probes such as Iododeoxyuridine (IdU) or a derivative thereof, may stain for cell proliferation. In certain aspects, the histochemical stain may not indicate the state of the cell or tissue. Probes that detect cell state (e.g., viability, hypoxia and/or cell proliferation) but are administered in-vivo (e.g., to a living animal or cell culture) be used in any of the subject methods but do not qualify as histochemical stains.

Histochemical stains may have an affinity for a type of biological molecule, such as nucleic acids (e.g., DNA and/or RNA), proteins, lipids, phospholipids, carbohydrates (e.g., sugars such as mono-saccharides or di-saccharides or polyols; oligosaccharides; and/or polysaccharides such as starch or glycogen), glycoproteins, and/or glycolipids. In certain aspects the histochemical stain may be a counterstain.

Common histochemical stains that can be used herein include Ruthenium Red and Phosphotungstic Acid (e.g., as a Trichrome stain).

In addition to specific staining of sample introduce a stain into the sample, sometimes, the sample may contain a metal atom as a result of the tissue or the organism from which it was taken being administered a metal containing drug, or having accumulated metals from environmental exposure. Sometimes, tissues or animals may be tested in methods using this technique based on a pulse chase experimental strategy, to observe retention and clearance of a metal-containing material.

For instance, metals in medicine is a new and exciting field in pharmacology. Little is known about the cellular structures that are involved in transiently storing metal ions prior to their incorporation into metalloproteins, nucleic acid metal complexes or metal-containing drugs or the fate of metal ions upon protein or drug degradation. An important first step towards unravelling the regulatory mechanisms involved in trace metal transport, storage, and distribution represents the identification and quantification of the metals, ideally in context of their native physiological environment in tissues, cells, or even at the level of individual organelles and subcellular compartments. Histological studies are typically carried out on thin sections of tissue or with cultured cells.

A number of metal-containing drugs are being used for treatment of various diseases, however not enough is known about their mechanism of action or biodistribution: cisplatin, ruthenium imidazole, metallocene-based anti-cancer agents with Mo, tungstenocenes with W, B-diketonate complexes with Hf or Zr, auranofin with Au, polyoxomolybdate drugs. Many metal complexes are used as MRI contrast agents (Gd(III) chelates). Characterization of the uptake and biodistribution of metal-based anti-cancer drugs is of critical importance for understanding and minimizing the underlying toxicity.

The atomic masses of certain metals present in drugs fall into the range of mass cytometry. Specifically, cisplatin and others with Pt complexes (iproplatin, lobplatin) are extensively used as a chemotherapeutic drug for treating a wide range of cancers. The nephrotoxicity and myelotoxicity of platinum-based anti-cancer drugs is well known. With the methods and reagents described herein, their subcellular localization within tissue sections, and colocalization with metal tagged antibodies and/or histochemical stains can now be examined. Chemotherapeutic drugs may be toxic to certain cells, such as proliferating cells, through direct DNA damage, inhibition of DNA damage repair pathways, radioactivity, and so forth. In certain aspects, chemotherapeutic drugs may be targeted to tumor through an antibody intermediate.

In certain aspects, the metal containing drug is a chemotherapeutic drug. Subject methods may include administering the metal containing drug to a living animal, such as an animal research model or human patient as previously described, prior to obtaining the biological sample. The biological sample may be, for example, a biopsy of cancerous tissue or primary cells. Alternatively, the metal containing drug may be added directly to the biological sample, which may be an immortalized cell line or primary cells. When the animal is a human patient, the subject methods may include adjusting a treatment regimen that includes the metal containing drug, based on detecting the distribution of the metal containing drug.

The method step of detecting the metal containing drug may include subcellular imaging of the metal containing drug by elemental mass spectrometry, and may include detecting the retention of the metal containing drug in an intracellular structure (such as membrane, cytoplasm, nucleus, Golgi body, ER, mitochondria, and other cellular organelles) and/or extracellular structure (such as including stroma, mucosal stroma, basement membrane, interstitial stroma, proteins such as collage or elastin, proteoglycans, non-proteoglycan polysaccharides, extracellular vesicles, fibronectin, laminin, and so forth).

A histochemical stain and/or metal-tagged SBP that resolves (e.g., binds to) one or more of the above structures may be colocalized with the metal containing drug to detected retention of the drug at specific intracellular or extracellular structures. For example, a chemotherapeutic drug such as cisplatin may be colocalized with a structure such as collagen. Alternatively or in addition, the localization of the drug may be related to presence of a marker of cell viability, cell proliferation, hypoxia, DNA damage response, or immune response.

In certain aspects, the metal containing drug is one of cisplatin, ruthenium imidazole, metallocene-based anti-cancer agents with Mo, tungstenocenes with W, B-diketonate complexes with Hf or Zr, auranofin with Au, polyoxomolybdate drugs, N-myristoyltransferase-1 inhibitor (Tris (dibenzylideneacetone) dipalladium) with Pd, or a derivative thereof. For example the drug may comprise Pt, and may be, for example, cisplatin, carboplatin, oxaliplatin, iproplatin, lobaplatin or a derivative thereof. The metal containing drug may include a non-endogenous metal, such as platinum (Pt), ruthenium (Ru), molybdenum (Mo), tungsten (W), hafnium (Hf), zirconium (Zr), gold (Au), gadolinium (Gd), palladium (Pd) or an isotope thereof. Gold compounds (Auranofin, for example) and gold nanoparticle bioconjugates for photothermal therapy against cancer can be identified in tissue sections.

Exposure to heavy metals can occur though ingestion of food or water, contact through skin, or aerosol intake. Heavy metals may accumulate in soft tissues of the body, such that prolonged exposure has serious health effects. In certain aspect, the heavy metal may be accumulated in vivo, either through controlled exposure in an animal research model or though environmental exposure in a human patient. The heavy metal may be a toxic heavy metal, such as Arsenic (As), Lead (Pb), Antimony (Sb), Bismuth (Bi), Cadmium (Cd), Osmium (Os), Thallium (TI), or Mercury (Hg).

Single Cell Analysis

Methods of the disclosure include laser ablation of multiple cells in a sample, and thus plumes from multiple cells are analysed and their contents are mapped to specific locations in the sample to provide an image. In most cases a user of the method will need to localise the signals to specific cells within the sample, rather than to the sample as a whole. To achieve this, the boundaries of cells (e.g. the plasma membrane, or in some cases the cell wall) in the sample can be demarcated.

Demarcation of cellular boundaries can be achieved in various ways. For instance, a sample can be studied using conventional techniques which can demarcate cellular boundaries, such as microscopy as discussed above. When performing these methods, therefore, an analysis system comprising a camera as discussed above is particularly useful. An image of this sample can then be prepared using a method of the disclosure, and this image can be superimposed on the earlier results, thereby permitting the detected signals to be localised to specific cells. Indeed, as discussed above, in some cases the laser ablation may be directed only to a subset of cells in the sample as determined to be of interest by the use of microscopy based techniques.

To avoid the need to use multiple techniques, however, it is possible to demarcate cellular boundaries as part of the imaging method of the disclosure. Such boundary demarcation strategies are familiar from IHC and immunocytochemistry, and these approaches can be adapted by using labels which can be detected. For instance, the method can involve labelling of target molecule(s) which are known to be located at cellular boundaries, and signal from these labels can then be used for boundary demarcation. Suitable target molecules include abundant or universal markers of cell boundaries, such as members of adhesion complexes (e.g. β-catenin or E-cadherin). Some embodiments can label more than one membrane protein in order to enhance demarcation.

In addition to demarcating cell boundaries by including suitable labels, it is also possible to demarcate specific organelles in this way. For instance, antigens such as histones (e.g. H3) can be used to identify the nucleus, and it is also possible to label mitochondrial-specific antigens, cytoskeleton-specific antigens, Golgi-specific antigens, ribosome-specific antigens, etc., thereby permitting cellular ultrastructure to be analysed by methods of the disclosure.

Signals which demarcate the boundary of a cell (or an organelle) can be assessed by eye, or can be analysed by computer using image processing. Such techniques are known in the art for other imaging techniques e.g. Arce et al. (2013; Scientific Reports 3, article 2266) describes a segmentation scheme that uses spatial filtering to determine cell boundaries from fluorescence images, Ali et al. (2011; Mach Vis Appl 23:607-21) discloses an algorithm which determines boundaries from brightfield microscopy images, Pound et al. (2012; The Plant Cell 24:1353-61) discloses the CellSeT method to extract cell geometry from confocal microscope images, and Hodneland et al. (2013; Source Code for Biology and Medicine 8:16) discloses the CellSegm MATLAB toolbox for fluorescence microscope images. A method which is useful with the disclosure uses watershed transformation and Gaussian blurring. These image processing techniques can be used on their own, or they can be used and then checked by eye.

Once cellular boundaries have been demarcated it is possible to allocate signal from specific target molecules to individual cells. It can also be possible to quantify the amount of a target analyte(s) in an individual cell e.g. by calibrating the methods against quantitative standards.

Reference Particles

As described herein, reference particles of known elemental or isotopic composition may be added to the sample (or the sample carrier) for use as a reference during detection of target elemental ions in the sample. In certain embodiments, reference particles comprise metal elements or isotopes, such as transition metals or lanthanides. For example, reference particles may comprise elements or isotopes of mass greater than 60 amu, greater than 80 amu, greater than 100 amu, or greater than 120 amu.

Target elements, such as labelling atoms, can be normalized within a sample run based on elemental ions detected from individual reference particles. For example, the subject methods may include switching between detecting elemental ions from individual reference particles and detecting only target elemental ions.

Pre-Analysis Sample Expansion Using Hydrogels

Conventional light microscopy is limited to approximately half the wavelength of the source of illumination, with a minimum possible resolution of about 200 nm. Expansion microscopy is a method of sample preparation (in particular for biological samples) that uses polymer networks to physically expand the sample and so increase the resolution of optical visualisation of a sample to around 20 nm (WO2015127183). The expansion procedures can be used to prepare samples for imaging mass spectrometry and imaging mass cytometry. By this process, a 1 μm ablation spot diameter would provide a resolution of 1 μm on an unexpanded sample, but with this 1 μm ablation spot represents ~100 nm resolution following expansion.

Expansion microscopy of biological samples generally comprises the steps of: fixation, preparation for anchoring, gelation, mechanical homogenization, and expansion.

In the fixation stage, samples chemically fixed and washed. However, specific signalling functions or enzymatic functions such as protein-protein interactions as a function of physiological state can be examined using expansion microscopy without a fixation step.

Next, the samples are prepared so that they can be attached ("anchored") to the hydrogel formed in the subsequent gelation step. Here, SBPs as discussed elsewhere herein (e.g. an antibody, nanobody, non-antibody protein, peptide, nucleic acid and/or small molecule that can specifically bind to target molecules of interest in the sample) are incubated with the sample to bind to the targets if present in the sample. Optionally, samples can be labelled (sometimes termed 'anchored') with a detectable compound useful for imaging. For optical microscopy, the detectable compound could comprise, for example, be provided by a fluorescently labelled antibody, nanobody, non-antibody protein, peptide, nucleic acid and/or small molecule that can specifically bind to target molecules of interest in the sample (US2017276578). For mass cytometry, including imaging mass cytometry, the detectable label could be provided by, for example, an elemental tag labelled antibody, nanobody, non-antibody protein, peptide, nucleic acid and/or small molecule that can specifically bind to target molecules of interest in the sample. In some instances, the SBP binding to the target does not contain a label but instead contains a feature that can be bound by a secondary SBP (e.g. a primary antibody that binds to the target and a secondary antibody that binds to the primary antibody, as common in immunohistochemical techniques). If only a primary SBP is used, this may itself be linked to a moiety that attaches or crosslinks the sample to the hydrogel formed in the subsequent gelation step so that the sample can be tethered to the hydrogel. Alternatively, if a secondary SBP is used, this may contain the moiety that attaches or crosslinks the sample to the hydrogel. In some instances, a third SBP is used, which binds to the secondary SBP. One exemplary experimental protocol is set out in Chen et al., 2015 (Science 347: 543-548) uses a primary antibody to bind to the target, a secondary antibody that binds to the primary antibody wherein the secondary antibody is attached to an oligonucleotide sequence, and then as a tertiary SBP a oligonucleotide complementary to the sequence attached to the secondary antibody, wherein the tertiary SBP comprised a methacryloyl group that can be incorporated into an acrylamide hydrogel. In some instances, the SBP comprising the moiety that is incorporated into the hydrogel also includes a label. These labels can be fluorescent labels or elemental tags and so used in subsequent analysis by, for example, flow cytometry, optical scanning and fluorometry (US2017253918), or mass cytometry or imaging mass cytometry.

The gelation stage generates a matrix in the sample, by infusing a hydrogel comprising densely cross-linked, highly charged monomers into the sample. For example, sodium acrylate along with the comonomer acrylamide and the crosslinker N-N'methylenebisacrylamide have been introduced into fixed and permeabilised brain tissue (see Chen et al., 2015). When the polymer forms, it incorporates the moiety linked to the targets in the anchoring step, so that the targets in the sample become attached to the gel matrix.

The sample is then treated with a homogenizing agent to homogenize the mechanical characteristics of the sample so that the sample does not resist expansion (WO2015127183). For example, the sample can be homogenised by degradation with an enzyme (such as a protease), by chemical proteolysis, (e.g. by cyanogen bromide), by heating of the sample to 70-95 degrees Celsius, or by physical disruption such as sonication (US2017276578).

The sample/hydrogel composite is then expanded by dialyzing the composite in a low-salt buffer or water to allow the sample to expand to 4× or 5× its original size in 3-dimensions. As the hydrogel expands, so does the sample and in particular the labels attached to targets and the hydrogel expand, while maintaining their original three dimensional arrangement of the labels. Since the samples expand are expanded in low-salt solutions or water, the expanded samples are clear, allowing optical imaging deep into the samples, and allow imaging without introduction of significant levels of contaminating elements when performing mass cytometry (e.g. by use of distilled water or purified by other processes including capacitive deionization, reverse osmosis, carbon filtering, microfiltration, ultrafiltration, ultraviolet oxidation, or electrodeionization).

The expanded sample can then be analysed by imaging techniques, providing pseudo-improved resolution. For example, fluorescence microscopy can be used with fluorescent labels, and imaging mass cytometry can be used with elemental tags, optionally in combination. Due to the swelling of the hydrogel and the concomitant increase in distance between labels in the expanded sample vis-à-vis the native sample, labels which were not capable of being resolved separately previously (be that due to diffraction limit of visible light in optical microscopy, or spot diameter in IMC).

Variants of expansion microscopy (ExM) exist, which can also be applied using the apparatus and methods disclosed herein. These variants include: protein retention ExM (proExM), expansion fluorescent in situ hybridisation (ExFISH), iterative ExM (iExM). Iterative expansion microscopy involves forming a second expandable polymer gel in a sample that has already undergone a preliminary expansion using the above techniques. The first expanded gel is dissolved and the second expandable polymer gel is then expanded to bring the total expansion to up to ~20×. For instance, Chang et al., 2017 (Nat Methods 14:593-599) base the technique on the method of Chen et al. 2015 discussed above, with the substitution that the first gel is made with a cleavable cross linker (e.g., the commercially available crosslinker N,N'-(1,2-dihydroxyethylene) bisacrylamide (DHEBA), whose diol bond can be cleaved at high pH). Following anchoring and expansion of the first gel, a labelled oligonucleotide (comprising a moiety for incorporation into a second gel) and complementary to the oligonucleotide incorporated into the first gel was added to the expanded sample. A second gel was formed incorporating the moiety of the labelled oligonucleotide, and the first gel was broken down by cleavage of the cleavable linker. The second gel was then expanded in the same manner as the first, resulting in further spatial separation of the labels, but maintaining their spatial arrangement with respect to the arrangement of the targets in the original sample. In some instances, following expansion of the first gel, an intermediate "re-embedding gel" is used, to hold the expanded first gel in place while the experimental steps are undertaken, e.g., to hybridise the labelled SBP to the first gel matrix, form the unexpanded second hydrogel, before the first hydrogel and the re-embedding gel are broken down to permit the expansion of the second hydrogel. As before the labels used can be fluorescent or elemental tags and so used in subsequent analysis by, for example, flow cytometry, optical scanning and fluorometry, or mass cytometry or imaging mass cytometry, as appropriate.

DEFINITIONS

The term "comprising" encompasses "including" as well as "consisting" e.g. a composition "comprising" X may consist exclusively of X or may include something additional e.g. X+Y.

The term "about" in relation to a numerical value x is optional and means, for example, x+10%.

The word "substantially" does not exclude "completely" e.g. a composition which is "substantially free" from Y may be completely free from Y. Where necessary, the word "substantially" may be omitted from the definition of the disclosure.

All publications, patents, and patent applications cited herein are hereby incorporated by reference in their entirety for all purposes. None is admitted to be prior art.

The invention claimed is:

1. An apparatus, comprising:
    a movable sample stage;
    an optical microscope for inspection of a sample;
    a sampling system; and
    an autofocus system comprising:
        an illumination source; and
        an autofocus sensor;
        wherein:
        the autofocus system comprises autofocus optical components,
        one of the autofocus optical components comprises a plurality of apertures,
        the plurality of apertures is arranged in a regular shape in which there is a centroid aperture at a centroid of the regular shape in addition to a vertex aperture at a vertex of the regular shape,
        the centroid aperture is configured to transmit illumination radiation to a point on the sample at which sample ablation will occur;
        a plurality of vertex apertures is configured to allow measuring a focal point around a sampling location,
        the centroid aperture is configured to facilitate the focal point calculation by readout from the point on the sample at which sample ablation will occur, and the sampling system and the autofocus system are confocal.

2. The apparatus of claim 1, wherein the optical microscope is confocal with the sampling system and the autofocus system.

3. The apparatus of claim 1, wherein the sampling system, the autofocus system, and the optical microscope all share at least some optical components.

4. The apparatus of claim 1, wherein the apparatus is configured to provide autofocusing by moving the sample stage in response to a readout from an autofocus component.

5. The apparatus of claim 1, wherein the apparatus provides sample-independent autofocusing.

6. The apparatus of claim 1, wherein the autofocusing system provides autofocusing during a sample run.

7. The apparatus of claim 1, wherein the autofocus system projects a focal map across X, Y, or X-Y coordinates.

8. The apparatus of claim 1, wherein the autofocus system provides multiple spots that may impinge the autofocus sensor.

9. The apparatus of claim 1, wherein the autofocus system comprises multiple LEDs and/or laser diodes.

10. The apparatus of claim 1, wherein the apparatus does not need to switch between autofocus and inspection apertures.

11. The apparatus of claim 1, wherein the autofocus sensor comprises an image sensor, and wherein the image sensor is shared with the optical microscope of the apparatus.

12. The apparatus of claim 1, wherein the illumination source comprises at least two LEDs, and wherein the at least two LEDs are configured to provide alternating illumination.

13. The apparatus of claim 1, wherein the illumination source comprises at least two laser diodes, and wherein the two laser diodes are configured to provide alternating illumination.

14. The apparatus of claim 1, wherein the autofocus system does not require a pre-calibrated coordinate of one or more spots or lines impinging the autofocus sensor.

15. The apparatus of claim 14, wherein autofocusing is based on an offset between the spots or lines.

16. The apparatus of claim 1, wherein two or more spots or lines impinging the autofocus sensor overlap at best focus.

17. The apparatus of claim 1, wherein autofocusing is based on the number of spots detected by the autofocus sensor.

18. The apparatus of claim 1, wherein autofocusing is based on the uniformity of spots detected by the autofocus sensor.

19. The apparatus of claim 1, wherein the sampling system is a laser ablation sampling system, and wherein the focal point of a laser source of the laser ablation sampling system is confocal with an autofocus component and the autofocus sensor of the autofocus system.

20. The apparatus of claim 1, wherein the sampling system is a laser ablation sampling system, the apparatus further comprising an ICP ionisation system coupled to the laser ablation sampling system by a gas conduit.

21. The apparatus of claim 20, further comprising a mass spectrometer.

22. A method of autofocusing using the apparatus of claim 1, comprising sampling based on autofocusing.

23. The method of claim 22, further comprising sampling mass tags from a biological sample.

* * * * *